(12) United States Patent
Lochner et al.

(10) Patent No.: US 12,324,680 B1
(45) Date of Patent: Jun. 10, 2025

(54) COMPUTER SKIN CARE SYSTEM, AR VIRTUAL SKIN MARKING AND ANALYSIS, AND HOLOPORTATION

(71) Applicants: Scott J Lochner, Pasadena, CA (US); Matthew E Lochner, Cambridge, MA (US)

(72) Inventors: Scott J Lochner, Pasadena, CA (US); Matthew E Lochner, Cambridge, MA (US)

( * ) Notice: Subject to any disclaimer, the term of this patent is extended or adjusted under 35 U.S.C. 154(b) by 68 days.

(21) Appl. No.: 18/315,933

(22) Filed: May 11, 2023

Related U.S. Application Data

(63) Continuation of application No. 18/149,825, filed on Jan. 4, 2023.

(60) Provisional application No. 63/266,591, filed on Jan. 10, 2022.

(51) Int. Cl.
  *A61B 5/00* (2006.01)
  *G16H 50/30* (2018.01)
  *A61B 90/00* (2016.01)

(52) U.S. Cl.
  CPC ............ *A61B 5/441* (2013.01); *A61B 5/0079* (2013.01); *A61B 5/6803* (2013.01); *A61B 5/6898* (2013.01); *A61B 5/7246* (2013.01); *A61B 5/7267* (2013.01); *A61B 5/7275* (2013.01); *G16H 50/30* (2018.01); *A61B 90/39* (2016.02)

(58) Field of Classification Search
  CPC ..... A61B 5/441; A61B 5/0079; A61B 5/6803; A61B 5/6898; A61B 5/7246; A61B 5/7267; A61B 5/7275; A61B 90/39; G16H 50/30
  See application file for complete search history.

(56) References Cited

U.S. PATENT DOCUMENTS

2022/0155737 A1\* 5/2022 Gartenberg .......... G05B 19/042
2022/0240779 A1\* 8/2022 Peyman ............... A61B 5/1176

\* cited by examiner

*Primary Examiner* — Mark D Remaly
(74) *Attorney, Agent, or Firm* — Scott C Harris, Esq

(57) ABSTRACT

Camera and/or other sensor analysis of skin, used to diagnose and monitor health conditions. A computer, receiving skin data from a user, where the skin data is images and/or other data of the skin. The computer processes the skin data identify skin conditions, their status, and to compare the skin data with information indicative of health conditions that are not skin diseases. This can be done by finding similar skin data to other data received from other people who have specified health conditions and/or by looking for changes from previous images. The skin data can be captured by a smart phone camera (alone or with digital peripheral attachments) or a dedicated capture device such as a periscope, one way mirror, or cubicle. An augmented reality marking system can be used to mark areas on the user's skin to compare against other previous skin images and/or data.

43 Claims, 6 Drawing Sheets

COMPUTER SKIN CARE SYSTEM, AR VIRTUAL SKIN MARKING AND ANALYSIS, AND HOLOPORTATION

This application claims priority from Provisional application No. 63/266,591, filed Jan. 10, 2022, the entire contents of which are herewith incorporated by reference.

I. BACKGROUND

The trend of modern medicine is to create machines that perform tasks previously performed by humans, ideally with greater accuracy in less time using less resources. Computers provide an efficacious level of objectivity that humans medical practitioners do not, and avoid issues of interobserver variability.

A. Overview.

Your skin is the largest organ of your body, with a total surface area of about 1.5 to 2 square meters. It helps keep you hydrated, helps regulate temperature, prevent infections, and permits the sensations of touch, heat and cold.

Your skin has three main layers:

The epidermis, the outermost layer of skin, which provides a waterproof barrier and creates your skin tone.

The dermis, beneath the epidermis, which contains tough connective tissue, hair follicles, and sweat glands. Your skin's nerves and blood vessels course through the dermis.

The deeper subcutaneous tissue (hypodermis), which is made of fat and connective tissue. The fat serves as a fuel source as well as a cushion in the event of falls and other trauma.

The main layers of skin consist of sublayers, which contain specialized cells performing specialized functions, which are further discussed on Schedule A attached hereto.

B. Skin Regeneration.

Since skin is regularly exposed, it requires frequent cell regeneration. When you get a cut or scrape, skin cells divide and multiply, replacing the skin you have lost. Even without injury, skin cells routinely die and fall off. You lose 30,000 to 40,000 dead skin cells each minute, which is about 50 million cells every day.

Skin regeneration is discussed further in more detail on Schedule B attached hereto.

C. Fingernails and Toenails.

Nails are made up of a translucent protein known as keratin. Our hair and skin are also made up of this protein. Squamous cells at the base of the nailbed multiply, forming layers which harden. This growth process is known as keratinization.

The hardened keratin layers are primarily useful for protecting the sensitive tissues at the tips of our fingers and toes. This helps to prevent injuries like scrapes and cuts which may occur while using our fingers and toes. The tissues at the tips (or pads) of our fingers and toes also contains sensitive nerve endings. These enable the fingers and toes to process sensations like 'touch'. The nail acts as the vehicle for sensory input when contact is made between these portions of the body and other sources. Nails also provide support to these tissues. Without fingernails, we would struggle to be able to grasp or pick up objects or even have a good scratch.

Fingernails and toenails are discussed further in more detail on Schedule C attached hereto.

II. THE NEED FOR SKIN CARE

Hundreds of skin conditions can affect us. Skin conditions contribute 1.79% of the global burden of disease worldwide, and about 2% of total global disease disability (as measured in disability-adjusted life years).

A. Skin Diseases.

The American Academy of Dermatology Association reports that 1 in 4 people in the United States have a skin disease, one American in four sought treatment for at least one skin ailment, and the average person was treated for 1.6 skin diseases. Nearly half of Americans over age 65 have skin diseases, with an average of 2.2 each.

Skin cancer is the most common form of cancer in the United States; more than 3.5 million skin cancers are diagnosed yearly in this country. According to the World Health Organization, one in every five Americans will develop skin cancer in their lifetime. Treatment of skin disorders accounted for $75 billion in medical, preventative, and prescription and non-prescription drug costs.

Skin diseases are important because they are common, impose a huge economic and psychological burden on patients, and can be serious, even deadly. For example, the threat of malignant melanoma is well-known, but non-melanoma skin cancer also causes or contributes to significant morbidity and mortality. Moreover, common skin diseases such as psoriasis are associated with serious medical conditions including heart disease and diabetes. Infections are another common problem.

Selected skin conditions and diseases are discussed further in more detail on Schedule D attached hereto.

Causes of Skin Diseases. Skin diseases have a wide range of causes. Although most originate in the layers of the skin, such abnormalities are often important factors in the diagnosis of a variety of internal diseases. There is some truth in the belief that the skin mirrors a person's internal health. Often, the visibility and accessibility of skin make it the first organ of the body to show detectable signs of underlying disease. Abnormalities of the skin frequently suggest metabolic, malignant, and glandular diseases.

The inventor recognizes that Skin Abnormalities that are Often Important Factors in the Diagnosis of a Variety of Internal Diseases. Your skin can be a window to your health, given that many underlying conditions, some of which are very serious, first appear as skin problems.

Selected skin abnormalities that are often important factors in the diagnosis of a variety of internal diseases are discussed further in more detail on Schedule E attached hereto. A summary of the different kinds of skin injuries follow:

Skin Burns. There are three levels of burns: first-degree, second-degree, and third-degree. All types of skin burns can be painful and produce visible symptoms. Understanding the kind of burn and its severity is essential when assessing medical treatment.

A large proportion of burn injuries, both minor and serious, occur in the home, where eighty percent (80%) of the victims are children in the 1 to 16 age group. Other categories of concern in the home are the elderly and disabled, while in industry, electricians and workers in the chemical, refinery, and catering industries.

Burns over about ten percent (10%) or more of the body area are serious and may produce severe shock. For assessment purposes, the area burnt is more significant than the depth of the burn. In addition, on average, burned children become shocked more quickly than adults.

A further discussion of types of skin burns is set forth on Schedule F attached hereto.

Skin Punctures: Puncture Wounds and Cuts. A puncture wound is a forceful injury caused by a sharp, pointed object that penetrates the skin, such as a nail or a jagged piece of metal or wood. A puncture wound is usually narrower and deeper than a cut or scrape, and may be deep, smooth, or jagged. A puncture wound or cut, also called a laceration, often appears to be on the surface but may extend into the deeper tissue layers. A deep cut can affect tendons, muscles, ligaments, nerves, blood vessels, or bone. Many people accidentally get puncture wounds with household or work items, yard tools, or when operating machinery.

Gunshot Wounds. Gunshot wounds, particularly entry wounds, are puncture wounds. They are seldom stitched because infection is possible. Exit wounds, on the other hand, are often gaping holes and torn flesh which need to put back together with staples and stitches followed by antibiotic treatment.

Knife Wounds. Knives cause more disabling injuries than any other type of hand tool. Knives represent an important source of morbidity and mortality to people of all ages.

An estimated 8,250,914 knife-related injuries were treated in U.S. Emergency Departments from 1990 to 2008, averaging 434,259 injuries annually, or 1,190 per day. The injury rate was 1.56 injuries per 1000 U.S. resident population per year. Fingers/thumbs (66%; 5,447,467 of 8,249,410) were injured most often, and lacerations (94%; 7,793,487 of 8,249,553) were the most common type of injury. Pocket/utility knives were associated with injury most often (47%; 1,169,960 of 2,481,994), followed by cooking/kitchen knives (36%; 900,812 of 2,481,994). Children were more likely than adults to be injured while playing with a knife or during horseplay. One percent of patients were admitted to the hospital, and altercation-related stabbings to the trunk accounted for 52% of these admissions.

A further discussion of types of skin puncture wounds and cuts is set forth on Schedule G attached hereto.

Skin Bruising/Contusions. Skin bruises, also called contusions, occur when trauma damages or ruptures tiny blood vessels beneath the skin. Skin bruises are a normal response to an injury or trauma such as a fall, a cut, or bumping into something hard such as furniture, but may be the result of a more serious problem such as disease or intentional abuse.

A further discussion of types of skin bruising/contusions is set forth on Schedule G-1 attached hereto.

Plastic Surgery and Cosmetic Surgery.

Plastic Surgery: Focused on Repairing Defects to Reconstruct a Normal Function and Appearance. Plastic surgery is defined as a surgical specialty dedicated to reconstruction of facial and body defects due to birth disorders, trauma, burns, and disease. Plastic surgery is intended to correct dysfunctional areas of the body and is, by definition, reconstructive in nature. While many plastic surgeons choose to complete additional training and perform cosmetic surgery as well, the basis of their surgical training remains reconstructive plastic surgery. In fact, in 1999, the American Society of Plastic and Reconstructive Surgeons changed its name to the American Society of Plastic Surgeons to more strongly communicate the message that "plastic and reconstructive surgeons are one in the same."[1]

Cosmetic Surgery: Focused on Enhancing Appearance. The procedures, techniques, and principles of cosmetic surgery are entirely focused on enhancing a patient's appearance. Improving aesthetic appeal, symmetry, and proportion are the key goals. An aesthetic surgery can be performed on all areas of the head, neck, and body. Since cosmetic procedures treat areas that function properly, cosmetic surgery is designated as elective. Cosmetic elective procedures are performed by doctors from a variety of medical fields, including plastic surgeons.

Any licensed physician can legally perform cosmetic surgery, regardless of how they received cosmetic surgery training.

A further discussion of plastic surgery and cosmetic surgery is set forth on Schedule H attached hereto.

Dermatology

Dermatology is the branch of medicine concerned with the diagnosis and treatment of skin disorders, including the hair and nails, and some cosmetic problems. A dermatologist is a specialist doctor that manages diseases, in the widest sense, and some cosmetic problems of the skin, hair and nails.

There is currently a Shortage in the United States of Dermatologists; Average Wait Time in the United States for a Dermatologist Appointment Over 30 Days. The United States has been experiencing a national shortage of dermatologists for more than a decade. A study published by the Journal of the American Medical Association reported fewer than 3.4 dermatologists for every 100,000 people.[1] An average American dermatology appointment wait is 32.3 days. To see a family doctor, the wait time is 29.3 days on average. This means, if you have a standard HMO plan and suspect a cancerous mole on your skin, you will have to wait on average 61.6 days (2 months) to get it checked out.[2]

[1] https://en.wikipedia.org/wiki/Dermatology.
[2] https://www.firstderm.com/appointment-wait-time-see-dermatologist/#:~:text=Average%20wait%20times %20for%20an%20appointment%20with%20a, 10%20New%20York%3A%2015%20days%20More%20items . . . %20.

An October 2021 article published in Pediatric Dermatology[3] stated that 30% of pediatric primary care visits include a cutaneous complaint, yet the pediatric dermatology workforce has historically been too small to provide adequate specialized care. Only 336 pediatric dermatologists were identified in the United States, and nearly all of them (96.4%) were located in an urban area. The average number of dermatologists per state was 6.6; however, there are seven states with no pediatric dermatologist.

[3] https://doi.org/10.1111/pde.14824.

Current Standard Dermatologist Office Appointment: Full Body Skin Exam or Focus Only on An Area of Skin Important to You. Current standard skin exams begin in the dermatologist's office with some questions and paperwork. You are typically asked to answer questions or fill out a form, providing information about your general health, any medicines you take, skin problems you have, and your family medical history. Asking these routine questions is necessary to establish background information that really does matter.

Total Body Skin Examination. Background complete, for what is often referred to as a full body check, full skin exam, total body skin examination, or skin cancer screening, you will need to remove your clothes and put on a medical exam gown.[4] The total body skin examination ("TBSE") is considered the dermatologist's most important physical exam tool.[5] It is unlikely you will be told to remove your underwear, unless you have indicated that a spot on your genitalia concerns you. Your dermatologist will thoroughly check your skin from head to toe, paying close attention to hard-to-see spots like your scalp, back and buttocks, behind your ears, and even between your toes. This head-to-toe examination is one using the dermatologist's skill and expertise to evaluate your skin.[6]

[4] https://www.connollyskincare.com/connolly-skin-care/what-to-expect-full-skin-exam-skin-cancer/.
[5] https://www.aad.org/dw/dw-insights-and-inquiries/2019-archive/november/dwii-11-13-19-the-naked-truth-about-total-body-skin-examination-a-lesson-from-goldilocks-and-the-three-bears
[6] https://www.connollyskincare.com/connolly-skin-care/what-to-expect-full-skin-exam-skin-cancer/

In examining your skin your dermatologist may utilize a small handheld magnifying device called a dermatoscope that visualizes the outer surface of the skin (the epidermis) and the layers just beneath it.[7]

[7] https://www.skincancer.org/early-detection/annual-exams/.

Your dermatologist may biopsy one or more suspicious spots. This usually means you will receive a small local anesthetic injection to numb the area, and a small part or all of the lesion is removed and sent to a lab for analysis by a pathologist. If the report comes back that the spot is skin cancer, your physician will contact you and explain the type of skin cancer and treatment options.[8]

[8] https://www.skincancer.org/early-detection/annual-exams/.

A further discussion of a TBSE is set forth on Schedule I attached hereto.

Issues Related to Current Standard Dermatologist Office Total Body Skin Examination (TBSE). Regrettably, the techniques and reproducibility of total body skin examinations are not standardized, though TBSE methods seem to have been endearingly apprenticed behind closed doors to generations of dermatology trainees, without much in the way of practical teaching modules, examination logs, or live board certification proficiency.[9]

[9] https://www.aad.org/dw/dw-insights-and-inquiries/2019-archive/november/dwii-11-13-19-the-naked-truth-about-total-body-skin-examination-alesson-from-golilocks-and-the-three-bears.

Depending on a patient's body surface area, mobility, willingness to disrobe, and adornments, multiple factors may restrict full view of a patient's skin. For instance, some patients refuse a gown or removal of certain clothing items (e.g., undergarments, socks, wigs), and based on a recent cross-sectional study, if the patient has never had a TBSE, they are less willing to have "sensitive areas" of the body examined by a provider of the opposite gender. The recent cross-sectional study also, nonetheless, reported that 84% of patients expected genital and breast examination during a TBSE, but most did not feel as though they required a chaperone in the room.[10]

[10] https://www.aad.org/dw/dw-insights-and-inquiries/2019-archive/november/dwii-11-13-19-the-naked-truth-about-total-body-skin-examination-a-lesson-from-goldilocks-and-the-three-bears.

Issues Related to Frequency of a Standard Dermatologist Office Total Body Skin Examination (TBSE). High risk patients, namely those with history of skin cancer, immunosuppression, indoor tanning, and/or many blistering sunburns, as well as several other genetic parameters, would benefit most from at least a yearly TBSE.[11]

[11] https://www.aad.org/dw/dw-insights-and-inquiries/2019-archive/november/dwii-11-13-19-the-naked-truth-about-total-body-skin-examination-a-lesson-from-goldilocks-and-the-three-bears.

There are patients, however, who want to be seen "too often," some of whom are seen "too little," and others who seem "just right."[12] The age-old

[12] https://www.aad.org/dw/dw-insights-and-inquiries/2019-archive/november/dwii-11-13-19-the-naked-truth-about-total-body-skin-examination-a-lesson-from-goldilocks-and-the-three-bears. dilemma of balance, namely that of time, risk-based resource management, and patient preference, shapes each clinical day.[13]

[13] https://www.aad.org/dw/dw-insights-and-inquiries/2019-archive/november/dwii-11-13-19-the-naked-truth-about-total-body-skin-examination-a-lesson-from-goldilocks-and-the-three-bears.

In the U.S. currently, dermatologist density is 3.4 per 100,000 people, a ratio that cannot undertake mass screening of all Americans in a particular age range like mammography and dental screenings do. In an ideal universe, the aforementioned high-risk groups would receive expedited screening, but the Goldilocks scenario applies; no one eats the porridge at the perfect temperature all the time. No practice or patient population is comparable with respect to its risk factors, geography, medical care access, education, or expectations.[14]

[14] https://www.aad.org/dw/dw-insights-and-inquiries/2019-archive/november/dwii-11-13-19-the-naked-truth-about-total-body-skin-examination-a-lesson-from-goldilocks-and-the-three-bears.

Managing this balance includes many tactics and schedule permutations specific to each dermatologist's milieu. Most practices give patients with a history of melanoma priority status so that any visit cancellations or delays are rescheduled preferentially. Some of these at-risk patients, however, defer yearly TBSEs upon checkout and schedule an appointment only when a lesion of concern arises. In the opposite corner are those patients who deem the recommended total body skin examination interval as too infrequent, which poses a delicate dilemma and another cohort of risks, namely that the patient may become (or continue to be) overly fixated on the small details of every skin lesion, and develop the habit of expecting frequent and self-directed biopsies. This may lead to a difficult discussion about oversampling lesions and the potential for many scars, copious re-excisions for ambiguous lesional pathology, and a trend away from prudent clinical care. In addition, multiple visits incur more patient co-pays and absence from school, work, or home. Most dermatologists therefore advise all patients to call for a more acute visit if there is a lesion of concern and also recommend taking home photographs. Further, self- or partner-examination between visits is an intuitively valuable screening adjunct.[15]

[15] https://www.aad.org/dw/dw-insights-and-inquiries/2019-archive/november/dwii-11-13-19-the-naked-truth-about-total-body-skin-examination-a-lesson-from-goldilocks-and-the-three-bears.

Moreover, throwing a wider net for screening leaves no availability for dermatologists to care for other skin conditions or allow acute visit slots for worrisome evolving lesions.[16]

[16] https://www.aad.org/dw/dw-insights-and-inquiries/2019-archive/november/dwii-11-13-19-the-naked-truth-about-total-body-skin-examination-a-lesson-from-goldilocks-and-the-three-bears.

Bottom Line: A total body scan examination is the bedrock of dermatologic cancer screening, but its methods and frequency are yet to be standardized into agreed-upon guidelines.[17]

[17] https://www.aad.org/dw/dw-insights-and-inquiries/2019-archive/november/dwii-11-13-19-the-naked-truth-about-total-body-skin-examination-a-lesson-from-goldilocks-and-the-three-bears.

Focus Only on An Area of Skin Important to You. Depending on the reason for your appointment, your dermatologist may perform an examination on just the area of skin that is of concern to you. As a general rule, people see a dermatologist only when they or their primary care physician have reason to suspect that they have a dermatological disease or condition. This means that many people do not develop a long-standing relationship with a dermatologist unless they have a chronic condition.

Use of Ultrasound Imaging in Dermatology. Ultrasound imaging is frequently used for a safe and non-invasive window into the body's workings. During the past 30 years it has become an important tool in dermatology, and its applications continue to grow. This imaging technique can allow and is used for the study of the skin, the nail, and even the hair.

Ultrasonography is also used in animal dermatology, for example in cats.

There are generally 2 basic types of ultrasonography with dermatologic applications:
 (i) 20-MHz scanning, which can be used to measure tumor thickness and/or skin thickness when treating inflammatory diseases such as scleroderma or psoriasis; and
 (ii) Real-time sonography with 7.5- to 10-MHz probes used to search for and image lymph nodes and subcutaneous tumors in a variety of clinical settings, including preoperative staging and follow-up of melanoma.

Practically speaking, 20-25-MHz ultrasound allows for imaging of both the epidermis and the dermis.

Ultrasonography is capable of revealing the 3-dimensional size and outline of subcutaneous lesions, for example, lymph nodes, subcutaneous tumor masses or hematomas, and their relation to adjacent vessels. information about the lesion quality (solid, cystic, and combined) and the inner structure (homogeneous, inhomogeneous, hypoechoic, hyperechoic, calcification foci, and necroses) can be obtained. All this information can be combined to help distinguish between benign and malignant lymphadenopathy and to determine the malignant potential of a subcutaneous lesion. In addition to conventional B-mode sonography, newer ultrasound techniques such as native and signal-enhanced color Doppler sonography can be used to assess peripheral lymph nodes.

A. Use of Ultrasound and AI for Fully Automated Framework for Epidermal Layer Segmentation in Different Skin Diseases Based on 75 MHz High-Frequency Ultrasound (HFUS) Image Data.

Epidermis segmentation is a vital first step to detect changes in thickness, shape, and intensity and therefore support diagnosis and treatment monitoring in inflammatory and neoplastic skin lesions.

Using the architecture of the invention, AI software known to those skilled in the art is used to detect the appropriate region of interest, while additional AI software known to those skilled in the art is used in the main segmentation procedure.

B. Ultrasound Patches.

Presently, typically, in order to capture ultrasound insightful images, trained technicians manipulate ultrasound wands and probes to direct sound waves into the body. These waves reflect back and are used to produce high-resolution images.

Ultrasound imaging has typically required bulky and specialized equipment. New designs, however, wired and wireless, make ultrasound imaging as wearable and accessible as buying Band-Aids at the drugstore (the "Ultrasound Patch"). The Ultrasound Patch, which a medical professional or the Subject can affix to a specific area or areas of interest on the Subject's body, and connect directly to instruments that can translate the reflected sound waves into images or, for example, wirelessly connect with a smartphone or similar device where (i) AI algorithms can analyze the images, or (ii) the smartphone can through its transceiver send the data to a cloud where AI algorithms in the cloud can analyze the images.[18]

[18] See, for example,https://scitechdaily.com/mit-engineers-develop-ultrasound-stickers-that-can-see-inside-the-body/. See also https://www.science.org/doi/10.1126/science.abo2542. See also https://www.eurekalert.org/news-releases/959720.

Using an Ultrasound Patch allows for and assists in clinical diagnosis of skin issues at a distance as described in the instant invention, as well as for comparing skin issues over time (for example, are they improving or worsening) at a distance as described in the instant invention.

Issues Related to Skin-Related Biopsies: Physical Skin Markers. As earlier generally discussed, a skin biopsy is a procedure to remove cells or skin samples from your body for laboratory examination. A dermatologist uses a skin biopsy to diagnose skin conditions and remove abnormal tissue.

A brief description of the three main types of skin biopsies is set forth in Schedule J attached hereto.

The dermatologist or nurse then cleans the area of the skin to be biopsied. Your skin may be marked to outline the biopsy area, and you then receive a medication (local anesthetic) to numb the biopsy site.

After the biopsy is complete, your dermatologist sends the skin biopsy sample to a laboratory for testing. Results may take several days or longer, sometimes up to months, depending on the type of biopsy and the lab's procedures.

Healing of your biopsy wound can take several weeks, but is usually complete within two months. Wounds on the legs and feet tend to heal slower than those on other areas of the body.

Lab results may take several days or longer, sometimes up to months, depending on the type of biopsy and the lab's procedures.

If your results were normal, it means no cancer or skin disease was found. If your results were not normal, you may be diagnosed with one of the following conditions:

A bacterial or fungal infection.

A skin disorder such as psoriasis.

Skin cancer. Your results may indicate one of three types of skin cancers: basal cell, squamous cell, or melanoma.

For certain results, follow-up surgery may be required.[19]

[19] https//www.mayoclinic.org/tests-procedures/skin-biopsy/about/pac-20384634; https://medlineplus.gov/lab-tests/skin-biopsy/.

Skin Marker Issues. A simple measure to support a patient's safety and to avoid wrong site surgery is preoperative skin marking.

As earlier discussed, in performing the biopsy your dermatologist or nurse cleans the area of the skin to be biopsied. Your skin may be marked to outline the biopsy area.

The problem arises when due to the type of marker used (a) it is not sterile, or (b) the marking made by it is not visible after (i) disinfection of the surgical field, or (ii) healing of the biopsy area (which may occur before a subsequent surgery is required, leaving the surgeon to struggle to locate the site for surgery).[20] Some of same issues arise for surgeons who pre-surgery mark the outline of the surgery area.

[20] https://www.ncbi.mln.gov/pmc/articles/PMC6785962ffsec1-3title. See also *Surgical Site Markers: Putting Your Mark on Patient Safely, Pennsylvania Patient Safety Authority*, Vol. 5, No. 4, December 2008.

Exception for Breast Biopsies. Interestingly, for breast biopsies (but not other types of skin biopsies), no matter the type of imaging utilized to guide the breast biopsy, the current standard of care at the completion of the biopsy is placement of a physical biopsy marker.

A discussion of breast biopsies and the tiny physical clips used to identify the biopsy site are set forth on Schedule K attached hereto.

Teledermatology[21]

[21] https://miiskin.com/dermatology/whitepaper-teledermatology-benefits-types-implementation/.

One partial solution to the long wait times in the United States to meet with a dermatologist in-person for a skin examination is teledermatology.

Teledermatology is the term commonly used for telehealth (telemedicine) carried out in dermatology, and it covers the delivery of dermatology care through modern electronic or digital forms of communication.[22] Teledermatology is a form a form of dermatological practice in which telecommunication technologies are used to exchange medical information and treatment through audio, visual, and data communication, including photos of dermatologic conditions, between dermatologists and non-dermatologists who are evaluating patients, along with dermatologists who are evaluating patients directly with patients via distance.[23]

[22] https://miiskin.com/dermatology/whitepaper-teledermatology-benefits-types-implementation/.

[23] https://en.wikipedia.org/wiki/Dermatology.

Teledermatology is one of the areas of telehealth that is most developed because most skin diseases are visible and can be photographed or filmed for a healthcare provider, such as a dermatologist, for remote diagnosis, assessment, and management recommendations.[24]

[24] https://miiskin.com/dermatology/whitepaper-teledermatology-benefits-types-implementation/.

Teledermatology has evolved through the decades and has been used for various purposes ranging from triage to diagnostics.

Due to the visual nature of many skin conditions, teledermatology can be a valuable tool for those who need to be seen by a dermatologist, but do not have ready access to one. Additionally, teledermatology can often be utilized to monitor or follow-up with patients who have certain chronic conditions, in order to ensure that their treatment plan is working effectively.[25]

[25] https://clearlyderm.com/what-is-teledermatology/.

Overview of the Use of Teledermatology by the U.S. Military. Beginning in the year 2,000, the U.S. military launched a full-scale teledermatology program within the U.S. Army that served deployed soldiers abroad along with service members and their families across the United States. From then until now, the U.S. Army has completed more than 50,000 consultations in more than 50 countries.[26]

[26] https://www.aad.org/skinserious/stories-hon-pak.

It is well documented that non-life-threatening skin disease comprises the majority of specialty care requests in U.S. military deployed settings. Thus, teledermatology has become and is a critical resource in military operational medical settings.[27]

[27] https://www.aad.org/skinserious/stories-hon-pak.

Although the U.S. Army Knowledge Online telemedicine platform has shown and shows promise for improving routine domestic dermatology care, it should be noted that the U.S. military had and has a few distinct advantages with respect to telemedicine. Military physicians, for example, are not bound by state-to-state licensing requirements, and did and do not need to worry about telemedicine reimbursement because they are salaried.[28]

[28] https://www.aad.org/skinserious/stories-hon-pak.

Current State of Teledermatology in the United States. The COVID-19 pandemic of 2020-2021 quickly illuminated specific applications of teledermatology. Increased reliance on teledermatology during the COVID-19 pandemic not only helped patients avoid contracting infection, but it also gave dermatologists a better understanding of how to best employ the technology in daily practice.[29]

[29] https://www.msn.com/en-us/news/technology/using-a-mix-of-new-technologies-teledermatology-is-changing-how-dermatologists-provide-care-during-the-pandemic/ar-AAOw4El?ocid=uxbndlbing.

Benefits of Teledermatology. In the era of smartphones and the ease with which you can photograph the skin, online dermatology is one of the areas in medicine that can potentially benefit from innovative telehealth implementations.[30]

[30] https://miiskin.com/dermatology/whitepaper-teledermatology-benefits-types-implementation/.

In the right setting and context, diagnosis and disease management can be facilitated through teledermatology. It can be a cost-effective approach to pre-screen patients and determine which patients need to be seen in person and which patients can be prescribed new treatment without a physical visit.[31]

[31] https://miiskin.com/dermatology/whitepaper-teledermatology-benefits-types-implementation/.

Accordingly, teledermatology can facilitate increased patient convenience, access to care if a physical visit is not possible, reduce wait times, make scheduling of dermatologists more flexible, and lower healthcare costs.[32] It can also allow dermatologists to treat minor conditions online while serious conditions requiring immediate care are given priority for appointments.[33]

[32] https://miiskin.com/dermatology/whitepaper-teledermatology-benefits-types-implementation/.
[33] https://en.wikipedia.org/wiki/Dermatology.

Patients with chronic diseases such as eczema, acne, and psoriasis often require many follow-up visits for complex treatments, and some of these follow-up visits could occur remotely.[34]

[34] https://miiskin.com/dermatology/whitepaper-teledermatology-benefits-types-implementation/.

Participants in Teledermatology. With regard to the participants in a consultation, primary teledermatology covers direct communication between a patient and a healthcare provider such as a dermatologist. Secondary teledermatology describes communication between healthcare providers. For instance, a general practitioner may request a specialist consultation from a dermatologist in secondary teledermatology. Lastly, tertiary teledermatology refers to a telehealth collaboration between dermatologists, often to seek a second opinion or to obtain consensus.

Teledermatology Modes of Communication. In the different modes of teledermatology, transfer of audio and visual information along with patient data (such as patient-reported information or data from the patient's electronic health record) can be utilized.

A further discussion of teledermatology modes of communication is set forth on Schedule L attached hereto.

Telehealth and Dermatology Guidelines. Organizations, such as the American Medical Association, American Academy of Dermatology, and the British Association of Dermatologists, have published guidelines for telehealth and teledermatology. There are likely similar guidelines in most other countries.

Skin Cancer Apps and Cancer Detection in 2021.[35] In recent years there has been exciting research into how imagery can be used for managing the risks of skin cancer and assessing individual lesions for melanoma.

[35] https://miiskin.com/dermatology/whitepaper-teledermatology-benefits-types-implementation/.

Smartphone apps, downloaded for iPhone and Android, which are designed to assist people worried about skin cancer, popularly known as "skin cancer apps", have been on the rise in recent years.

As smartphone cameras have improved and become widespread, some companies have released skin cancer scanning apps into the app stores to purportedly diagnose skin cancer.

Some Artificial Intelligence ("AI") research has shown promising results for melanoma risk assessments on lesions from magnified photos taken in clinical contexts—also called digital dermoscopy.[36]

[36] Dermoscopy, also called dermatoscopy, skin surface microscopy, or epiluminescence microscopy, is a non-invasive technique of investigating skin lesions that help professionals in cancer examinations. Digital dermoscopy is considered to be the preferred approach due to its correctness and accuracy in results.

It appears that the Federal Drug Administration in the United States (FDA) has, as of the writing of this document, not approved any apps that offer an algorithmic assessment, and for now, apps with an explicit skin cancer detection element should be treated with caution.[37]

[37] https://miiskin.com/dermatology/whitepaper-teledermatology-benefits-types-implementation/.

Google's "Derm Assist"[38] Google has an AI-powered dermatology assist tool called "Derm Assist", which is a web-based application Google hopes to launch as a pilot sometime in 2021.[39] The goal of Derm Assist is said to be to help

[38] https://blog.google/technology/health/ai-dermatology-preview-io-2021/.
[39] https://blog.google/technology/health/ai-dermatology-preview-io-2021/. consumers get more information about skin conditions in order to plan their next steps. Based on three camera images from different angles, and responses to a survey about symptoms, the app should analyze the information, compare it with a large database of images of 288 conditions, and provide the user with a list of possible skin conditions. Google says that the tool is not intended for diagnosis and does not replace a doctor's advice, but rather hopes it will someday be able to help dermatologists, general medical practitioners, and other healthcare professionals in the accuracy of their own assessments.[40]
[40] https://blog.google/technology/health/ai-dermatology-preview-io-2021/.

Novel Services. In recent years, novel services through which people send smartphone photos to a local dermatologist or specialist have shown positive results as a way to bring the possibility of skin cancer to consumers' attention and to promote early presentation to a doctor. Such services are now available in some markets where skin cancer is most prevalent. Even though they often involve a dermatologist, they communicate that the service is not an explicit diagnostic tool for skin cancer, but as a way to sound an early alarm about a suspicious skin lesion. Such dermatology telehealth services will, therefore, recommend that consumers seek out additional medical advice about their skin concern.[41]

[41] https://miiskin.com/dermatology/whitepaper-teledermatology-benefits-types-implementation/.

Common Current Use of Physical Skin Markers

Currently, physical "skin markings" made by health care professionals on the skin of patients are commonly used in a broad range of medical practice areas. These include, without limitation, allergy testing, radiation treatment, skin biopsies, and general surgery.

A description of physical skin markings commonly currently used in allergy testing, radiation treatment, skin biopsies, and general surgery is set forth on Schedule M attached hereto.

Physical Skin Marker Shortcomings

Physical Skin Marker Issues. Problems with physical skin markers arise, without limitation, when due to the type of marker used (a) it is not sterile, (b) the marking made by the marker is not visible after disinfection of the surgical field, (c) the physical clip marker of the type used in breast biopsies migrates, or (d) healing of the biopsy or surgery area (which may occur before a subsequent surgery is required, leaving the surgeon to struggle to locate the site for surgery).

Biometrics

Biometric identifiers fall into two categories: physical identifiers and behavioral identifiers. Physical identifiers are, for the most part, immutable and device dependent.

Every individual is physically unique, even identical twins. Biometric technology differentiates these unique characteristics to confirm identity and improve security.

Biometrics use a set of recognizable and verifiable data unique and specific to that person. They use our most unique physical characteristics to serve as digital identifiers that computers and software can interpret and utilize for identity-related applications. They can be used to identify someone in a biometric database or to verify the authenticity of a claimed identity.

Fingerprint Recognition. Fingerprint recognition, which measures a finger's unique ridges, is one of the oldest forms of biometric identification. After capturing the print, sophisticated algorithms use the image to produce a unique digital biometric template. The template is then compared to new or existing scans to either confirm or deny a match.

Fingerprint scanners have become ubiquitous in recent years due to their widespread deployment on smartphones. Any device that can be touched, such as a phone screen, computer mouse or touchpad, or a door panel, has the potential to become an easy and convenient fingerprint scanner.

Facial Recognition. Facial recognition, by far the oldest form of biometric authentication, is the process of identifying or verifying the identity of a person using their face. It captures, analyzes, and compares patterns based on the person's facial details.

Stated another way, facial recognition is a way of using software to determine the similarity between two face images to evaluate a claim. It uses computer-generated filters to transform face images into numerical expressions that can be compared to determine their similarity. These filters are usually generated by using deep "learning," which uses artificial neural networks to process data.

The data about a face is called a face template or faceprint, and is distinct from a photograph because it is designed to only include certain details that can be used to distinguish one face from another. These face templates/faceprints are stored in a face recognition database. If you enter a photo (or data about a face) into the database, it will locate any matching face template/faceprint it has stored. Facial recognition systems can be used to identify people in real-time.

Face Capture. This process, known to those skilled in the art, transforms analog information (a face) into a set of digital information (data or vectors) based on a person's facial features.

Face Detection. This process, known to those skilled in the art, is essential in detecting and locating human faces in images and video.

Face Match. This process, known to those skilled in the art, verifies if two faces belong to the same person.

As known to those skilled in the art, software can automate the capture of facial images and analyze streaming video frames in real time. Image capture can be automatically triggered once focus, facial positioning, lighting and other image-capturing details are verified for compliance with quality standards. The image can be analyzed again and optimized post-capture. Automatic scaling, rotation, cropping, brightness, and contrast enhancements optimize the quality of an otherwise non-compliant image so the photo does not have to be retaken.

In the past few years, artificial intelligence and machine learning algorithms have become the predominant methods for automatically extracting the above information and then comparing it against other images. These algorithms enhance the biometric security of face recognition technology without having any impact on the user experience.

In 2014 the GaussianFace algorithm developed by researchers at The Chinese University of Hong Kong achieved facial identification scores of 98.52% compared with 97.53% achieved by humans.

In 2014 Facebook announced its DeepFace program, which can determine if two photographed faces belong to the same person, with an accuracy rate of 97.25% compared with 98.52% achieved by humans.

In June 2015 Google's FaceNet, on the widely used Labeled Faces in the Wild (LFW) dataset, achieved an accuracy of 99.63%.

Face biometrics are a preferred biometric benchmark because face detection and face match processes for verification/identification are speedy and easy to deploy and implement. Also, face biometrics are a preferred biometric benchmark because there is no physical interaction with the end-user.

Nearly all smartphones, tablets, and laptops have built-in front-facing cameras that enable high-quality "selfie" shots, making it convenient to collect a live facial recognition sample for comparison against a template. Facial image capture using the front-facing camera on a smartphone similar device can be performed passively, during capture of other modalities such as voice to improve matching performance.

Skin Pores, Hair Follicles, and Hair. Skin pores are the tiny openings in the skin and they are found all over the human body except for the palms of the hands, soles of the feet, mucous membranes, and lips. All mammals have them. The medical term for a skin pore is a hair follicle. Although "follicles" and "pores" are often used interchangeably, a pore is simply the opening of a hair follicle that extends downward through several layers of skin.

A hair follicle anchors each hair into the skin. The hair bulb forms the base of the hair follicle. The part of a hair that is visible above the skin surface is the hair shaft. It consists of dead cells.

Surprisingly, humans have as many hair follicles on their bodies as their closest relative, the chimpanzee. However, humans do not appear hairy like chimpanzees since their hair follicles often contain small unpigmented fibers termed vellus hairs, rather than large, pigmented hair fibers which are known as terminal hairs. On humans, these terminal hairs are limited to restricted body sites such as pubic areas, the face, and the scalp.

In human skin, individual hair follicles are organized into follicular units that each contain 2-5 hair follicles. Despite there being multiple follicles per unit, all the hair fibers produced in these units exit through a single pore at the skin surface. Each of these follicular units is also connected to just one erector pili muscle (which is a small fan-shaped smooth muscle, associated with the base of each hair, which contracts when the body surface is chilled, or as a reaction to a person's fear, and it erects the hair at its base, and produces the appearance of goose bumps), which connects the follicles at the level of their bulge to the basement membrane of the skin epidermis.

Hair is a unique feature of each individual and, more generally, of the human species. It is estimated that human adults each have about 5 million hair follicles, with around 1 million hair follicles found on the head and only 120,000 to 150,000 hair follicles covering the scalp. Depending on the region of the scalp, their density varies by 200 to 300 follicles/cm2. Skin pore size is genetic; one cannot shrink them or make them go away. Accordingly, similar to fingerprint patterns, skin pore or hair follicle patterns are a unique identifier of each person, including selected areas of each person's skin.

Blood Veins. Veins are blood vessels that carry and return deoxygenated blood from tissues and organs back to the heart. The venous system refers to the network of veins that work to deliver deoxygenated blood back to your heart. Veins are superficial, and there are literally many millions of them, especially at the microscopic and near-microscopic level. The smallest blood vessels measure only five micrometers. For perspective, a strand of human hair measures about 17 micrometers. Names are not given to most veins because they are too variable from one person to another.

Vein pattern is more-or-less constant in the early stages of human development (although even then it can vary microscopically). Thereafter, peripheral vasculature varies greatly while major vessels are mostly recognizable.

Commercial devices exist for detecting and visualizing blood veins without physical contact.

Blood Veins Are a Unique Feature of Each Individual. Each individual's vein map is unique, even in the case of identical twins. Processing the pattern of an individual's veins is not affected by race, skin discoloration, hair, age, or time.

Blood Veins May be Displayed Clearly on the Subject's Skin. Hemoglobin in the blood absorbs infrared light, which passes through the skin's surface, and under the infrared light the Subject's blood veins appear noticeably different than the surrounding tissue. The vasculature shows up clearly on the skin's surface. A special camera can capture the image. The captured image data can be digitized, and the digitized data either stored or used it to confirm identity. This process allows for blood vein pattern mapping in a contactless manner.

Thermography Recognition. Thermograms, generally, are visual displays of the amount of infrared energy emitted, transmitted, and reflected by an object, which are then converted into temperature, and displayed as an image of temperature distribution. It works very much like facial recognition, except that an infrared camera is used to capture the images.

Facial thermograms are unique to individuals, and facial thermograph technology capability is inherently more accurate and more robust over varying lighting and environment conditions than is the use of video images.

Biometric thermography captures heat patterns caused by moving blood beneath the skin. Because blood vessels are highly unique, corresponding thermograms are also unique—even among identical twins—making this method of biometric authentication even more accurate than traditional facial recognition software.

Thermograms as a mechanism of biometric identification are advantageous since the technology is non-intrusive. Infrared thermography is presently commonly used in medical imaging, including peripheral vascular disease, thyroid abnormalities, and metabolic and inflammatory condition monitoring.

As medical devices continue to decrease in size, heat generation and thermal dissipation become increasingly important. Thermal imaging microscopes measure and display the temperature distribution over the surface of small areas, and provide true temperature mapping, analyze thermal images, record thermal movies, and create temperature graphing and charting. Commercial products since 2018 exist that provide the following resolution: macroscopic, 80 µm/pixel spatial resolution, 20 µm/pixel spatial resolution, and 5 µm/pixel spatial resolution.

Storage of Captured Biometric Identifier Data

Local or Device-Based Authentication. The most common example of a local authentication mechanism is the hardware security module in a smartphone. User information—such as a fingerprint scan, facial image, or a voice print—is stored inside the module. When authentication is required, biometric information is collected by the fingerprint reader, camera or microphone and sent to the module where it is compared to the original. The module tells the phone whether or not the new information is a match to what it already had stored.

With this system, the raw biometric information is never accessible to any software or system outside the module, including the phone's own operating system. On the iPhone, this is called the secure enclave and is available on every phone with an Apple A7 chip or newer. The first phone with this technology was the iphone 5S, released in 2013. Similar technology is also available on Android phones. Samsung, for example, started rolling out the ARM TrustZone trusted execution environment with the Samsung S3 smartphone.

Today, smartphone hardware security modules are used to provide security for Apple Pay, Google Pay and Samsung Pay as well as to authenticate third-party applications. PayPal, for example, can use a phone's biometric sensor for authentication without PayPal ever seeing the actual biometric data itself. Square Cash, Venmo, Dropbox and many banking apps and password management apps leverage this authentication mechanism as well.

Enterprises can also use smartphone-based biometric readers whenever their users or customers have access to smartphones, without ever having to collect and store any identifying biometric information on their own servers. Similar technology is available for other types of devices, such as smart cards, smart door locks, or fingerprint scanners for PCs.

The Transfer of Captured Biometric Identifier Digital Data. Similar to all digital data, captured biometric identifier digital data can be easily transferred from one electronic storage data site to another, be it, without limitation, a cloud, edge storage, or the hardware security module in a smartphone other than the smartphone that initially stored the data.

Augmented Reality (AR) Augmented reality (AR) technology superimposes digital information onto our view of the real world. It augments the world around us with computer generated perceptual information.

AR takes real-world environments and then enhances these environments through computer-generated procedures that enrich the environment. AR can be defined as a system that incorporates three basic features: a combination of real and virtual worlds, real-time interaction, and accurate 3D registration of virtual and real objects. This experience is seamlessly interwoven with the physical world such that it is perceived as an immersive aspect of the real environment.

AR Vision. On the vision side of AR (as opposed to auditory or tactile/haptic interactions, either alone or combined with other forms of AR), the process, known to those skilled in the art, involves taking an image input, detecting markers/fiducials, and seamlessly transforming new images onto the scene.

AR vision may be achieved with heads-up displays, or using retinal scan displays, but generally to date these have been restricted to specialist applications. Augmented or mixed reality, however, can also be implemented on mobile devices with cameras.

Hardware components for augmented reality are typically a processor, display, sensors and input devices. Modern mobile computing devices like smartphones and tablet computers contain these elements, which often include a camera and microelectromechanical systems (MEMS) sensors such as an accelerometer, GPS, and solid state compass, making them suitable AR platforms.

AR Display. Various technologies are used in AR rendering, including optical projection systems, monitors, handheld devices, and display systems, which are worn on the human body.

Eyeglasses and/or Goggles. AR displays can be rendered on devices resembling eyeglasses. Versions include eyewear that employs cameras to intercept the real world view and re-display its augmented view through the eyepieces and devices in which the AR imagery is projected through or reflected off the surfaces of the eyewear lens pieces.

A variation of devices resembling eyeglasses for rendering AR displays is AR displays being rendered on devices resembling goggles.

Head-Up Display (HUD). A head-up display (HUD) is a transparent display that presents data without requiring users to look away from their usual viewpoints. A precursor technology to AR, heads-up displays were first developed for pilots in the 1950s, projecting simple flight data into their line of sight, thereby enabling them to keep their "heads up" and not look down at the instruments. Near-eye AR devices can be used as portable head-up displays as they can show data, information, and images while the user views the real world. Many definitions of AR only define it as overlaying the information. This is basically what a head-up display does; however, practically speaking, AR is expected to include registration and tracking between the superimposed perceptions, sensations, information, data, and images and some portion of the real world.

A head-mounted display (HMD) is a display device worn on the forehead, such as a harness or helmet-mounted. HMDs place images of both the physical world and virtual objects over the user's field of view. Modern HMDs often employ sensors for six degrees of freedom monitoring that allow the system to align virtual information to the physical world and adjust accordingly with the user's head movements.

Contact Lenses. Contact lenses that display AR imaging are in development. These bionic contact lenses might contain the elements for display embedded into the lens including integrated circuitry, LEDs and an antenna for wireless communication. The first contact lens display was patented in 1999 by Steve Mann and was intended to work in combination with AR spectacles, but the project was abandoned, then 11 years later in 2010-2011. Another version of contact lenses, in development for the U.S. military, is designed to function with AR spectacles, allowing soldiers to focus on close-to-the-eye AR images on the spectacles and distant real world objects at the same time.

At CES 2013, a company called Innovega also unveiled similar contact lenses that required being combined with AR glasses to work.

The first publicly unveiled working prototype of an AR contact lens not requiring the use of glasses in conjunction was developed by Mojo Vision and announced and shown off at CES 2020.

Handheld Display. A handheld display employs a small display that fits in a user's hand. All handheld AR solutions to date opt for video see-through. Initially handheld AR employed fiducial markers, and later GPS units and MEMS sensors such as digital compasses and six degrees of freedom accelerometer-gyroscope. Today simultaneous localization and mapping (SLAM) markerless trackers such as PTAM (parallel tracking and mapping) are starting to come into use. Handheld display AR promises to be the first commercial success for AR technologies. The two main advantages of handheld AR are the portable nature of handheld devices and the ubiquitous nature of camera phones. The disadvantages are the physical constraints of the user having to hold the handheld device out in front of them at all times, as well as the distorting effect of classically wide-angled mobile phone cameras when compared to the real world as viewed through the eye.

Games such as Pokémon Go and Ingress utilize an Image Linked Map (ILM) interface, where approved geotagged locations appear on a stylized map for the user to interact with.

Projection Mapping. Projection mapping augments real-world objects and scenes, without the use of special displays such as monitors, head-mounted displays or hand-held devices. Projection mapping makes use of digital projectors to display graphical information onto physical objects. The key difference in projection mapping is that the display is separated from the users of the system. Since the displays are not associated with each user, projection mapping scales naturally up to groups of users, allowing for collocated collaboration between users.

Examples include shader lamps, mobile projectors, virtual tables, and smart projectors. Shader lamps mimic and augment reality by projecting imagery onto neutral objects. This provides the opportunity to enhance the object's appearance with materials of a simple unit—a projector, camera, and sensor.

Other applications include table and wall projections. One innovation, the Extended Virtual Table, separates the virtual from the real by including beam-splitter mirrors attached to the ceiling at an adjustable angle. Virtual showcases, which employ beam splitter mirrors together with multiple graphics displays, provide an interactive means of simultaneously engaging with the virtual and the real. Many more implementations and configurations make spatial AR display an increasingly attractive interactive alternative.

A projection mapping system can display on any number of surfaces in an indoor setting at once. Projection mapping supports both a graphical visualization and passive haptic sensation for the end users. Users are able to touch physical objects in a process that provides passive haptic sensation.

AR Motion Tracking.

Tracking. Modern mobile AR systems use one or more of the following motion tracking technologies: digital cameras and/or other optical sensors, accelerometers, GPS, gyroscopes, solid state compasses, or radio-frequency identification (RFID). These technologies offer varying levels of accuracy and precision. The most important is the position and orientation of the user's head. Tracking the user's hand(s) or a handheld input device can provide a 6DOF interaction technique.

Computer. The computer analyzes the sensed visual and other data to synthesize and position augmentations. Computers are responsible for the graphics that go with AR. AR uses a computer-generated image which has a striking effect on the way the real world is shown.

As computers progress, AR will become more flexible and more common in society.

Computers are the core of augmented reality. The computer receives data from the sensors which determine the relative position of an objects' surface. This translates to an input to the computer which then outputs to the users by adding something that would otherwise not be there. The computer comprises memory and a processor. The computer takes the scanned environment then generates images or a video and puts it on the receiver for the observer to see. The fixed marks on an object's surface are stored in the memory of a computer. The computer also withdraws from its memory to present images realistically to the onlooker. The best example of this is of the Pepsi Max AR Bus Shelter.

Projectors. Projectors can also be used to display AR vision contents. The projector can throw a virtual object on a projection screen and the viewer can interact with this virtual object. Projection surfaces can be many objects such as walls or glass panes.

Software and Algorithms. A key measure of AR systems is how realistically they integrate augmentations with the real world. The software must derive real world coordinates, independent of camera, and camera images. That process, known as image registration, uses different methods of computer vision, mostly related to video tracking. Many computer vision methods of AR are inherited from visual odometry. An augogram is a computer generated image that is used to create AR. Augography is the science and software practice of making augograms for AR.

Usually those methods use two stages. The first stage is to detect interest points, fiducial markers or optical flow in the camera images. This step can use feature detection methods like corner detection, blob detection, edge detection or thresholding, and other image processing methods. The second stage restores a real world coordinate system from the data obtained in the first stage. Some methods assume objects with known geometry (or fiducial markers) are present in the scene. In some of those cases the scene 3D structure should be calculated beforehand. If part of the scene is unknown simultaneous localization and mapping (SLAM) can map relative positions. If no information about scene geometry is available, structure from motion methods like bundle adjustment are used. Mathematical methods used in the second stage include: projective (epipolar) geometry, geometric algebra, rotation representation with exponential map, kalman and particle filters, nonlinear optimization, robust statistics.

In AR, the distinction is made between two distinct modes of tracking, known as marker and markerless. Markers are visual cues which trigger the display of the virtual information. A piece of paper with some distinct geometries can be used. The camera recognizes the geometries by identifying specific points in the drawing. Markerless tracking, also called instant tracking, does not use markers. Instead, the user positions the object in the camera view preferably in a horizontal plane. It uses sensors in mobile devices to accurately detect the real-world environment, such as the locations of walls and points of intersection.

Augmented Reality Markup Language (ARML). Augmented Reality Markup Language (ARML) is a data standard developed within the Open Geospatial Consortium (OGC), which consists of Extensible Markup Language (XML) grammar to describe the location and appearance of virtual objects in the scene, as well as ECMAScript bindings to allow dynamic access to properties of virtual objects.

C. AR Audio.

AR audio, sometimes called "Hearables", is a fast growing area. For example, the tourist who, with phone in pocket, is relying on audio instructions from Google Maps to navigate a street in Los Angeles. It is arguable that listening to such audio directions is a pure form of AR audio. At least enough to qualify as a first broad use case. We already use audio AR, although we might not know it by that name.

Four components govern the process of Hearables: hardware, software, infrastructure, and mobile application.

1. Hardware. The hardware consist of printed circuit board, data processors, sensors, battery, antenna, and microphone array.
2. Embedded Software. Embedding a software within the Hearable can be achieved by communication between software and hardware through the instruction by a software engineer. These instructions include collection, processing, analyzing the data, transferring the information, and merging the solution with other devices.
3. Infrastructure. The back-end infrastructure includes the restoration, processing, and establishing of the data at the end-point devices, which can be done by developing the application logic.

4. Mobile Application. This provides access to settings and customization thus enabling users to access sensor data on their screen and conveniently manage the device.

One application of AR audio is an in-ear device for speech recognition. This type of device is governed by two components:

a. Language Identification System.

Language Identification System (LID) identifies a foreign language.

b. Automatic Speech Recognition.

Automatic Speech Recognition for converting the phonetic speech into words, which is achieved by the NLP algorithm. It translates a foreign language and provides two ways of translation into multiple languages simultaneously.

D. The Pokemon Go App.

The popular Pokemon Go app, launched in 2016, perhaps the biggest AR success story in recent years, is an example of computer vision-based augmented reality. Users open the app on their smartphone, which then accesses their camera.

Players then observe the world through their camera, walking through real-world environments, including city streets, tranquil parks, and crowded bars and restaurants. The Pokemon Go app places creatures (called Pokemon) inside this virtual world. Players then must capture these Pokemon and collect all of them.

E. AR is a Technology Whose Time has Arrived.

Conceived in rudimentary form as early as the 1960's, AR is only now becoming truly practical.

NFL football was one of the first to use AR commercially when they put the colored first down lines on the field that we could see with our TVs.

Recent advances in mobile processing, coupled with an explosion in digital storage capacity, ubiquity of wireless broadband connections, mass adoption of smart phones, and the limitless data store that the Internet has gathered provide all the prerequisites for this potentially game-changing technology. Consumer AR applications are already present on hundreds of millions of smart phones (utilizing built-in cameras, accelerometers, microphones, and GPS), and with the development of new AR-specific chipsets from major chip companies like Nvidia and QualComm, the AR pricepoint, and the bar for entry to potential AR app-developers will be lowered further.

Entire companies have been built surrounding AR and virtual reality applications, including Oculus and MagicLeap.

F. The AR Application and the Importance of Fiducial Markers.

The AR application is the computer program that orchestrates and controls different aspects of the augmented reality experience. An example of a very simple AR application is a simple AR browser. An AR browser might do something as simple as making it appear that a specific 3D object is placed on a specific fiducial marker (i.e., an object placed in the field of view of an imaging system that appears in the image produced, for use as a point of reference or a measure) placed in the real world. Tracking registration becomes even more important than the basic virtual reality object, due to the importance of mapping virtual information onto the real-world view. In high-resolution optical microscopy, fiducials can be used to actively stabilize the field of view. Stabilization to better than 0.1 nm is achievable. In physics, 3D computer graphics, and photography, fiducials are reference points: fixed points or lines within a scene to which other objects can be related or against which objects can be measured. Cameras outfitted with Réseau plates produce these reference marks (also called Réseau crosses) and are commonly used by NASA. Such marks are closely related to the timing marks used in optical mark recognition.

In applications of AR, fiducials help resolve several problems of integration between the real world view and the synthetic images that augment it. Fiducials of known pattern and size can serve as real world anchors of location, orientation, and scale. They can establish the identity of the scene or objects within the scene. For example, a fiducial printed on one page of an AR pop-up book would identify the page to allow the system to select the augmentation content. It would also serve to moor the coordinates of the augmented content to the three dimensional location, orientation, and scale of the open book, helping to create a stable and accurate fusion of real and synthetic imagery.

1. Fiducial Markers.

Fiducial markers such as, but without limitation, AprilTags are an integral part of many computer vision systems, including, but not limited to:

a. Camera calibration;
b. Object size estimation;
c. Measuring the distance between the camera and the object;
d. 3D positioning;
e. Object orientation;
f. Robotics (i.e., autonomously navigating to a specific marker);
g. And so on.

2. AR Application Versus Content Used Within the Application.

It is important to draw a distinction between the AR application and the content used within the application. When this distinction is executed skillfully, the same AR application can be used in many different contexts. For example, an AR application that places simulated sculptures in a real-world space for the purpose of teaching an art appreciation course could be re-purposed by using different content and using it to train soldiers regarding the kinds of landmarks they need to locate when they are deployed to a place they have not yet experienced in the real world.

The AR application also interacts with the various sensors, devices, and displays used in the experience. In actual practice, many of these lower level tasks are handled in AR libraries that are used by many different AR applications. One can even make AR visual content move dynamically in real time.

G. AR in Smartphones.

Smartphone chips are equipped with neural processing engines (known by other names, as well). These are targeted AI processors that make things such as Apple's Animjoi possible. Many more improvements and features made possible by these AR engines are expected to surface before the end of 2021.

H. AR and Real-Life Medical Care.

AR is just now beginning to find its way into real-life higher-stakes medical care.

"One example is the application Proximie [,] which allows a surgeon in one place to help a surgeon in another place. The remote surgeon guides the operating surgeon with screen markings that point out things like tendons, arteries, nerves, or where to make an incision. Proximie, which has been in use since 2016, has been used by doctors in Beirut to assist surgeons operating in the Gaza Strip."

In June 2020, neurosurgeons at Johns Hopkins University announced an augmented reality surgery, which involved a doctor placing six screws during a spinal surgery. Soon after, they used AR in the removal of a spinal tumor from someone else. The AR technology used included a headset display the doctors could see through to the patient. It allowed them to project images from X-rays or CT scans, for example, onto the body of the patient, to see both at the same time. As long as the images are lined up just right, it is almost as of surgeons have X-ray vision.

Several commercial HMDs, such as Microsoft HoloLens, Meta, or Magic Leap, integrate tracking and registration technology, and the deployment of software development kits has reduced technical complexity of custom application development, allowing for a wide range of users to easily create AR applications. The HMDs mentioned are designed following an optical see-through (OST) approach, which augments the natural view through the projection of virtual reality information on semitransparent displays in front of the user's eyes. The OST approach fits well in the surgical domain as it offers an instantaneous full-resolution view of the real world, allowing the natural synchronization of visual and proprioceptive information, and a complete situation awareness.

It has been pointed out by some, however, that commercially available head-mounted displays (HMDs) are presently unsuitable for AR surgical guidance. Maximizing surgical accuracy remains a challenge for manufacturers and researchers. Together with ergonomics, some critics feel the achievement of precision objectives must be addressed to develop a visor suitable for guiding surgical operations, not to mention compliance with medical device regulations.

An increasing number of research studies propose the use of commercial HMDs to guide surgical interventions. These works, however, appear principally focused on the need to strengthen virtual/real patient registration (e.g., use of an external localization system), improve virtual content stability, and solve calibration issues, and they underestimate the contribution of perceptual issues to the user accuracy.

One of the largest obstacles to obtain a perceptually correct augmentation is the inability to render proper focus cues in HMDs; indeed, the majority of systems offers the AR content at a fixed focal distance, failing to stimulate natural eye accommodation and retinal blur effects.

I. Augmented Reality Holographic Teleportation (Holoportation).[42]

[42] See https://aexa.com/holoportation/; see also

Holographic teleportation (holoportation) is an augmented reality (AR) training application. Users receive three-dimensional instruction from someone off-site whose image is projected through the lens via a hologram. For example, the application can allow for an engineer to simulate a "walk" through a space station, or for a doctor to "appear" in a patient's home. Or for a Subject to appear in a doctor's office.

There are three levels in communications. Level 1 is voice; level 2 is two-dimensional video; level 3 is holographic teleportation.

Current holoportation kits are portable, fit in a backpack, and work with low bandwidth (~5 Mbps). The communication is highly encrypted.

Unlike traditional holographic projections that appear to hover in the air for anyone to see, holoportation currently requires the use of an augmented reality headset, such as Microsoft's HoloLens technology, for the wearer to be able to perceive (and interact with) the remotely captured individual(s), who are filmed with a multiple-camera setup in their actual location.

In October 2021, thanks to Microsoft's "holoportation" technology, which allows users to interact with 3D representations of remote participants in real-time, NASA flight surgeon Josef Schmid was "holoported" to the International Space Station (ISS), appearing and conversing as a virtual presence in real-time.

Thomas Pesquet, a European Space Agency (ESA) astronaut on the ISS, was wearing an augmented reality headset, and had a two-way conversation with Schmid and members of his medical team.

Using the Microsoft Hololens Kinect camera and a personal computer with custom software from Aexa, ESA (European Space Agency) astronaut Pesquet had a two-way conversation with live images of Schmid and De La Pena placed in the middle of the International Space Station. This was the first holoportation handshake from Earth in space.

Holoportation is a type of capture technology that allows high-quality 3D models of people to be reconstructed, compressed and transmitted live anywhere in real time, Schmid said. When combined with mixed reality displays such as HoloLens, it allows users to see, hear, and interact with remote participants in 3D as if they are actually present in the same physical space. Holoportation has been in use since at least 2016 by Microsoft, but this is the first use in such an extreme and remote environment such as space.[43]

[43] https://www.nasa.gov/feature/innovative-3d-telemedicine-to-help-keep-astronauts-healthy.

This capacity to bridge physical gaps to connect people over huge distances has profound implications and enables interactions, for example, between doctor and patient (human or animal), that are much more involved and immersive than standard 2D video calls.[44] This capacity, of course, has profound implications for teledermatology, and for better triage and diagnostics with respect thereto.

[44] See https://www.sciencealert.com/nasa-surgeon-beamed-to-international-space-station-in-holoporation-world first/amp.

New advances have been made and are being made with regard to holography every day regarding high-resolution images and other material technical advancements that make the holoportation as described in this invention practical.[45]

[45] See, for example, http://www.postscientist.com/2022/12/ai-designed-structured-material-created.html#:~:text=AI-designed&20structured%20material%20creates%20super-resolution%20images%20using%20a,augmneted%2-Fvirtual%20reality%20%28AR%2FVR%29%20systems%20is%20holographic%20image%20displays and https://www.marktechpost.com/2022/12/08/ucla-researchers-report-a-deep-learning-enabled-diffractive-display-design-that-is-based-on-a-jointly-trained-pair-of-an-electronic-encoder-and-a-diffractive-optical-decoder-to- synthesize-super-resolv/.

SUMMARY OF THE INVENTION

The present application describes a skin care system which is carried out using one or more computers.

It is an object of the present invention to use a computer to assist with the skin care of humans and/or animals, and also to assist with other health care issues of humans and/or animals that may be indicated and potentially identified through the examination of skin (including hair and nails) ("skin data"). The term "skin data" as used herein means any data that characterizes any part(s) or attribute(s) of the skin. Skin data can include, for example, for any particular skin area: skin temperature, skin texture—the visual or tactile surface of the skin's epidermis layer, the skin's dermis layer, and/or the skin's hypodermis layer, the skin's chemistry, and/or the skin's color. Some examples of skin data are referred to here, however, the inventor intends the term "skin data" to include all data about parts of the skin, and not limited to enumerated data or parts. This is intended to make the skin care better, faster, and cheaper.

This is based on the inventor's recognition that monitoring and examining changes in skin health can be useful in alerting one to and potentially protecting one from many health issues and problems, using the techniques described herein.

The evaluation of skin, including without limitation its appearance and other attributes, can assist in the identification and treatment of the health of skin per se, and can also assist in the potential identification of other related health issues.

In embodiments, the application describes how relationships between skin diseases can be used to diagnose other diseases. For example,
(i) Eczema is linked to sleep disturbances, joint problems, and other injuries,
(ii) Stasis dermatitis can be a symptom of underlying diabetes and its effects on your body's circulatory system, and
(iii) Psoriasis often occurs alongside arthritis or other joint diseases.

Other specific analyses and descriptions are provided herein.

Further, nail color, shape and texture, and changes thereto, are associated with indications of a number of body disorders, such as, without limitation, diabetes, kidney or liver disease, or anemia. Any data of this type, which refers to any feature of skin, is included as part of skin data.

The inventor describes how the collection of skin data in a similar way whereby the collection and analysis of the data, including a comparison of skin trends over time, can reveal a number of significant "indications" that may play a role in your general health.

Also, it is the intention of the invention, through its use of "machine learning" and "deep learning" software, to uncover new correlations between and among skin health and general health. The invention describes correlating, in one embodiment using "deep learning" software to do so, the data results from the blood data and the skin data, to find new discoveries from such comparisons.

The following comprises some additional potential types of "health data" of humans and/or animals that can optionally be obtained from a Subject (or the Subject's medical Professional) that can be compared and cross-referenced (by the invention) with skin data of the Subject (as collected and analyzed by the invention), in real time, near-real time, or distant time, so the compared cross-referenced skin data and "health data" information, if statistically relevant, benefits science and humanity in terms of new discoveries and improvements, but also potentially directly benefits the Subject (or the Subject's owner if the Subject is an animal) by providing a "firmer indication"/more definitive indication/stronger indication of a Subject's condition and/or the trend and speed of the trend in a Subject's condition (than might otherwise be the case with only the Subject's skin data alone).

In one embodiment, this is referred to as "skin data-plus", for a more holistic view of the indication of a Subject's condition and/or trend and speed of the trend of a Subject's condition.

An embodiment of the Invention can Compare and Cross-Reference Skin Data and "Health Data" as described in this patent application and as described in the following. The invention to effectuate the comparison and cross-referencing of:
(x) Subject skin data (as obtained and processed by the invention) with
(y) additional potential types of Subject "health data" (i.e., e.g., but without limitation, blood, Body Mass Index, blood pressure, pulse oximetry, weight, et al., all with the date and means acquired, etc.).

This data comparison and cross-referencing (which may involve numerous combinations and/or permutations of the same) can be done, without limitation, through the use of specialized "if-then" and/or AI software known to those skilled in the art, as well as through the use of other methodologies known to those skilled in the art.

Embodiments can be used to simplify, make more convenient, and make more objective (and therefore better) the identification of potential health issues with regard to not only skin per se, but also other health issues that may be indicated through an examination of skin data.

The invention is also intended to enable the remote, at-a-distance, examination and evaluation of skin data, in real time, near real-time, or delayed time, by health care professionals ("Professionals").

Also, the embodiments describe the generation, image registration (using mathematical methods known to those skilled in the art), relocating and regenerating of AR visual marks with various attributes to mark, in an intangible non-contact manner, visible only to those with Subject permission, targeted Subject skin targets, to identify and measure them for further evaluation in real time and in the future, to assist in the future location of them and to determine if the Subject's targeted area of skin is improving or worsening from a skin health perspective.

In other embodiments, the invention is intended to identify unique biometric markers in the skin or targeted areas thereof that may be used in a variety of ways as described herein. The use may be in opening or locking locks, automatic door opening or closing, computer logins, security identification, identification for accidents or surgery, or other applications.

DETAILED DESCRIPTION

Figure 1:
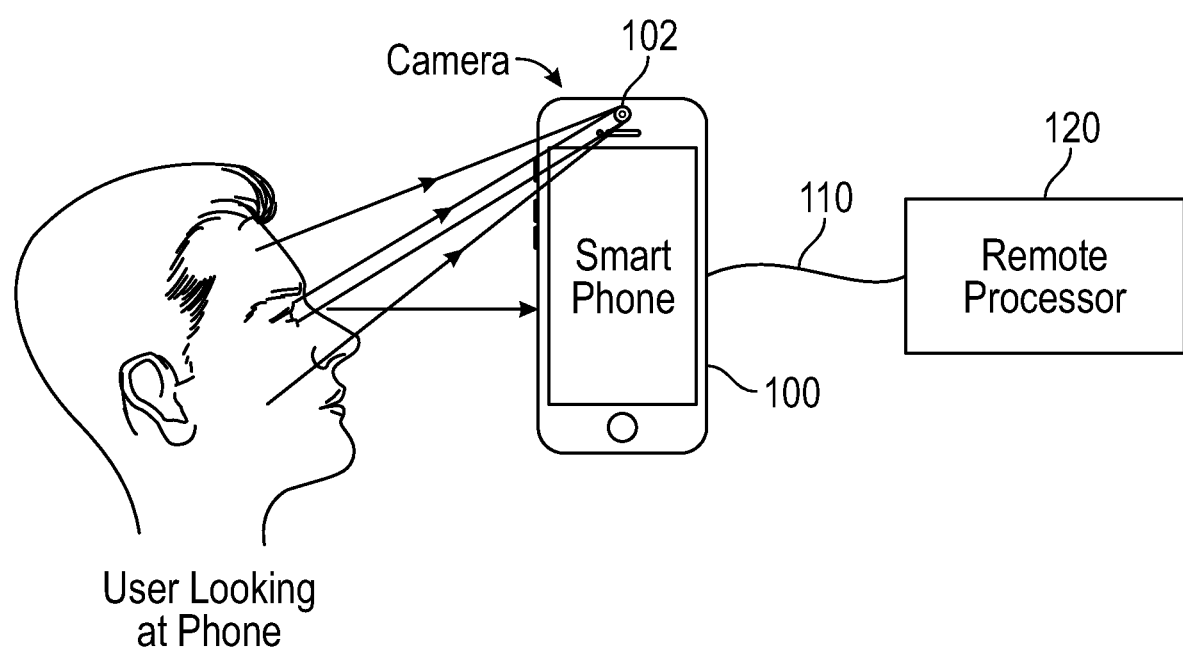
FIG. 1 illustrates an app being used to obtain facial skin data.

An embodiment describes remotely characterizing and determining issues with patient health based on skin examinations.
A. Replicating Much of the Traditional In-Office Exam At-a-Distance.
1. Initial Set-Up.
Similar to current skin exams, the invention envisions the person whose skin will be examined initially answering written or verbal questions online (by a Professional or AI-powered chatbot), or by verbally responding or filling out a form online, providing information about his or her age, gender, ethnicity, general health, any medications being taken, any allergies or skin problems, a brief medical ocular and surgical history, and family medical history. However, instead of this taking place in your dermatologist's or doctor's office, this process begins in Subject's home (or, for example, in a local pharmacy office or school).

Depending on the setting, additional information may be collected such as Body Mass Index, blood pressure, pulse oximetry, smoking status, and dietary habits.

2. Advantages.

For the person whose skin (or targeted portions thereof) will be examined or monitored, the Subject saves time and expense in not having to schedule a formal appointment with a dermatologist or doctor, and not having to travel to-and-from that Professional's office once, if not a number of times. Further, in this age of epidemics and contagious infections, there is the benefit to Subject and Professional alike that no human contact or close proximity is necessary.

B. Teledermatology: Version 1-Being Virtually Side-by-Side with a Human Professional.

Useful for Professionals practicing teledermatology, as known to those skilled in the art, in the use of:

1. "Store and Forward" Technology.

A referring physician or patient will send high-quality digital images through a secure link within the UPMC electronic medical record (EMR) platform. The site is accessible to patients through the secure MyUPMC app, using their personal login, and it's available to physicians through the EMR. This method means that both parties don't have to be available at the same time. A patient or physician can simply send a request with digital images. A UPMC dermatologist will then access the images through the eDermatology program.

2. Synchronous Teledermatology.

Synchronous teledermatology is a live video stream, which patients can access through the MyUPMC app. In this case, a dermatologist and patient or a dermatologist and physician are meeting in real time through a live video conference. By either mechanism, the receiving teledermatologist can identify the problem and offer the best evaluation and management.

3. Electronic Digital Images.

Dermatology is a visual specialty that is often pursued by physicians who are visual learners. During a dermatologist's training and continual medical education, a dermatologist learns to become and maintain a master of skin disease by studying electronic digital images during lectures and through photographs of skin disease in medical textbooks and journals. Arguably practicing teledermatology is not that different.

4. Teledermatology Equipment.

A PC, Mac or laptop running the latest operating systems, a video camera and a microphone and speakers. Most laptops have a camera and microphone and speakers inbuilt. The audio component of the teleconference is best conducted with a telephone. This can be placed in speaker mode so that the patient can both hear and ask questions. iPads, iPhone and Zoom can do some elements of telemedicine but not all.

Between mid-March and mid-October 2020, over 24.5 million out of 63 million beneficiaries and enrollees received a Medicare telemedicine service. However, since the return of in-person visits, interest has waned significantly.

Teledermatology Subject Preparation. Subjects need to give a clear picture of their skin's condition. They need to prepare for a video visit the same way they would an in office visit (e.g., the removal of any makeup). Clothing should be worn that can easily be moved to show the doctor the Subject's rash or other skin condition or skin target of concern. Natural lighting is best. The Subject should avoid using any scrubs or exfoliants before the teledermatology session. Some dermatologists ask the Subject to take three photos of the skin area of concern from different distances.

C. Teledermatology: Version 2-Using "Machine Vision" Together with Rules-Based Programs, Machine Learning and AI Software (Including Various "Flavors" of Deep Learning Software) to Provide Indications and Predictions.

1. Initial Set-Up.

The initial set-up is virtually the same as in A.(1) above.

2. Advantages.

The invention can perform the periodic skin review and examine the skin (or targeted areas thereof) of a Subject much more quickly and comprehensively than a human skin expert can, because as a computer-based system:

a. it has better and faster access to computer database records (if any) of prior skin examinations of the same Subject;
b. it can perform an objective skin comparison of one targeted area of skin to another targeted area of skin of the Subject during the same time period (i.e., e.g., texture and/or color comparisons, etc., using computer vision and other relevant software), and provide objective measurements, while a human's measurements are typically subjective (and vary from human to human);
c. it can perform skin comparisons (or targeted areas thereof) (i.e., e.g., texture, color, and thermal comparisons, etc., using computer vision and other relevant software), comparing a new digital picture/image, digital video clip, and/or thermogram to a prior digital picture/image, digital video clip, and/or thermogram (if any) of the skin (or targeted areas thereof) of the same Subject, revealing skin condition changes over relevant time periods;
d. it can perform skin (or targeted areas thereof) comparisons (i.e., e.g., texture, color, and/or thermal comparisons, etc., using computer vision and other relevant software) comparing new digital picture/image, digital video clips, and/or a digital thermogram of the skin (or targeted areas thereof) of the Subject to computer database records of digital picture/image, digital video clips, and/or digital thermograms of similar "healthy" skin (or targeted areas thereof) or skin (or targeted areas thereof) with known condition(s) displayed in skin (or targeted areas thereof) that are similar to the potential condition(s) of the Subject displayed in the skin (or targeted areas thereof) of the Subject;
e. it does not require the time expenditure of travel by the Subject to the offices of a human skin expert or of the human skin expert to the location of the Subject;
f. AI systems, unconstrained by prevailing theories and biases, can identify new targets by spotting differences at the level of tissues in healthy skin, and differences that might elude or mystify a human scientist.
g. if programmed correctly, software does not consciously or unconsciously positively or negatively discriminate against the Subject whose skin (or targeted portions thereof) is being examined. It is not sensitive to age, gender, ethnicity, race, et al.
h. any benefits of the invention not described herein.

3. Follow-Up Questions and Follow-Up Data Collection.

Somewhat similar to the manner in which certain artificial intelligence deep learning programs use back-propagation to improve the efficacy of the predictiveness of the program, the invention may ask follow-up questions of the Subject to obtain data to refine and improve the Rules-Based Program/ "if-then" and/or predictive aspect of what the invention is measuring. The invention may also suggest to the Subject that Other Information be obtained and provided.

Much of the information in the present specification comes from the inventor's recognition that technology for obtaining image information is continually improving. For example, the camera and camera-related software on smartphones and pads, using artificial intelligence (including deep learning) in the smartphone or pad (and in the cloud to which the pictures and video are sent) —will continue to improve and do amazing things. This will only get more ubiquitous with the coming of new mobile technologies such as 5G, and the continual evolution of Internet of Things (IoT). In addition, natural language processing and AI-powered chatbots will continue to improve.

Use of the "elastic cloud" and the computing and storage therein, and the amazing cost-effective things that can be accomplished on that platform, and the migration thereto has only just begun.

D. An AR Visual Marker and AR Audio Note/Message System.

The AR visual marker and AR audio note/message system:

1. using no physical contact with the Subject (except in one optionality a physical distance guide used to accurately gather Subject skin data), itself or through its user identifies and targets one or more selected potential skin issues or indications located on the skin of a Subject or already located on the skin of a Subject based on other portions of the invention or other means;
2. using no physical contact with the Subject (except in one optionality a physical distance guide used to accurately identify and gather Subject unique biometric data), identifies unique biometric data of the Subject (i.e., skin pores'/hair follicles' patterns, blood vein patterns, and/or thermogram heat patterns, or some combination or permutation thereof), from on, near, and/or surrounding the identified and targeted selected potential skin issue or indication on the skin of a Subject;
3. using computer-generated filters, by using "deep learning" and or potentially other artificial intelligence methods and techniques, to transform the Subject's unique biometric data into numerical expressions that are stored for later use in relocating the earlier identified and targeted area of the skin of the Subject on, near, and/or surrounding the biometric data, and stores such data;
4. generates an AR visual mark and/or AR audio note/message (for example but without limitation, an audio human voice [for example, but without limitation, made by the Subject or the health care professional] or a natural language processing (NLP) note that is mathematically anchored to the numerical expressions representing the Subject's unique biometric data on, near, and/or surrounding the identified and targeted selected potential skin issue or indication of the Subject; and
5. can relocate and re-generate the identical AR visual mark and/or AR audio note/message at the same location at which it was earlier mathematically anchored to the numerical expressions representing the Subject's unique biometric data on, near, and/or surrounding the identified and targeted selected potential skin issue or indication of the Subject, These features are carried out using one or more computers.

This desired operation is based on the inventor's recognition that (i) physical skin markers have shortcomings and are lacking in functionality in an increasingly digital world, (ii) an AR visual marker and AR audio note/message system lends itself to teledermatology in numerous ways, and (iii) monitoring and examining changes in skin health through the use of an AR visual mark and/or AR audio note/message can be useful in alerting one to and protecting one from many health issues and problems.

E. The User Portion of the Invention.

The user-end portion of the invention (the end closest to the skin of the human and/or animal being evaluated), is shown in the Figures. A first embodiment, shown in FIG. 1, uses:

1. Smartphone (or Similar Device) (the "Device").
   a. A smartphone 100 or similar device (the "Device"), together with a software application loaded in the Device, used by a user who previously provides relevant personal information regarding the user's age, health, and other personal details independently or through the Device, and sets certain parameters provided in the software application.

The camera 102 of the Device 100 operates to either be (i) used manually by the user, or (ii) automatically turn on and video record skin data at pre-selected intervals and for preset durations. The camera can record images, which in this specification can include still images, or moving images such as videos. For purposes of this patent application, the videos can be considered as a number of different images, obtained of one or more areas on the skin. The skin data can be color data including data about the user's skin or targeted areas thereof and selected potential indications or conditions thereon. The pre-selected intervals can be, for example, every day, every week, every month. The preset durations can be 10 seconds, 30 seconds, or 2 minutes.

In one embodiment, this is automatically done while the user is looking at the display screen of the smart phone 100, doing whatever screen time activities the user happens to be doing.

The information from the obtained video is transmitted at 110 to a remote processor, for example a cloud processor. The user can give prior consent to obtaining and processing this information as described herein.

The Subject/user can speak by a Device built-in microphone or separate wired or wireless microphone), and Subject/user can hear by a Device built-in speaker or separate wired or wireless earphones or headphones. The Subject/user can hear a Professional and/or an AI-powered chatbot.

Various different types of add-on cameras (which are part of the invention) can be added to the Device as desired to allow capture of skin data from various targeted parts of the skin of the Subject. Alternatively, a Device can be a stand-alone device with just the appropriate type of camera (i.e., it would not be an "add-on" camera to a smartphone-type device).

In a first embodiment, the remote processor 120 operates by sending the information to a Professional, e.g., one selected by the user, who receives the skin data and reviews and examines the video in real time (potentially also interacting with the user by audio or otherwise in real time), near-real time, or delayed time. The skin data can be evaluated, displayed, and potentially manipulated in various ways, including, without limitation, (a) being enlarged/magnified, (b) replayed in slow motion, (c) displayed in augmented reality and/or virtual reality three-dimensionality, (d) displayed with alternative coloration for better contrast, or (e) compared with other skin data either directly by the Professional or through the use of artificial intelligence software, and report back to the user.

In another embodiment, the remote processor 120 receives the data and uses a software program to compare that data to other stored skin data about the user. In an alternative embodiment, that processing can actually be carried out in the phone itself, rather than in a remote processing unit.

Figure 1B:
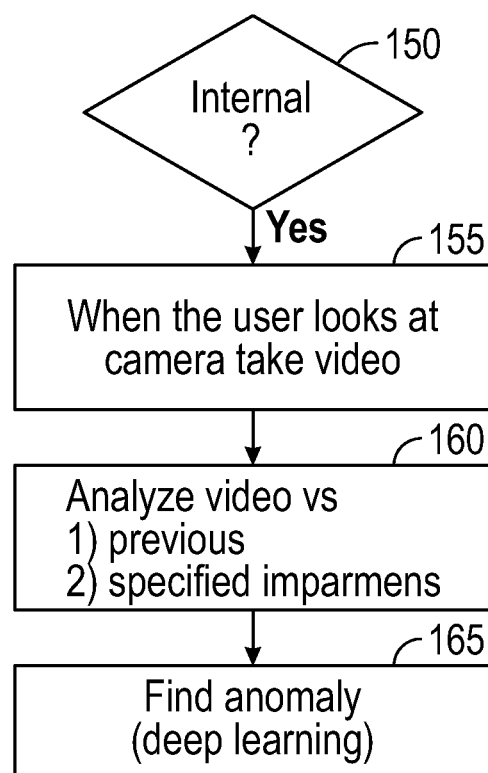
FIG. 1B shows a flowchart of obtaining the skin data.

The processing is illustrated in the flowchart of FIG. 1B. An object of the processing is to use as much machine intelligence as possible to find some marker in the skin which indicates that there can be a problem. The software uses the machine, e.g. the portable phone or tablet, to process the data at intervals at 150. As described above, the intervals can be specified intervals of time, and each time the specified intervals of time occur, the machine can use its camera to image the face of the user who is looking into the phone at 155. This processes the data by obtaining a video or image of the user's face at 155.

At 160, the video is analyzed relative to previous videos and/or relative to known images of specified impairments. When processed relative to previous videos, this can be done to find a change in some portion of the user's skin data. The program can also compare the skin data and its changes to other patterns and skin data changes in its memory. Examples of the kinds of things that the software looks for can include comparing the skin data with data indicative of healthy skin. The skin data can also be compared with skin of others who have specified health conditions. By finding similar skin data to those who have specified health conditions, this can postulate similar kinds of health conditions in the user whose skin data is being analyzed. The skin data is used to find health conditions other than those related to the skin. At 165, if the system finds an anomaly, the system can report back information to either (a) the user, or (b) to a Professional.

Another embodiment adds this to a deep learning software program which forms part of the remote processor 120. The deep learning program evaluates what it receives based on what it has previously learned about the skin data and related general health information of the particular user or of the population in general, and reports its findings and indications back to either the user, or a Professional pre-selected by the user.

The Device software application program may be set for a Professional to be able to examine the user's skin (or targeted areas thereof) remotely, at a distance, in real-time while interacting directly with the user by audio or otherwise. Related thereto, the Device software application may be set whereby the Professional can take control of the Device and its software application remotely in order to better conduct the examination of the skin (or targeted areas thereof) of the user.

Another embodiment may use an augmented reality scanner (a software application addition), or a 3D camera attachment to obtain 3D information about the skin. This can allow the Subject's skin (or targeted areas thereof) to be transmitted, remotely viewed at-a-distance and examined (i.e., a "live" viewing) and/or recorded, transmitted and remotely viewed and examined, by a human or software, with a certain amount of three dimensionality and the ability for potentially greater manipulation of the video display or video recording on the receiving end, by either a Professional or by artificial intelligence software.

Another embodiment uses a laser-powered 3D camera and/or a LiDAR scanner (a form of which is currently found in the iPAD Pro 2020, and included in one or more of the versions of iPhone 12), which LiDAR scanner can accurately judge distances and therefore depth, and allows for improved augmented reality.

b. An advantage of the software application as used in a Device is that it can automatically turn on the video camera of the Device at preset intervals. Also, other than initially configuring the software application, the user does not need to think or remember anything: the software application performs its function and monitors the user's skin (or targets areas thereof) and reports its findings and indications back, either directly to the user or through a Professional pre-selected by the user as to whether there is any potential issue the software application in the cloud or Professional pre-selected by the user identifies on which the user might want to follow-up.

c. The user may want this skin report and backup to be forwarded to the user's insurance company or to any other party, which can be a pre-selected function of the software application program.

Figure 2:
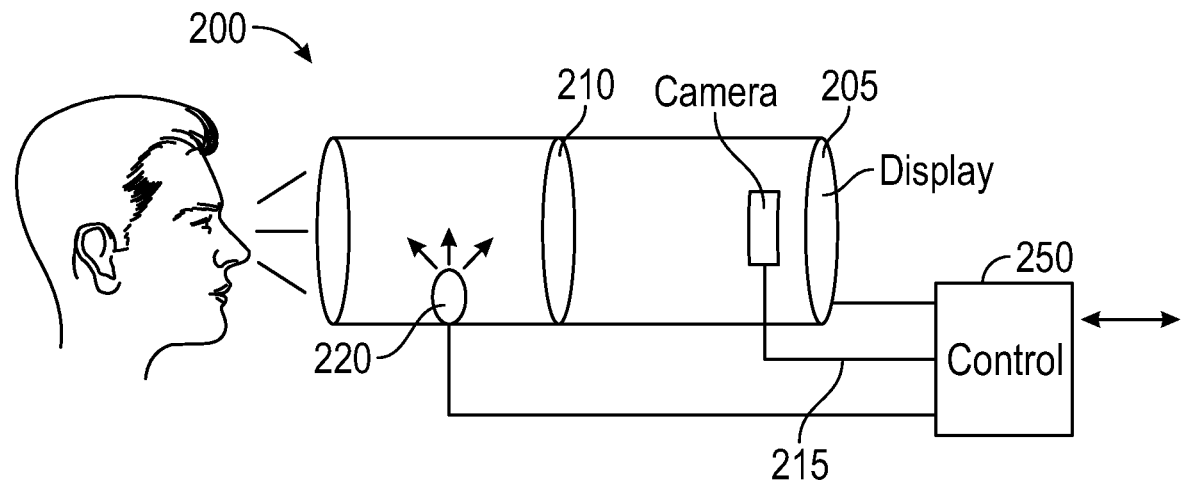
FIG. 2 shows a periscope embodiment.

A second embodiment uses:

2. A Chamber-Plus-Device.

a. Another embodiment describes a device 200, shown in FIG. 2, in one configuration similar to a periscope, with a chamber which on one end 200 the user peers into (with or without glasses, with one eye or both eyes), and on the other end the Device is attached with its video screen 205 display facing inward (the "Chamber-Plus-Device"). The Chamber, in the configuration similar to a periscope, has internal magnifying mirrors 210 tilted at correct angles so that the Chamber enlarges the display so the user can clearly and better see the attached Device's display-screen to see the targeted area of skin of the Subject being imaged. By using this device, the system enables obtaining magnified versions of different areas.

Alternative 1: The Chamber-Plus-Device configuration can be a straight tube, and the user peers through non-distorting magnifying lens(es) facing the inward facing attached Device camera on the other end of the tube.

Alternative 2: The Chamber-Plus-Device can be configured with flexible joints, with internal magnifying mirrors or a reflective surface at the places where the joints flex so, for example but without limitation, the Subject can image selected portions of skin on the Subject's back or other hard to reach-and-see places on the body of the Subject, so the Subject can clearly and better see the targeted area of skin being imaged by the attached Device on the attached Device's display-screen.

Alternative 3: Adding a separate macro lens or digital dermatoscope on the attached Device camera to better capture the image data desired on targeted area of skin of the Subject (including without limitation the relevant biometric data of the Subject, located on, near, or surrounding such targeted area of skin, including without limitation, the unique (i) skin pores'/hair follicles' pattern of the Subject, (ii) blood veins' pattern of specific areas of skin of the Subject, and/or (iii) thermal patterns caused by moving blood beneath the skin of the Subject, and/or (iv) some combination or permutation of each of the foregoing).

b. Using the Chamber-Plus-Device is similar to using the Device alone, except:

(i) The Chamber offers superior control of the amount of actual light 220 into the Chamber itself, which can be used so the user can more clearly and better see the attached Device's display-screen to see the targeted area of skin of the Subject being imaged, thereby providing a clearer and more consistent video of targeted areas of skin of the Subject.

(ii) The Chamber generally offers more of a fixed distance (i.e., focal range) between the skin of the Subject being imaged and the Device camera (as compared to a user simply holding the Device a random distance above the Subject's skin and attempting to image hard to reach areas of the Subject's body), which can provide clearer and more consistent video of targeted areas of skin of the Subject. The "fixed distance" can be based on the use of a "physical guide" or an electronic guide, the later of which could use an audio or video signal to indicate when the Device relevant camera and/or sensor is within an appropriate distance range to properly perform its function, or to notify the user if the Device relevant camera and/or sensor is outside of the "sweet spot" range.

(iii) The Chamber allows for the introduction of external lighting of the skin being imaged by the Device in various ways for examination of targeted areas of the Subject's skin, beyond lighting coming from the Device itself. Such lighting may be a different type of light, such as, for example but without limitation, infrared light, to better see the Subject's blood veins.

(iv) The Chamber's external lighting can be controlled remotely by a Professional, or by the software application program running on controller 250. The professional has access to the controller 250, and can request the controller 252 increase or decrease the illumination during the time that the professional is viewing the skin of the patient. The controller itself can have wireless or wired connection between the Device and the Chamber to effectuate such Chamber lighting control remotely.

(v) Unlike the Device and application software alone, in general the Chamber-Plus Device must always be used consciously by the user (who may be the Subject), since the user must hold the Chamber-Plus-Device to allow it to obtain images of specific areas of the Subject's skin selected by the user, and accordingly in general the Chamber-Plus-Device cannot be set on automatic as is possible with the Device and application software alone for obtaining certain specific images of the user's skin (e.g., the user's face). That said, the Chamber-Plus Device can be set on semi-automatic for many test functions. These semi-automatic functions can be initiated by conversations between Subjects and Professionals and/or invention AI-powered chatbots or by other means. Notwithstanding the foregoing, third party professionals, such as ambulance attendants and emergency care health care professionals, can use the Chamber-Plus-Device to record certain areas of the skin of a conscious or unconscious "user" (for, for example, burns or puncture wounds) and configure the application software to record the relevant areas of the "user's" skin at automatic periodic intervals.

(vi) The Chamber itself can be designed in many configurations, one better than the other depending on the intended user (e.g., the owner holding it up to a certain area of skin of a dog, cat, or horse).

3. The "Magic Mirror".

Figure 3:
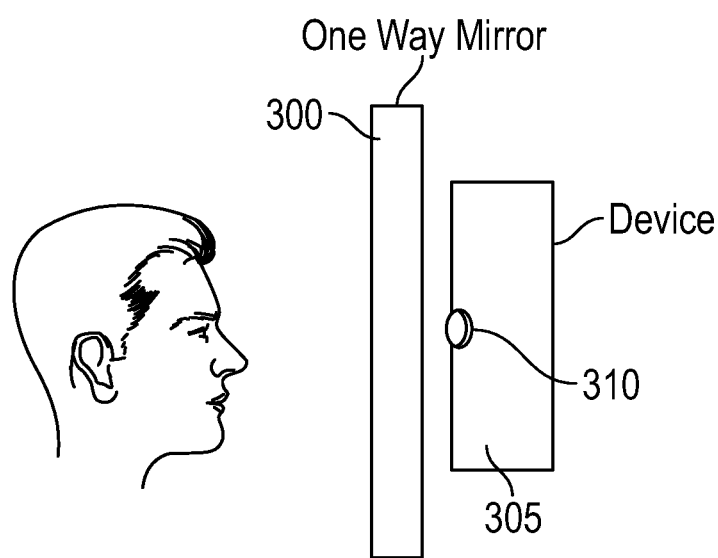
FIG. 3 shows a one-way mirror embodiment.

A "magic mirror" 300, shown in FIG. 3, is a one-way mirror (which may be made of different substances as known in the art). Behind the one-way mirror 300, on its non-reflective side there is the Device 305. The device 305 has a camera and/or other imaging sensors 310 facing toward the non-reflective side of the mirror. This enables viewing and recording image data indicative of the skin of the user who is on the reflective side of the mirror. By its nature, the user cannot see the Device 305, since it is on the other side of the Magic Mirror. As shown in the embodiment of FIG. 3, the magic mirror device can obtain images of the user's skin when the user is looking in the mirror. This enables obtaining automatic images or videos, in a similar way to the first embodiment.

An embodiment uses a type of glass that can allow thermal imaging through the glass.

Many kinds of glass do not allow thermal cameras to see through glass. https://www.quora.com/Can-some-thermal-cameras-see-through-glass. But spectral thermography allows measurements on and through glass.] https://www.infratec-infrared.com/thermography/industries-applications/glass-industry/. "The problem of glass measurement can be solved by applying InfraTec's infrared camera systems of its high-end camera series ImageIR®. These are possible to be equipped with spectral filters being deployed in a filter wheel. Filters will be individually adjusted according to the specific glass of the customers. On the one hand, these filters allow measuring the surface temperature of glass without any impact of the transmission radiation of objects behind glass. On the other hand, measurements of objects with high temperature behind glass can be carried out without having an influence on the glass surface temperature. Since the infrared camera's filter wheel is power-driven and remotely controllable, switching between both modes can be ensued by a keystroke at the control computer." Id.

"Sapphire, for instance is apparently transparent in the MWIR spectrum, though not in the LWIR spectrum, so it would theoretically be transparent to high-end cooled thermal cameras but opaque to the much more common uncooled thermal cameras." [https://www.quora.com/Can-some-thermal-cameras-see-through-glass.]

a. The Magic Mirror is like item 1(*a*) above in that the Device by with a software application images the patient's face. The Device 305 with its software application resides behind the Magic Mirror 300, which can be portable or stationary. Instead of looking directly at the Device and having the skin on the user's face automatically recorded while the Subject is engaging in whatever activity, or another area of skin on the Subject's body recorded by the Subject, with the Magic Mirror the Subject looks at or poses in front of the Magic Mirror to, for example but without limitation, comb his or her hair, brush his or her teeth, apply his or her make-up, or put on clothing (for example the Magic Mirror could be a dressing mirror), and during that time the camera and sensors behind the Magic Mirror automatically turn on and video records in color the Subject's skin, in detail, and transmits the video to "a cloud", or other data reception or storage device.

The Magic Mirror can have a built-in microphone (e.g., built-in) voice input for the Subject and built-in speaker (e.g., built-in) audio output for a Magic Mirror. In an alternative embodiment, the microphone and speaker can be external and attachable. In any event, Magic Mirror should have optional AI-powered chatbot (audio input and output) capability. If selected, the invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programmable and optional. Human Professionals could substitute for the invention chatbot.

Another name for a Magic Mirror is a glass teleprompter mirror, also known as a "beam-splitter mirror" or a transparent mirror. It is a semi-transparent mirror that reflects text while allowing flawless recording through it, in 1080p, 4K, and higher resolutions. The back side of the mirror has an anti-reflective coating which prevents "ghosting", which is a double image you would see when using standard glass.

There are various types of beam-splitters. Standard beam-splitters, which split incident light by a specified ratio into two (or sometimes more) beams, which may or may not have the same optical power, that is independent of wavelength or polarization state, are ideal for one-way mirrors.

4. Plain Mirror with Device on the Outside/a Visible Device Body-Length Strip (the "Mirror Strip Attachment")

The Magic Strip Attachment is an implementation like item 1(a) above (i.e., the Device by itself together with a software application), except that the Device with a software application resides as a temporary or permanent attachment to or part of, for example but without limitation, a body-length dressing mirror (which can be portable or stationary), in which the camera and sensors and the rest of the Device are in a strip that run along the outside of the edge of the frame of vertical length of the mirror. In other words, instead of being hidden behind the mirror, they are on the outside on the mirror on its side, and the skin data collected in a full body scan of the Subject is automatically stitched today by means known to those skilled in the art. The Subject knows the Mirror Strip Attachment is there because it is visible, and the Subject can be made aware through various means, such as a red light, when the imaging operation is active. As with the Magic Mirror, the Subject looks at or poses in front of the mirror to, for example but without limitation, comb his or her hair, brush his or her teeth, apply his or her make-up, dry oneself after a shower, or put on or remove clothing, and during that time the camera and sensors behind the Magic Mirror automatically turn on and video records in color the Subject's skin, in detail, and transmits the video to "a cloud", or other.

As with the Device itself as described above, the cameras of the Mirror Strip Attachment operate to either be (i) used manually by the user (I.e., the user consciously turns the Mirror Strip Attachment on or off, or (ii) automatically turn on and video record skin data at pre-selected intervals and for preset durations. The skin data can be color data including data about the user's skin or targeted areas thereof and selected potential indications or conditions thereon. The pre-selected intervals can be, for example, every day, every week, every month. The preset durations can be 10 seconds, 30 seconds, or 2 minutes.

In one embodiment, this is automatically done while the user is in front of the mirror, doing whatever activities the user happens to be doing.

The Mirror Strip Attachment can have a built-in microphone (e.g., built-in) voice input for the Subject and built-in speaker (e.g., built-in) audio output for a Mirror Strip Attachment. In an alternative embodiment, the microphone and speaker can be external and attachable. In any event, the Mirror Strip Attachment should have optional AI-powered chatbot (audio input and output) capability. If selected, the invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programmable and optional. Human Professionals could substitute for the invention chatbot.

It should be noted the Mirror Strip Attachment need not be attached to a mirror per se for it to function and adequately perform its function, which is essentially to obtain a full body scan of the Subject. For example, but without limitation, it could be placed on a wall. The user need not actually see herself or himself in a mirror for appropriate use of the Mirror Strip Attachment.

5. Another Embodiment Uses a Wearable/Digital-Computer Watch (or Similar Device) Such as the Apple Watch but with Camera(s) and Sensors in/on/Connected to it (the "Watch").

Camera(s) can monitor the skin on wearer's face when the Watch-wearer looks at the Watch.

Alternatively, the Subject can consciously use the Watch to image any selected area of skin on his or her body.

If the skin area the Watch-wearer wants to consciously target is a hard-to-reach or difficult-to-image area (for example, but without limitation, the Watch-wearer's toe-nail), the Watch-wearer can either (i) remove the Watch from the Watch-wearer's wrist and use the Watch like a hand-held Device, or (i) have someone else use the Watch like a hand-held Device for the benefit of the Subject.

The Watch can (i) locally process skin data and have a transceiver of its own to transmit skin data to the cloud, and in turn receive data from the cloud, or (ii) by Bluetooth or other wireless means can connect to a smartphone or other similar device to process and transmit data to the cloud, and in turn receive data from the cloud and transmit it to the Watch.

The Watch can have one camera, multiple cameras, and/or various types of cameras on it, as well as appropriate sensors. Two cameras, for example, can capture skin images in 3D, and if the Watch-wearer has a specific medical condition that the Watch-wearer wants to monitor through the wearer's skin (including a condition or potential condition of the skin caused at least in part by the body or brain disease or condition), the Watch-wearer can get a Watch with a Watch camera or cameras and sensors and software in it that can examine that area of the skin in the manner necessary to monitor that condition.

Also, the Watch can monitor the skin for a condition that has been "treated", to assist in determining how the treatment is working and progressing.

In one embodiment, the Watch may have a laser-powered 3D camera, and/or a LiDAR scanner (a form of which is currently found in the iPAD Pro 2020, and in one or more of the versions of iPhone 12), which LiDAR scanner can accurately judge distances and therefore depth, and allows for improved augmented reality.

The invention can report the results of the skin examination and monitoring back to the Watch-wearer (i) on the Watch, (ii) on the connected smartphone or other similar device, (iii) to the Watch-wearer's selected health professional, and/or (iv) to the Watch-wearer's selected health insurer.

The Watch can also be used for all other aspects of the invention that might involve a conscious human Watch-wearer as described in this patent application. The Watch has (i) built-in microphone or separate wired or wireless microphone; and (ii) a built-in output speaker and/or separate wired or wireless earphones or headphones, so the Subject/user has the ability to hear and speak through the Watch.

The Watch may also have an AI-powered chatbot (audio input and output) capability. The invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programable and optional. Human Professionals could substitute for the invention chatbot.

In an embodiment, are two versions of the Watch: (i) a standalone Watch, in which all the functionality resides in the Watch, and (ii) a Watch that works wirelessly together with the Device or a smartphone, in which some of the technology is in the Watch, and some in the Device, and they work together, with the Watch piggybacking off the Device's transceiver and battery, et al. (in a manner similar to how the first generation Apple Watch functioned).

6. Amazon Echo Show (or Similar-Type Device) which Either has its Own Transceiver or Wirelessly or by Wire Interacts with a Smartphone (or Similar Devise).

One modality of the invention is something somewhat similar to the Amazon Echo-Show (which connects to the Amazon cloud and allows for 2-way video and audio conference calls when coupled by Bluetooth with, for example, an iPhone or similar device), which, like the iPhone, can have various different types of add-on cameras and sensors (which are part of the invention) attached to it, to allow it, as desired by the Subject or a Professional, to capture skin data from various areas of the skin of the Subject.

Alternatively, it could be a standalone device with just the appropriate type of camera (i.e., it would not be an "add-on" camera to the Amazon Echo Show-type device), and sensors. This may use some components of an attached phone in order to carry out the communication.

The Amazon Echo Show-type device would either have its own transceiver or piggy-back off the transceiver of a smartphone (or similar type device) similar to what the Amazon Echo-Show currently does.

A basic Amazon Echo Show-type device might have only one or two different types of cameras, and appropriate sensors, and the specialized device might have many different cameras (activated as determined by the Subject or Professional and/or determinations made by the invention software [which may want greater magnification, a different filter, a different camera, et al.]).

Another embodiment uses "Chamber-Plus Amazon Echo Show-Type Device", as a variation, with similar benefits as described in the Chamber-Plus-Device section above.

7. Fixed Camera-Type Devices.

Everything done with the Device (as described above) can be done with a portable-but-fixed input device that can be affixed/attached/fastened/hung over a doorway or on a wall et al., in a Subject's residence, or over a door, by a feeding area, et al. in where an animal or animals is kept. The input device would have all the necessary functionalities as earlier described.

Examples of uses, without limitation of this type of invention portable-but-fixed input device include:
 a. Camera(s) and sensors fixed at the "doorways"/entry ways of animal barns, pens, or shelters (this is automatic skin data capture);
 b. Camera(s) and sensors fixed in animal feeding areas, animal stalls and/or holding/sleeping areas (this is automatic skin data capture);
 c. Camera(s) and sensors fixed on or near the outside wall of an aquarium, or in the water fixed near or on the aquarium floor, roof, or inside wall of the aquarium (this is automatic skin data capture);
 d. Camera(s) and sensors attached to fixed areas underwater (for example, without limitation, attached to a net and/or tethered to a dock, the side of a river, stream, lake and/or pond), that can capture, as part of the invention system, and as a means to implement its methodology, the skin data of fishes of various types (this is automatic skin data capture).

8. Laptop/Desktop Computer (with Built-In or "Clip-on Attachable Camera(s) and Sensors).

Everything done with the Device (as described above) can be done with a laptop or desktop computer, which, if it does not have a built-in camera (or one with sufficient capacity) can use one or more clip-on/attachable cameras (with sufficient resolution, magnification and frames per second ability, et al.) and appropriate sensors. That type of input device would have all the necessary functionalities as earlier described.

9. Drone Camera Input (the "Special Input Drone").

Everything done with the Device (as described above) can be done with a drone, assuming it has one or more cameras with sufficient magnification and frames per second ability, appropriate sensors, et al. The Special Input Drone input device has all the necessary functionalities as earlier described with the Device as described above. Alternatively, the Special Input Drone can wirelessly send and receive information to and from the smartphone or its equivalent (or directly to it if it is attached), in the same manner as the first generation Apple Watch.

Embodiments include two types of Special Input Drones: the "in-the-air Special Input Drone" (the "Invention Air Drone"), and the "in-the-water/underwater Special Input Drone" (the "Invention Water Drone").

a. The Invention Air Drone:
 (i) Is ideally used for examining and monitoring the skin of various types of non-fish animals outdoors, such as, without limitation, cattle, pigs, sheep, horses, et al. There are AR see-through smart glasses in the commercial marketplace (such as for example, without limitation, the Epson Drone Soar Application/Epson Moverio BT-300), which are optimized to assist in piloting air drones and making it easier to capture desired images and videos. There are also autonomous air drones that can do their work and return to base.

Camera(s) on the Invention Air Drone can capture, as part of the system of the invention and as a means to implement its methodology, the skin data of animals, for example:
 (i) Beef cattle in a cattle yard or on an open range;
 (ii) Pigs in the yard of a pigpen or a more open area;
 (iii) Free-range chickens (or other human-raised fowl, such as ducks or turkeys) that are outdoors (be it in a chicken yard or, for example, in a pasture); or
 (iv) Horses outdoors (in a coral or on a more open range).

Dependent on how programmed and used, this embodiment of the invention can carry out automatic skin data capture, or it can be manual or semi-automatic skin data capture). The Air Drone has a transceiver that works in a manner known to those skilled in the art.

b. The Invention Water Drone:
 (i) Can examine and monitor the eyes of various types of fishes in bays, rivers, streams, lakes, seas, or oceans, either in fish farms or in the wild. It can look down on them or travel underwater with them.

Note: There are existing commercial battery-powered wireless water surface and underwater drones in the commercial marketplace which are equipped with cameras so one can see and record professional still underwater photos and WiFi live-streaming video to one's smartphone or VR Headset (although not for the purpose of the invention). In addition, new wireless underwater cameras that do not need batteries have been developed, which can take color photos even in dark underwater environments and transmit image data wirelessly through the water.[46]

[46] See https://scitechdaily.com/mit-engineers-build-wireless-underwater-camera-that-doesnt-need-batteries/.

(ii) Will have a transceiver that works in a manner known to those skilled in the art.

Camera(s) and sensors on the Invention Water Drone can capture, as part of the system of the invention and as a means to implement its methodology, the skin data of fishes (and other underwater animals) of various types (including without limitation fishes that are on fish farms or in the wild, be it in streams, rivers, ponds, lakes, seas, or oceans).

Dependent on how programmed and used, this embodiment of the invention can be automatic skin data capture, or it can be manual or semi-automatic skin data capture.

c. The Special Input Drone (i.e., Both the Invention Air Drone and the Invention Water Drone):
  (i) Can identify a specific animal by its unique biometric data as elsewhere described herein, if the animal has been previously identified by the invention (and if the animal's unique biometric data is visible). Hence, the invention can in a sense be used for contactless, non-tagged animal tracking as well as for animal health matters.
  (ii) Will have and use sensors to determine its distance from objects (including animals), both to navigate to avoid collisions and to perform its mission of collecting and monitoring animal Subject skin data.
  (iii) Will have the ability to operate in a manual or autonomous mode, with speed controls.
  (iv) Will have the ability to automatically return to base (so it does not crash or become lost before its energy source expires).
  (v) May or may not have lights on it (with various light functionalities, such as the ability to turn a bright light on-and-off, having a blinking light, et al.) for travel identification, assisting with better camera and/or sensor imaging to better observe animal Subjects, and/or performing certain skin tests on the animal Subjects' skin.

10. Will Use Edge AI or "Pure Cloud" for Processing Data.

The data may also be processed in the "unit" that remains with the controller of the Special Input Drone (assuming there is one).

The drone portion of the Special Input Drone can be powered/fueled by power sources/fuel sources known to those skilled in the art, including without limitation:
  a. For the Invention Air Drone: electric/battery (e.g., without limitation, a lithium polymer battery), electric/solar, hydrogen fuel cell, combustion (using, for example, without limitation, kerosene or gasoline), or tethered to a power supply.
  b. For the Invention Water Drone: electric/battery (e.g., without limitation, a lithium polymer battery), electric/solar, hydrogen fuel cell, combustion (using, for example, without limitation, kerosene and/or gasoline or other carbon-based combustible), water flows/currents, or tethered to a power supply.

Note: Invention Air Drones could fly over outdoor crowds of human Subjects in order to obtain various types of information on potential diseases carried by Subjects in the crowd, especially contagious diseases, as well as biological weapon and/or poisonous gas attacks, to use big data to measure the prevalence and spread of the disease or biological weapon and/or poisonous gas attack, as well as to use the collected data for other aspects of potential disease control (such as notifying individual human Subjects who may be individually identified as possibly having the condition) (all within the confines of whatever relevant laws are applicable).

For each of the input devices that are part of the invention (as described above and herein), the invention may optionally use an optional additional auxiliary input device that measures and collects human or animal body temperature data by means known to those skilled in the art. In one embodiment, this can use an electronic thermometer appropriate for the area of the human body part or animal body part from which the temperature will be measured (the "Auxiliary Input Device"). In an embodiment, are two versions of the Auxiliary Input Device: (i) a standalone Auxiliary Input Device, in which all functionality (e.g., temperature data measurement and collection, as well as transceiver and battery power) resides in the Auxiliary Input Device, and (ii) an Auxiliary Input Device that works wirelessly or by wire together the invention input device with which the Auxiliary Input Device is an additional auxiliary input device, in which some of the technology is in the Auxiliary Input Device, and some is in the invention input device, and they work together, with the Auxiliary Input Device piggy-backing off the transceiver and battery of the invention input device, et al.

Ideally the Subject's skin data and temperature data can be synchronized in time in a statistically meaningful manner by a means known to those skilled in the art (including without limitation the use of "if-then" and/or AI software in the cloud or "if-then" and/or EDGE AI software located in the EDGE) and the Subject's temperature data and the Subject's skin data may be cross-compared and correlated, and if statistically relevant can potentially clarify and strengthen "indications of Conditions" of the Subject, including the trends and the speed of the trends related thereto, and thereby allow for potentially better facilitation of both acute and long-term treatment and therapy adjustments).

F. Cameras on Input Device(s)

Like computer chips before them, cameras are becoming better, cheaper, and smaller every year.

1. Cameras.
  a. Invention Camera-Types. The types of cameras or camera-like devices that are part of the invention and used by it are set forth and generally described in Schedule Q attached hereto. That said, other similar stand-alone digital cameras sending data through their own or separate transceivers, as well as different cameras not described in Schedule O can be used.

There are, for example, various ultrasonic cameras used in dermatology, including wireless ones.

In addition, for example but without limitation, lidar systems are currently used to measure the distance between objects with light. They send out laser beams and measure returning light to calculate distance, speed and trajectory.

One way to add 3D imaging to standard sensors is by adding a light source and a modulator that turns the light on and off millions of times every second. The variations in the light can be used to calculate distance. Existing modulators, however, require such large amounts of power that they become impractical for everyday use.

Using a simple acoustic modulator composed of a thin wafer of lithium niobate coated with transparent electrodes reduces the problem. Lithium niobate is piezoelectric, meaning that when electricity is introduced through the electrodes, the crystal lattice at the heart of its atomic structure changes shape. It vibrates at high, predictable, and controllable frequencies, and, as it vibrates, it strongly modulates light. With the addition of polarizers, the new modulator effectively turns light on and off several million times a second. Also, the geometry of the wafers and the electrodes defines the frequency of light modulation, so the frequency of modulation can be fine-tuned. Further, compared to other alternatives the method is very energy efficient.

The piezoelectric effect creates an acoustic wave through the crystal that rotates the polarization of light in desirable tunable and usable ways. Then a polarizing filter is carefully placed after the modulator that converts this rotation into intensity modulation—making the light brighter and darker—effectively turning the light on and off millions of times per second.

This technology can be integrated into a proposed system that uses off-the-shelf cameras, such as those used in cellphones and DSLRs. The device makes it possible to obtain 3D data from technology that, on its own, is capable of seeing only in two dimensions.[47]

[47] https://www.photonics.com/Articles/Modulator_Enables_Simple_Cameras_to_Capture/a67897; see also https://www.photonics.com/Articles/Integrated_Laser_on_Lithium_Niobate_Chip_Supports/a67945.

Another way to greatly reduce the size of a camera and use it to take 3D images is to use a lensless camera. Scientists applying machine learning have come up with a way to take the blurred mess captured when using an image sensor without an attached lens and turn it into a discernible image, potentially opening the path to ultra-compact cameras as well as offering 3D and post-focus capabilities.

Typically, an image sensor works behind a lens: Light is captured and focused on the sensor, which can then provide a pixel-by-pixel image to the connected system.

Using the sensor behind a thin mask usually produces nothing more than a colorful smudge. That smudge, however, scientists have found, has enough information in it to recreate the original image as though a lens had been in place. Previous work has leaned on convolutional neural networks, with mixed results. However, employing a vision transformer (ViT) created far clearer images than previous approaches and in a fraction of the time, allowing for real-time image capture and processing.

Lensless cameras can become ultra-small. Scientists have produced a one-pixel wide camera image in 2013, and expect with this new approach of using an array of vision transformers to go to the micron level. Cameras may be able to go so small as to be invisible.

Miniaturization is not the only advantage of the lensless camera. In addition, the underlying dimensionality of captured optical information by the lens-less camera is greater than two, which makes one-shot 3D imaging and post-capture refocusing possible.[48]

[48] See https://www.hackster.io/news/a-lens-free-camera-passed-through-a-vision-transformer-could-unlock-new-forms-of-photography-2ee8f2df99c1.amp; see also https://petapixel.com/2022/05/04/newly-developed-camera-can-take-in-focus-photos-without-a-lens/.

Also, metalens technology continues to develop, and new compact cameras have been designed that eliminate the typical bulk of optics.

Instead of using traditional glass or plastic optics, metalenses instead use nanostructures to focus light. Since they work on a single surface, they do not require any kind of optic and can remain flat. The metalens array is integrated directly on the CMOS image sensor and fixed by an optically clear adhesive tape.

Princeton and University of Washington researchers have managed to shrink a metalens down to the size of a grain of salt, and the lens was still able to produce surprisingly high quality images.

Using metalenses to create wide-angle cameras have recently been successful. By using an array of metalenses that were each carefully tuned to focus on a range of angles, which allowed each lens to clearly image part of a wide-angle scene, a final wide-angle image scene was created by combining the clear angle images together. The final "stitched together" wide-angle image had no degradation in image quality.

Thanks to the flexible design of metasurfaces, the focusing and imaging performance of each metalens can be optimized independently. In addition, the array can be manufactured using just one layer of material, which helps in keeping costs down.

Researchers using nanofabrication to create a metalens array that they mounted directly to a CMOS sensor were about to create a planar camera measuring about 1×1×0.3 centimeters. A similar, perhaps a slightly larger camera can be mass-produced and deployed in a number of devices, including smartphones.[49]

[49] https://petapixel.com/2022/04/14/compact-wide-angle-metalens-camera-eliminates-bulky-glass-optics/.

Further, using the programming language Python and a Hasselblad H6D, it is now possible to obtain 100 megapixel images that can be stitched together for a final stitched image of 925,000 pixels wide and 775,000 pixels tall with a resolution of 5 microns. A resolution of 5 microns puts the pixels in the digitized image at a smaller size than that of a human red blood cell.[50]

[50] https://fstoppers.com/education/how-capture-717-billion-pixel-photograph-601147.

Also, there are neuromorphic vision sensors. Neuromorphic vision—computer vision based on event-based cameras—may be the next direction computer vision takes. Neuromorphic vision detects changes in the scene dynamic rather than analyzing the entire scene continuously, and in doing so can save a tremendous amount of power and reduce latency compared to systematic acquisition at a fixed frequency. Event cameras of today are simply an improvement of original research devices developed as far back as 2000.[51]

[51] https://www.eetimes.com/a-shift-in-computer-vision-is-coming/.

b. Known Condition or Risk-for-Known-Condition.

Envision a person with an identified/diagnosed specific health condition (e.g., without limitation, diabetes, or high blood pressure) or at high risk for a specific health condition. That person would want to use the invention with an input device with a camera that could monitor them for that specific health condition. They could simply obtain an input device with an appropriate camera and the rest of the invention would function as it does, although it could specifically focus on their particular health condition of concern, while still "looking" for new potential skin health conditions.

[For example, but without limitation, a person with a diagnosed glucogonoma pancreatic tumor would want an input device with a camera that could examine and monitor parts of their skin that indicate a scaly rash on their buttocks, formally known as necrolytic migratory erythema (which usually signals a glucogonoma pancreatic tumor). The reverse is true as well: a person with indications of a scaly rash on their buttocks may also have or should beware of a getting glucogonoma pancreatic tumor.]

c. Cameras and Sensors Used for 3D, VR and AR.

The embodiment uses sensors such as LiDAR (a form of LiDAR scanner is currently found in the iPAD Pro 2020, and one or more of the versions of iPhone 12), which LiDAR scanner can accurately judge distances and therefore depth, and allows for improved augmented reality, and lasers. A laser-powered 3D camera is currently found in one or more of the versions of iPhone 12.

2. Remote Control Potential by Professional of Invention Input Devices/Cameras (Hand-Off).

The invention's input devices/cameras, in certain modes, which are examining and reviewing the skin of Subjects, may be controlled remotely by Professionals.

One type of invention input device can have either one, or more than one, type of camera on it, with each type of camera allowing for the capture of data from different targeted parts of a Subject's skin. Various types of cameras used as a part of the invention, without limitation, are set forth in Schedule O.

If additional Subject skin data is needed (more than can be captured on an input device with its camera(s)), the same input device with a different type of camera or cameras can be used.

For example, without limitation, there are many different types of cameras that can work together with an iPhone, as set forth in Schedule O.

3. Use of Smartphone Cameras for Clinical Data Acquisition for Teledermatology: The Need for Appropriate Calibration to Ensure Accurate Objectivity.

Today's AI-powered filters, such as the built-in ones on Instagram and Facebook, do a decent job of adjusting contrast and lighting and even adding depth-of-focus effects to simulate an expensive lens.

Indeed, use of smartphone cameras attached to dermatologic imaging systems enables the acquisition of high-quality images of the skin in a simple and affordable manner, given that smartphones are convenient and portable and their wireless connection provides for an easy Internet connection.

Use of smartphone cameras for clinical data acquisition for teledermatology, however, without adequate information of the quality of images can compromise data accuracy and repeatability. Calibration of a smartphone's camera is essential when extracting objective data from images.

It is well-known that two different cameras, or even the same camera with different settings, give different images for the same scene, which are possibly different to those perceived by a human's visual system.

One reason is the responses of the camera sensors vary from one camera to another. The red, green, and blue (RGB) values given by any imaging system are device dependent, and are different from the responses of human retina cells, and subsequent interpretation by the human brain. Also, camera makers have their own camera-specific and proprietary imaging processing algorithms, including autofocus algorithms that attempt to automatically enhance the perceptual image quality of the images. Autofocus mode adds lack of control and introduces uncertainty of color reproductions of clinical images obtained with different smartphones.

Accordingly, it is important to control for a camera's type and lighting levels when extracting objective data, so when comparing data an "apples-to-apples" comparison can be made. Appropriate compensation must be made for pictures taken with different cameras if they are not calibrated and they have different pixel size, sensor size, sensitivity, and optics.

The application of white balance and color correction to each image obtained under certain illumination conditions and with one specific camera is a standard procedure to obtain the color ground truth of the scene being photographed. Any differences between lighting levels and camera types tend to be significantly minimized (but not made a perfect match) after cameras are calibrated.

Overall, a smartphone's camera calibration is essential when comparing images of areas of skin obtained with different smartphones and/or lighting levels by means of objective metrics.

An embodiment detects or is otherwise told the specific type of camera (and or smartphone or its equivalent) from where Subject skin data is coming, and equalizes calibration and light as appropriate and to the extent necessary, in a manner known to those skilled in the art, so meaningful objective data comparisons can be made for the purpose of the invention. This calibration can be done, for example, by maintaining a database with information from each of a plurality of different cameras that are used to obtain the images or videos.

XIII. AR VISUAL MARKS AND AR AUDIO NOTES/MESSAGES GENERATED, ACCESSED, AND TRANSMITTED BY THE PRESENT APPLICATION

The invention's AR visual marker and audio note/message system uses:

A. System Input.
1. a method or methods to identify, target, and acquire various types of digital data on selected Subject potential skin conditions or skin-related conditions on one or more unique Subject skin sites of interest (a "Unique Skin Site"). The Unique Skin Site targets may include, without limitation, an indication of a suspicious or an existing skin condition or skin-related condition of a Subject, such as, without limitation, skin rashes, skin lesions, skin color abnormalities, skin topographical abnormalities, skin texture abnormalities, skin tissue burns, skin temperature abnormalities, and/or skin puncture wounds.
2. a method or methods to capture a digital image and/or digital video images of the identified and targeted Subject potential skin conditions or skin-related conditions on Unique Skin Site, be it an optical image or video or a thermal image and video, or alternative type of image, and skin data with respect thereto; and
3. a method or methods to identify, target, and capture certain unique biometric data patterns of the Subject, specifically those of the Subject's skin pores/hair follicles, blood veins, and/or thermal temperature distribution, or some combination or permutation thereof, from a Unique Skin Site, which biometric data from the Unique Skin Site is located on, near, or surrounding the targeted Subject potential skin condition or skin-related condition on which digital data has been acquired (the "Skin Image Patterns").

Similar to face recognition methodology, the invention captures, analyzes, and compares Skin Image Patterns, and uses computer-generated filters, by using "deep learning" and/or potentially other artificial intelligence methods and techniques, to transform Skin Image Patterns into numerical expressions [which are essentially x, y, z coordinates] (the "Numerical Expressions").

B. System Processing and Data Storage.
1. software to determine the similarity between two Skin Image Patterns, using the Numerical Expressions that can be computed to determine their similarity.

The data about the Unique Skin Site (i.e., the Numerical Expressions) is distinct from a photograph because the Numerical Expressions data is designed to only include certain details that can be used to distinguish one Unique Skin Site from another. The Numerical Expressions data will be stored in a Numerical Expressions Skin Recognition Registry (the "Database"). If you enter a photograph (or data about a skin site) into the Database, it will locate any matching Numerical Expression set that it has stored there.

C. Generation and Re-Location and Re-Generation of AR Visual Marks and/or AR Audio Notes/Messages.
1. a portable device to generate, based on the Numerical Expressions in the Database, and/or to re-locate and re-generate, based on the coordinates in the Database:
   a. One or more AR visual marks ("AR Visual Marks"), and/or
   b. One or more AR audio notes/messages ("AR Audio Notes") on specifically selected areas of the skin (including fingernails and toenails) of a Subject (the "Skin") (or in the case of an AR Audio Note, alternatively connected/anchored mathematically to the AR Visual Mark), in which:
      (i) The AR Visual Mark coordinates (e.g., x, y, z and potentially a date/time) of each AR Mark placed on a Subject's Skin) (the "AR Mark Coordinates"), and
      (ii) The AR Audio Note coordinates (e.g., x, y, z and potentially a date/time of each AR Audio Note placed on a Subject's Skin or attached to an AR Visual Mark) (the "AR Audio Note Coordinates"), are each precisely correlated with the Numerical Expressions in the Database of a Subject Skin Image Pattern.

The AR Mark Coordinates and the AR Audio Note Coordinates will each be stored in an AR Map Registry (the "AR Mark Map Registry").
   a. When displayed, each AR Visual Mark on the Subject's Skin will be displayed in a manner in which it does not change in size or location and is "anchored" to the specific coordinates of Numerical Expressions.
   b. When "accessed", each AR Audio Note on the Subject's Skin or attached to an AR Visual Mark will be accessed in a manner in which it does not change in location and is "anchored" to the specific coordinates of Numerical Expressions.
2. a portable device that enables easy re-identification and reauthentication with precision of same specific area of the Skin of the Subject (i.e., an image of the same area of the Subject's Skin), and the re-generation of the AR Visual Mark "anchored" to that same specific area of the Subject's Skin on which it was initially registered pursuant to the AR Mark Map Registry, and/or the re-generation of the AR Audio Note "anchored" to either:
   a. That same specific area of the Subject's Skin, or
   b. The AR Visual Mark, on which it was initially registered pursuant to the AR Mark Map Registry, all of which is carried out using one or more computers using software known to those skilled in the art.

The system as described by the invention will operate in real time, and in certain configurations may be used remotely (i.e., whereby the Subject is in one location, and the person and/or robot or computer controlling the application of the AR Visual Mark and/or AR Audio Note is viewing and/or hearing any of the foregoing at a distance from the Subject).

It is an object of the present invention to use a computer to enable its user to create a non-physical AR visual mark or marks and/or a non-physical AR audio note or notes on specifically targeted areas of a Subject's Skin, which areas may be indicated and potentially identified through the examination of Skin, by a human (the Subject himself or herself, or a medical professional), medical device, computer device, or computer system, or some combination thereof, through the use of a portable or mobile wireless computer device or computer system, together with peripherals that work with other parts of the invention.

It should be understood that the devices performing the various functions above could all be in one device, such as a smartphone (with appropriate attachments if necessary) or in separate devices in which relevant data is transferred wirelessly or by wire from device-to-device to enable the necessary functionality of a given device.

It should also be understood the operation of the device or devices could be shared remotely, for example but without limitation, by a Subject-user physically holding a device, and a health care professional instructing the Subject-user what to do and potentially operating the device remotely, and receiving images and videos and other data from the device remotely.

It should further be understood the operation of the device or devices, with the prior consent of the Subject, could be performed autonomously by pre-programming and/or by robot or computer. For example, but without limitation, the device or devices could be used in a robot-assisted or robot-autonomous review, follow-up review, biopsy, or surgery, related to a specific part of a Subject's Skin or another related part of a Subject.

D. Workings of the Invention. The Invention Uses a:
1. portable 3D scanner/smartphone camera or similar device using a distance measuring technology or methodology (such as using a physical "guide"/i.e., a guiding aperture set for a particular physical distance, or lidar, other kind of distance measuring technology), to target the Unique Skin Site specifically. The targeting is performed by:
   a. the Subject himself or herself, consciously with full awareness, using the Device, with or without the remote assistance of a health professional, to target one or more areas of the Subject's skin (including fingernails and toenails);
   b. the Subject himself or herself, with prior consent, but unaware, using the Device in a preset automatic mode, to target one or more areas of the Subject's skin (including fingernails and toenails);
   c. A health care professional, remotely or otherwise, using the Device, to target one or more areas of the Subject's skin (including fingernails and toenails); and/or
   d. An autonomous robot, remotely or otherwise, using the Device, to target one or more areas of the Subject's skin (including fingernails and toenails), using:
      (i) software, known to those skilled in the art as existing or creatable, focused on identification of either (x) a particular type of skin condition, indication, or abnormality; or (y) multiple types of skin conditions, indications, or abnormalities; and
      (ii) hardware, known to those skilled in the art as existing or creatable, to operate the foregoing software, to
         (x) "attach" and "anchor" to the targeted Unique Skin Site a new AR visual mark and/or audio note/message, and
         (y) display or provide access on the targeted Unique Skin Site (through the use of hardware and software known to those skilled in the art) the new AR visual mark and/or the new AR audio note/message; and (z) relocate and re-display a pre-existing AR visual mark and/or AR audio note/message (for, without limitation, "auditing" the Skin target virtually marked for separate confirmation, or determining changes in the Skin target virtually marked over time), using a:
  (i) portable 3D scanner/smartphone camera or similar device using some distance measuring technology (such as using a physical "guide"/i.e., a guiding aperture set for a particular physical distance, or Lidar, or an alternative measuring technology), and/or
  (ii) portable device that can generate near-infrared rays (which make blood veins appear as a black pattern) which contrast in color with the skin above, and/or
  (iii) portable infrared camera, to acquire, with appropriate magnification, a:
    (x) two-dimensional or three-dimensional color and/or grayscale optical image, and/or
    (y) thermographic image, or video of a specific area of the skin of a human or animal subject (the "Subject"), and the unique:
  (i) skin pores'/hair follicles' pattern, and/or
  (ii) blood vein pattern, and/or
  (iii) thermogram heat pattern, and/or
  (iv) some combination of (i), (ii), and (iii) above for double-or-multiple identification
and/or authentication,
on and/or surrounding the Unique Skin Site, through the use of software known to those skilled in the art, map and register this biometric pattern coordinate data (e.g., x, y, z, and date/time) (the "Biometric Coordinate Data") in a biometric map registry (the "Biometric Map Registry"), stored locally, on the Device, and/or in the cloud.

Note: Subject can move and not remain steady and device-holder can move and not remain steady. This is intended to make Subject Skin care and "procedures" better, faster, and cheaper.

This is based on the inventor's recognition that non-physical AR virtual marks on specifically selected areas of Skin of the Subject have many advantages over plain physical marks per se, including without limitation:

1. A physical skin mark is disfiguring; an AR virtual mark is not (as it cannot generally be seen).

In an alternative embodiment, a special code in the software is used to control who can view the AR mark, to comply with confidentiality rules such as HIPPA.

2. A physical skin mark is based on direct Subject skin contact may be unsterile; an AR virtual visual mark is not based on direct Subject skin contact and is sterile, as the AR virtual visual skin mark is not physical.

3. A physical skin mark may disappear for various reasons, including skin cells on which it is placed dying and new skin cell growth erasing it, sterile solution erasing it, it washing off, et al.; an AR virtual visual mark will not disappear in any of those ways. Physical notations on a notepad or audio recording device or other device separate from the Subject to whom they refer may get lost or misapplied to the wrong Subject; this cannot occur with an AR virtual audio recording directly attached/anchored to a Subject or attached or anchored to an AR virtual visual mark attached/anchored to a Subject.

4. A physical skin mark of the type used in breast biopsies may migrate for various reasons; an AR virtual visual mark will not migrate or move from its original location. The same is true of an AR virtual audio note; it will not migrate or move from its original location.

5. A physical skin mark does not tend to lend itself to precise objective measurement, whereas a computer-generated AR visual mark (based on computer mathematics) does.

6. An AR visual mark can easily provide 3D coordinates and volumetric information in a manner a "dumb" physical clip tag of the type used in breast biopsies and breast surgeries cannot.

7. An AR visual mark lends itself more easily to recording and tracking/locating the AR I visual mark itself, including the Subject on which it was applied, the date of its application, and the identity of who applied it, than is the case with a plain physical mark. The same is true of an AR audio note/message.

8. An AR visual mark is arguably more electronic records-friendly than is the case with a physical mark, and the AR visual mark's underlying data can be wirelessly transferred to an electronic records file wirelessly. The same is true of an AR audio note/message.

9. An AR visual mark and the data underlying it being digital in nature with coordinates anchored to the Unique Skin Site can be communicated to and with other computers/robots that assist in the performance of or autonomously perform related functions at the Unique Skin Site, such as robot-assisted or robot-autonomous biopsies and surgeries, and can allow for remote viewing of the AR visual mark at and with the target at the Unique Skin Site in real time, arguably in a manner in which a physical mark cannot. The same is true of an AR virtual audio note, to the extent audio access is possible through, for example but without limitation, NLP.

10. An AR visual mark can at any time immediately be (i) toggled on and off, and/or (ii) erased, with no trace on the Skin of the Subject, which is not true of a physical skin mark. The same is true of an AR audio note/message.

11. An AR visual mark and the data underlying it, when a second AR visual mark with underlying data is added, can automatically identify, quantify, and thereby monitor changes in target at the Unique Skin Site of a Subject, while a physical mark can only passively assist in that regard.

12. An AR visual mark and the data underlying it can assist with treatments and/or "procedures" related to the Subject's skin per se or other selected areas of the Subject (for example, without limitation, identifying and/or virtually marking specific areas of the Skin of the Subject for incisions for, without limitation, micro, regular open, arthroscopic, or laparoscopic surgery). Similarly, an AR audio note can assist with treatments and/or "procedures" related to the Subject's skin per se or other selected areas of the Subject (for example, without limitation, by the Subject or a medical professional making audio observations regarding the skin appearance and condition, et al.).

13. An AR virtual visual mark can precisely and objectively virtually mark a target at the Unique Skin site of the Subject, in two dimensions or three dimensions, in the exact two dimensional or three dimensional shape and size of the target at the Unique Skin Site, at the exact date/time of the generation of the AR virtual visual mark thereon, and identify who applied the AR virtual mark thereon and more information and data in the virtual mark itself; most or all of the foregoing cannot be done with a physical skin mark.

14. An AR visual mark of a target on a Unique Skin Area allows for automatic "labeling" for AI purposes; a physical skin mark does not allow for such automatic "labeling" for AI purposes (including without limitation Al "training"). An AR virtual audio note regarding a target on a Unique Skin Area allows for another type of automatic "labeling" for AI purposes (including without limitation Al "training").

15. An AR visual mark lends itself to telemedicine in many ways in which a physical marker does not.

The same is true with regard to an AR virtual audio note/message.

Attributes of the AR visual marks and AR audio notes/messages generated, accessed, and transmitted by the present application include:

E. AR Visual Mark Attributes.

The AR visual mark itself can be in many sizes, shapes, designs, and/or colors (i.e., for example but without limitation, big or small, round or square, a fleur-de-lis, target pattern, a pyramid, or a corporate logo, and, for instance, in colors red, yellow or blue).

1. AR Visual Marks with Bullseye Target-Shaped Concentric Rings for Location and Measurement, et al.

For example, but without limitation, there could be AR visual bullseye target-shaped concentric circles used for marking the precise location of a Subject's targeted skin condition, with the precise distance between each of the target rings known, providing the ability to, at one or more later subsequent times, determine if there has been a change in 2D size of the skin condition targeted on the Subject's skin, either by passively viewing the AR visual bullseye target-shaped concentric circles and the measurement Indication thereby provided or having such measurement made automatically by the invention device.

2. AR Visual Mark Amorphous Shape for Location and Measurement, et al.

The computer software can program the AR visual mark to take on a 2D amorphous shape, for example but without limitation, surrounding one or more exact amorphous targets of a Subject's skin discoloration and/or lesion (e.g., the skin discoloration, color, and/or shape of a mole). Using such a 2D amorphous-shaped AR visual mark, which outlines and measures the exact outline/circumference measurement and size of a targeted skin condition at a fixed point in time, one can determine over time, by visual and/or mathematical comparison, an objective measurement of the continued growth or remission of Subject's targeted skin condition.

3. AR Visual Mark Using 3D Volume for Location and Measurement, et al.

A specific 3D volume of an AR visual mark on a specific area of a Subject's skin could be used to reflect, for example but without limitation, the precise/specific volume of a Subject's skin condition targeted skin lesion or "growth" at the time of the application of the 3D volume AR visual mark. For example, the AR visual mark can be programmed to take on, for example but without limitation, a pyramid or "mountain-shaped" 3D voluminous form, directly on or surrounding one or more exact targets of the Subject's skin, and volumetrically display the volumetric size of the Subject's skin lesion or growth (either rising above the skin level, or both above and below the skin level), allowing one to determine over time, by visual and/or mathematical comparison, an objective measurement of the continued growth or remission of Subject's targeted skin condition.

4. AR Visual Mark as a Virtual Bar Code or Virtual QR Code for Location and to Obtain Related Information by a Means "Anchored" to the Subject.

The AR visual mark could be in whole or part a bar code or QR code or similar type code (which could be an encrypted code) (collectively, the "Code"), that would allow the "visual Code reader" to use the barcode, QR Code, or similar code to obtain additional information once the Code is scanned (just as QR Codes can be scanned off TV screens). The Code may include one or more AR audio notes/messages. By attaching the Code directly to the skin of the Subject there is an assurance the correct information is being used with the correct Subject (i.e., no mismatching of file data).

5. AR Visual Mark Use of Colors for Location, Identification, and Measurement.

The AR visual mark could be attached to a targeted area of skin on the Subject, for example but without limitation, in the color red, and at the same time or a future time, another AR visual mark could be added in a different color, say blue. This could continue on and on as makes sense for the use of the AR visual marks.

The different colored AR visual marks could be used to measure, for example but without limitation, a skin lesion's growth or shrinkage by virtually marking the lesion in different colors at two separate dates and times. In many ways the use of different colors for AR visual marks is similar to the user of the Microsoft computer software application "Word", whereby if you want to compare two documents the program shows you in one color the revisions made by one reviser compared to the original document, and different revisers can have different colors showing their respective changes. The inventor envisions the invention can be programmed to do this automatically if so selected.

With respect to AR visual marks of different colors, for example:

(x) If the initial AR visual mark on the Subject was in the color red, and a subsequent new AR visual mark on the Subject was in the color blue, where the AR visual marks overlap could be in the color purple, which could easily visually show a change in the targeted spot on of skin of the Subject over time (the time difference being the time from the placement of the initial AR visual mark on the Subject to the time of the placement of the new AR visual mark on the Subject. In other words, colored AR visual marks as envisioned by the inventor can be used like Venn diagrams with color.

(y) For ease for the viewer, different AR visual mark colors on the Subject could be used whereby one AR visual mark color represents one skin issue or potential condition, and a different AR visual mark color represents a separate and distinct skin issue or potential condition.

6. Toggling the AR Visual Mark On-and-Off (i.e. Visible and Invisible) on the Skin of the Subject.

The [Imaging Device/AR Visual Mark-Mark Viewer/Transceiver] (described below) will have the capacity to allow the user to toggle the AR visual mark on-and-off (i.e., visible and invisible) on the virtually marked area of skin of the Subject, and visually expand the size of the image.

7. Ability to Transmit the Digital AR Visual Mark Data.

The [Imaging Device/AR Visual Mark-Mark Generator/Transceiver] (described below) will have the capacity to allow the user to electronically transmit the digital AR visual mark data (which may or may not be linked to the digital AR audio note/message data) to a separate area of digital storage (other than the Device itself), be it a cloud, edge storage, or local storage in another device. This allows for teledermatology, among other things.

8. Manual or Automatic Application of the AR Visual Mark on the Skin of the Subject.

The AR visual mark can be applied "manually" (i.e., free form) by the Subject, medical professional, just like a computer drawing program allows, or automatically, where "aspects" (for example color and shape, et al.) of the AR visual mark are preselected (from a menu of choices). The AR visual mark can also be applied automatically/autonomously by a computer and/or robot using AR visual marks that are preselected for various purposes (e.g., without limitation, automatically marking all of the Subject's targeted moles with a bullseye target color green AR visual mark).

F. AR Audio Note/Message Attributes.

An AR audio note/message or notes/messages could be attached to the same general specific area of skin on the Subject as the AR visual mark, or to the AR visual mark itself on that specific area of skin.

1. Natural Voices or Artificial-Synthetic Voices/Sound Input.

The AR audio note/message (i.e., sound input) attached to either:
   (a) an AR visual mark, or
   (b) a specific area of skin on the Subject, can be a natural human voice, such as, for example but without limitation, that of the Subject or a health care professional, or the artificial-synthetic voice of a robot or computer, in which either:
   (c) a human selects what the robot or computer "says/ inputting AR audio note(s)/message(s)" (for example from a menu of predetermined selections), or
   (d) the artificial-synthetic voice is automatically/autonomously generated by the computer or robot based on, for example, without limitation, chatbot pre-programming,
for example, without limitation, with regard to a Subject's targeted skin lesion or skin puncture wound.

For example, the AR audio note/message can be, without limitation:
   (x) The voice of the Subject describing his or her skin issue and/or potential condition, either independently or based on being coached by a health care professional or an AI chatbot (i.e., e.g., a question-answer interaction), either near the Subject or remotely at-a-distance, and/or
   (y) The voice of a health care professional or AI chatbot (i.e., e.g., describing the Subject's skin issue and/or potential condition, and/or health care instructions with respect thereto, et al.), either near the Subject or remotely at-a-distance.

2. Human or Natural Language Processing (NLP)/Sound Output.

When the AR audio note/message is "read" (i.e., the sound output), it may be heard by, for example but without limitation,
   (a) the Subject,
   (b) a health care professional, and/or
   (c) a computer or robot, either near the Subject or remotely at-a-distance. If by a computer or robot, there may simply be an exchange of the software code containing the AR audio notes/messages, since there may be no need to "hear" such information out loud (by that machine listener) in order to receive the relevant output AR audio data.

3. Toggling the AR Audio Note/Message On-and-Off (i.e. Audible or Inaudible).

The [Speaker Device/AR Audio Note/Message Player/Transceiver] (described below) will have the capacity to allow the user to toggle the AR audio note/message on-and-off (i.e., audible and inaudible).

4. Ability to Electronically Transmit the Digital AR Audio Data.

The [Imaging Device/AR Visual Mark-Mark Generator/Transceiver] (described below) will have the capacity to allow the user to electronically transmit the digital AR audio data (which may or may not be linked to the digital AR visual mark data) to a separate area of digital storage (other than the Device itself), be it a cloud, edge storage, or local storage in another device. This allows for teledermatology, among other things.

5. Manual or Automatic Application of the AR Note/Message on the Skin of the Subject and/or on the AR Visual Mark on the Subject. The AR audio note/message can be applied manually or "automatically" by the Subject, medical professional, where manual is normal speech, and automatic is where the user makes use of preselected audio notes/messages (from a menu of choices). The AR note/message can also be applied automatically/autonomously by a computer and/or robot using AR audio notes/messages that are preselected for various purposes (e.g., without limitation, automatically AR "audio noting" each of the Subject's targeted moles with a preselected AR audio note/message for a mole of that type/size).

G. Use of the AR Visual Mark and/or AR Audio Note/Message for

Authentication and Identification. The AR visual mark and/or AR audio note/message on and attached to a specific area of skin of the Subject (via the means described in the instant invention) can be used to authenticate and identify:
   a. The Subject, since the (i) skin pores'/hair follicles' pattern, (ii) blood veins pattern, and/or (iii) thermal pattern, on a specific area of the skin of each Subject is unique, and without identification of the mathematical data related to one or more of the patterns, the AR visual mark and/or AR audio note/message should not "work" (as it will not be "anchored" to the relevant Subject targeted skin location); and
   b. The person, potentially, who attached the AR visual mark and/or AR audio note/message to a targeted specific area of skin of the Subject, since the AR visual mark and/or AR audio note/message allows for add such identification and other information as described elsewhere herein.

The AR can also be used with a holograph image, obtained by a holographic camera. The hologram of the Subject need not be of the entire Subject's body, but may be only of a relevant portion of the Subject's body, such as, without limitation, a head, arm, leg, hand or foot containing a or the potential or actual skin condition of the Subject. If the holograph of the Subject has sufficient visual clarity, the device with the Subject AR tag or tags (visual AR or audio AR) and Subject anchor data storage for the AR tag or tags should be able to display/play the AR tag or tags on the holograph of the Subject (wherever that holograph may be). This could occur in real time or delayed time.

In essence, the Subject AR tag or tags should be able to—in a sense—"travel" with the holograph of the Subject (although the AR tag itself and the data regarding what and where it anchors to on the Subject, etc. remains in the device used by the health professional). In actuality the AR tag, anchoring and other data is simply regenerated on the Subject holograph.

The AR tag itself and the data regarding what and where the AR tag anchors itself on the Subject is digital data that can be stored, copied and easily moved electronically (with appropriate privacy considerations) by wired or wireless means to various locations and various devices.

While the health professional (human or robot) cannot directly apply a new AR tag (visual or audio) onto a holographic Subject, the health professional can see or hear the visual/audio AR tag on the holographic Subject.

The health professional (human or robot) can indirectly apply a new or updated AR tag (visual or audio) to the real-life Subject through:

1. Instructing the Subject, or someone with the Subject, to make a new or updated AR tag (visual or audio) on the Subject (using a device available to the Subject or someone with the Subject, including a robot). If done in real time, the new or updated AR tag on the Subject (visual or audio) would appear on the Subject holograph being viewed by the health professional (human or robot). If done in delayed time, the new or updated AR tag on the Subject would appear on the Subject holograph for later viewing/hearing.
   a. The instruction to the Subject could come through a human or a "robot" (NLP).
   b. An audio instruction or new or updated audio AR tag for the Subject could be sent electronically to a device where the real Subject is for attachment to the real Subject.
2. The health professional (human or robot) could remotely (i.e., by remote control) make a new or updated AR tag (visual or audio) on the actual Subject (using a device available to the Subject or someone with the Subject, including a robot). If done in real time, the new or updated AR tag on the Subject (visual or audio) would appear on the Subject holograph being viewed by the health professional (human or robot). If done in delayed time, the new or updated AR tag on the Subject would appear on the Subject holograph for later viewing/hearing.
3. A device could be programmed at the location of the actual Subject to automatically make a new or updated AR tag (visual or audio) on the actual Subject (using a device available to the Subject or someone with the Subject, including a robot). If done in real time, the new or updated AR tag on the Subject (visual or audio) would appear on the Subject holograph being viewed by the health professional (human or robot). If done in delayed time, the new or updated AR tag on the Subject would appear on the Subject holograph for later viewing/hearing.

Some of the AR tags may outline the "wound" or infection or bruise or blemish, etc. and otherwise act as a form of measurement of the Subject's skin condition (2D outline, or 3D volumetric outline of the actual skin "condition", temperature through color of the skin "condition", etc.) in addition to identifying its physical location on the Subject. Subsequent AR tags on the same skin condition area of the Subject may be mathematically compared to prior AR tags on the same skin condition area of the Subject (both are digital data, so this is a mathematical computer comparison of the data between the two or more AR tags) to show a change of the skin condition of the Subject over time (through the computer mathematically comparing the AR tag data). Indeed, multiple (more than two) Subject skin AR tags over various intervals of time may be compared to illustrate the change in the skin condition of the Subject over the relevant period of time, and this data may be compared through the invention's AI software to see if the changes are occurring at a typical rate, etc. (using various appropriate comparisons).

An embodiment uses the AR tags being anchored to the unique skin pore pattern of each Subject near the site of the relevant skin condition of the Subject. However, other embodiments may use another appropriate mode of anchoring known to those skilled in the art.

The inventor believes that the collection of skin data in a similar way whereby the collection and analysis of the data, including a comparison of user skin trends over time, can reveal a number of significant "indications" that may play a role in a user's general health.

Also, it is an intention of the invention, through its use of "machine learning" and "deep learning" software, and other types of artificial intelligence, to uncover new correlations between and among skin data and general health.

The invention is also intended to enable the remote, at-a-distance, examination and evaluation of skin data, in real time, near-real time, or delayed time, by:
(i) The Subject alone working with [a computer system] (i.e., the Subject collects his or her own skin data), and/or
(ii) Health care professionals ("Professionals").

In addition, the embodiments describe, through monitoring skin and skin data, the invention's ability to:
(i) assist in overcoming the shortage of dermatologists and related limited resources to provide in-person patient total body skin examinations (or targeted parts thereof).
(ii) assist in identifying indications of various selected skin conditions that should be monitored and/or treated.
(iii) assist in monitoring various selected skin conditions over time, to assist in timely determining if they are improving or worsening.
(iv) assist in removing the concern of some patients regarding having "sensitive areas" of his or her body visually examined in-person in real-time by Professionals, whether or not of the opposite gender or otherwise, in a total body skin examination or with respect to a "sensitive area" (including, without limitation, genitalia).
(v) assist in determining the appropriate frequency for actual physical visits to the office of a dermatologist based on intake history and any prior examinations, together with a remote teledermatological total body scan examination (or part thereof), based on determining if a patient is potentially "high risk" due to, for example, a history of cancer, immunosuppression, indoor tanning, and/or blistering sunburns, as well as several other genetic parameters, thereby balancing time, risk-based resource management (including the time and office availability of dermatologists and related health care workers), and patient preference.
(vi) standardize and/or objectivize skin burn evaluations in real-time or near-real-time, allowing for timely treatment decisions by, for example without limitation, parents, fire fighters, ambulance personnel and other first responders, and others, for skin burns that may or may not be serious, and valid "apple-to-apple" comparisons between (i) separate patient total body skin examinations (or targeted parts thereof) over time, and (ii) patient total body skin examinations (or targeted parts thereof) as compared to other patient total body skin examinations (or targeted parts thereof), as well as standardized and objectivized skin burn healing evaluation.
(vii) standardize and/or objectivize skin puncture wound evaluations in real-time or near-real-time, allowing for timely treatment decisions by, for example without limitation, military soldiers in the field, police, first responders, construction workers, parents, first responders, and others, for burns that may or may not be serious, and valid "apple-to-apple" comparisons between (i) separate patient total body skin examinations (or targeted parts thereof) over time, and (ii) patient total body skin examinations (or targeted parts thereof) as compared to other patient total body skin examinations (or targeted parts thereof), as well as standardized and objectivized skin puncture wound healing evaluation.

(viii) with the Subject's prior consent, collect skin data from the Subject by means of which the Subject is:
  (a) not consciously aware, and has to make or makes no effort to assist in the collection of the skin data;
  (b) semi-consciously aware, in which the Subject has to make or makes limited effort to assist in the collection of the skin data; and
  (c) fully consciously aware, in which the Subject has to make or makes a fully conscious and active effort to assist in the collection of the skin data. Examples, without limitation, of item (vii)(a) (i.e., the Subject not being consciously aware) would be a Subject (who has previously provided prior consent):
    (x) Reading e-mails on the Subject's smartphone screen, while the Subject's camera, based on pre-programming (and with the ability to identify the Subject), collects skin data on the Subject's face, et al.; or
    (y) Glancing at or grooming himself or herself in a mirror, which is a "one-way mirror" with cameras behind it which, based on pre-programming (and a motion detector and with the ability to identify the Subject), collects skin data on the Subject's face and/or body et al.; or
    (z) In the shower, bathroom, on the outside edge of a dressing mirror, and/or in a dressing room, with cameras/sensors or a "camera/sensor strip" (in which the images and skin data collected would be stitched together by software known to those skilled in the art) on one or more walls, and possibly the floor and ceiling, and from one or more angles, which, based on pre-programming (and a motion detector and with the ability to identify the Subject), collect skin data on the Subject's face and/or body, et al.

An example, without limitation, of item (vii)(b) (i.e., the Subject being semi-consciously aware) would be a Subject (who has previously provided prior consent), knowing camera/sensors are there, randomly striking different poses in front of a full body mirror—e.g., doing a full twirl, without regard to making an effort to specifically display any particular area of the Subject's skin.

An example, without limitation, of item (iii)(c) (i.e., the Subject being fully consciously aware), is one in which the Subject, either alone or being coached by a chatbot or Professional, is making a fully conscious and active effort to assist in the collection of the skin data) by, for example, in front of a device camera/sensor, standing at attention for a given period of time, then turning 90 degrees clockwise for a given period of time, then turning 90 degrees clockwise again for a given period of time, then turning 90 degrees clockwise again for a given period of time, the lifting one's arms above one's head for a given period of time, and so on, so the device camera/sensor gets a full view and can collect skin data on all areas of the Subject's skin.

In other embodiments, the invention is intended to:

1. Identification Of Unique Biometric Markers of the Subject.

Identify unique biometric markers in the skin (for example, without limitation, fingerprints, palm prints, unique freckle patterns, unique skin cell patterns, or unique skin colors) of users, which may be used in a variety of ways as described herein. The use may be in identification and/or locating targeted areas on beneath the skin of the Subject for (i) accidents, (ii) human-only, robot-assisted, or robot-autonomous skin biopsies, (iii) human-only, robot-assisted, or robot-autonomous skin surgery, (iv) opening or locking doors, (v) computer logins, (vi) security identification, or (vi) other applications;

2. Invention AR Visual "Health Tags".

Allow a Subject to attach an AR visual "health tag" to their skin (similar to a physical identification dog tag, used in the military, but only a virtual hologram), which could be, without limitation, a standalone AR visual image of words or AR audio note/message, or could be, without limitation, a virtual QR Code or its equivalent that goes to a website with words and/or audio that lists the Subject's health history, current use of prescription medications, contact information for those the Subject designates as emergency contacts, the Subject's "health directives", the Subject's potential consent to donate the Subject's body parts in the event of the Subject's death, all of which can be easily updated, revised and/or removed. It should be noted if the AR visual and/or AR audio "health tag" is a QR Code or its equivalent that links to a website with the Subject's health data, the website could potentially answer verbal questions presented to it with audio responses whereby it essentially acts as a chatbot based on the manner in which the Subject's website is enabled and the content therein.

This AR visual and/or audio "health tag" could be used by ambulances and other first responders in the event of a health emergency, by doctors and others. The Subject literally always carries their health data and health directives with them (attached to their skin) at all times; and 3. Invention AR Visual and AR Audio Note/Message Recreational and Commercial Applications.

Allow for Subjects to, for a non-medical use, and instead for:

(x) Recreational Use. Recreational usage (e.g., but without limitation, an AR visual image and/or AR audio note/message party, similar to a costume party, where, for example but without limitation, the event attendees (with enabling consent of each other attendee) can see the AR visual images and/or hear the AR audio notes/messages of each of the other authorized attendees.[52]

[52] Snap, the Snapchat maker, has introduced a feature called Local Lenses that allows multiple people in the same physical area to engage in shared AR experiences.

Snapchat lenses are most definitely AR and are wildly popular. According to Snap, 200 million people use them every day, racking up six billion interactions. See https://www.fastcompany.com/90737627/snaps-ar-vision-is-about-spectacles-and-a-whole-lot-more.

(y) Commercial Use. The concept allows the Subject to self-experiment before changing a "look" or purchasing a product that will change the Subject's "look" and/or be "attached" to them (i.e., an area of their skin) in some manner (e.g., an AR visual purse hanging from the Subject's hand, or an AR visual necklace and/or or earrings, AR visual lingerie, et al.), by adding AR visual marks/images to themselves by the means described in the invention. Examples, without limitation, of (x) and (y) immediately above include:

(i) Hairstyles, facial hair, cosmetics, jewelry, eyeglasses, cosmetics, alternative skin features (for example but without limitation, a different sized virtual nose, or an AR visual tattoo or tattoos); and/or (ii) Dynamic/moving AR visual marks/features such as, without limitation:
  (x) A winking eye, and/or
  (y) A tongue being stuck out, and/or
  (z) Dynamic AR visual marks/images that move in synchronization with music.

Vendors of all types (e.g., cosmetics, jewelry, purses, lingerie, et al.) may provide advertisements whereby their products are provided as AR visual images that Subjects can attach to targeted areas of their skin to allow the Subject to self-experiment, at-a-distance without the actual physical product, before changing a "look" or purchasing the instant product. One of the first rules of marketing is to put the product in the potential consumer's hands, and the invention allows for and uniquely enables exactly that. For example, Loreal's You cam app allows the customer to try out cosmetic products with the help of a smartphone, but through a different methodology than that proposed by the invention. Ultimately, vendors may sell or license some of the AR visual and/or AR audio notes/messages themselves, which the vendors allow consumers to sample. For instance, as in the early days of software, "time bombs" can be placed on the software with the AR visual and/or AR audio notes/messages so access to the software expires in a certain period of time unless purchased.

4. Attaching AR Virtual Audio Messages to Oneself.

Allow for Subjects to, for a non-medical and instead a recreational usage, playfully add AR virtual audio messages to themselves (including without limitation, spatial audio), with which the voices and sounds can vary based upon and according to the specific place on the skin of the body of the Subject, and the Subject's place on a video screen if the Subject is at a distance, by the means described in the invention in the form of, for example but without limitation:
  (i) A piece of music, and/or
  (ii) A sound (for example but without limitation, a dog barking or cat purring),
and/or
  (iii) A message in the Subject's voice or in the voice some other person.

It should be noted that in all of the foregoing in parts A, B, C and D immediately above, the relevant mathematical data can be encrypted whereby each Subject can determine who or what (in the case of computers and/or robots) other than the Subject can view and/or hear such added AR visual marks or features and/or AR audio notes/messages (which permission the Subject can easily revoke, and which AR visual marks or features and/or AR audio notes/messages the Subject can easily remove from himself or herself or their animals at any time).

XIV. THE NON-USER INPUT PORTION OF THE INVENTION: THE CLOUD AND THEREAFTER

The non-end user input portion of the System (the end on which the static images or streaming video of areas of skin of the Subject are received) is initially transmitted to the Subject's account in a cloud (the "Cloud"), where the skin data from the Device resides.

In the Cloud, depending on the Subject's application software pre-specifications:
1. The Subject's skin data is forwarded to the computer of the Subject's pre-selected Professional, in real-time, near real-time, or delayed time, for examination.
2. The Subject's skin data is reviewed by machine learning software, comparing the data to:
  (i) prior skin data of the Subject, and/or
  (ii) skin data of other users contextually similar to the Subject, and/or
  (iii) skin data of "healthy skin", and after analysis, a report is sent to (x) the Subject, or (y) the Subject's preselected Professional, or (z) both.
3. The Subject's skin data is reviewed by deep learning software, and after analysis, a report is sent to (x) the Subject, or (y) the Subject's pre-selected Professional, or (z) both.

XV. SKIN MONITORING SERVICE: SOFTWARE ARCHITECTURE

Figure 4:
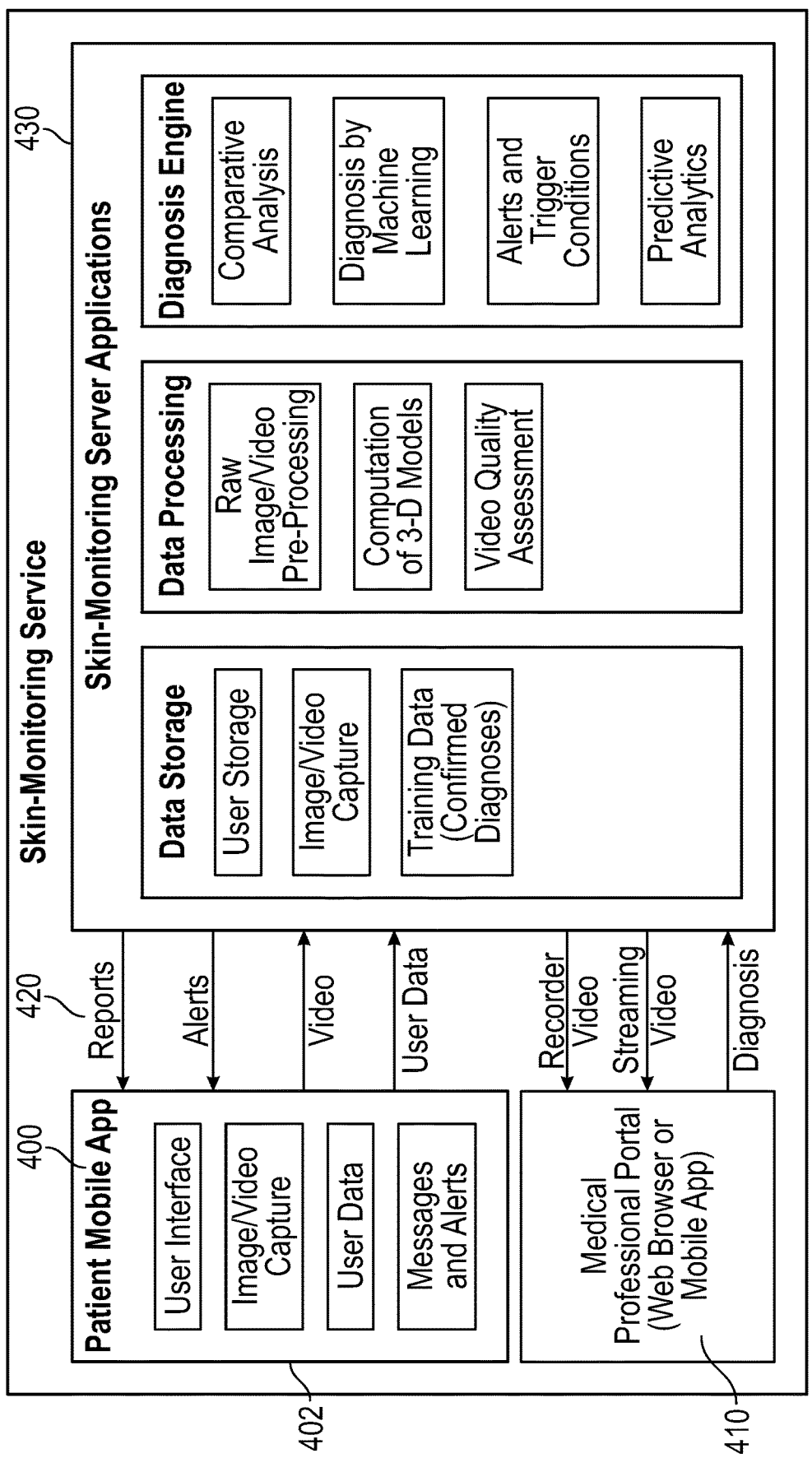
FIG. 4 shows a block diagram of a skin monitoring service.

The software components included in one embodiment of the skin monitoring service are depicted in FIG. 4.

First, this embodiment of the invention includes a Subject/Patient Mobile App 400 that runs on a user's handheld computing device 402 such as a smartphone or small tablet. The Subject/Patient Mobile App may be acquired from an online app marketplace, such as the Apple App Store or Google Play. The Subject/Patient Mobile App includes several subcomponents. A user interface subcomponent implements the menus, graphics, buttons, and data displays with which a user interacts when the Subject/Patient Mobile App is active. An image/video capture subcomponent implements logic for initializing the device camera, configuring the camera's settings to increase captured image quality, capturing raw images, and storing images to the flash memory of the mobile device. A user data component is responsible for storing information about the current Subject/patient user, such as the unique identifiers that associate the user with medical records and provider information that are stored securely within the server-side applications and databases of the skin-monitoring service.

Using the Subject/Patient Mobile App, a Subject/patient can enroll or register in the skin-monitoring service. Optionally, the skin-monitoring service may be configured to restrict enrollment to Subject/patients who have been invited by a medical provider. A user who has successfully enrolled in the service is able to log in to the Subject/Patient Mobile App using standard means, such as a password, fingerprint, or facial or iris recognition. Once logged in, a Subject/patient can view a variety of data that has been collected, stored, or generated by the skin-monitoring service. For example, a Subject/patient can view images and videos that have been collected using the Subject/Patient Mobile App. Similarly, a Subject/patient can view past and current alerts and notifications generated by the skin-monitoring service. A Subject/patient can also review messages sent to or received from the Subject/patient's medical provider. A Subject/patient can also initiate new correspondence with his or her medical provider. Depending on the configuration of the skin-monitoring service, a Subject/patient may also be able to initiate the capture of a new skin image or video. Also depending on the configuration of the skin-monitoring service, a Subject/patient may be able to view health metrics and evaluations generated by the skin-monitoring service.

Second, this embodiment of the invention includes a Medical Professional Portal 410 that may be accessed through a web browser or mobile app. For example, a medical professional may opt to access the Medical Professional Portal through a web browser when in an office setting that includes desktop and laptop computers, and the medical professional may opt to access the Medical Professional Portal through a mobile app at other times and locations.

Using the Medical Professional Portal, a medical professional may, for example, view a list of patients whose medical information the medical professional is authorized to view. The medical professional may view records associated with these patients, such as the patient's demographic and medical information as well as images and videos the patients' skin that have been captured by the skin-monitoring system. The medical professional may also view current and past alerts that have been generated by the skin-monitoring system. The medical professional may also view the results of automated analyses and assessments performed by the skin-monitoring system. For example, the medical professional may view in a table, graph, or other format the changes that have occurred to the patient's skin over a period of time. The medical professional may similarly view risk metrics and scores produced by the skin-monitoring system.

Both the Subject/Patient Mobile App and the Medical Professional Portal are connected via an Internet connection 420 to a collection of Skin-Monitoring Server Applications 430 that run on server computers. The Subject/Patient Mobile App and Medical Professional Portal exchange a variety of information with the Skin-Monitoring Server Applications using an encrypted, secure data transmission protocol, such as HTTPS. For example, when a new Subject/patient user registers for the service or changes information in his or her profile, including medical information, the Subject/Patient Mobile App uploads the patient information to the Skin-Monitoring Server Applications where it is added or updated within a secure data storage system. As another example, when a new image or video has been captured by the Subject/Patient Mobile App, the Subject/Patient Mobile App uploads the image(s) and video(s) to the Skin-Monitoring Server Applications. Similarly, when a medical professional selects to view a Subject/patient's information or skin images or videos using the Medical Professional Portal, the information is securely downloaded from the Skin-Monitoring Server Applications to the Medical Professional Portal.

The Skin-Monitoring Server Applications include applications and programs for processing and analyzing skin images and videos in a variety of ways. One server application performs pre-processing of raw images and videos received from the Subject/Patient Mobile App. This application reads metadata associated within the image or video, including the video format, resolution, creation time, patient name and ID, and so on, and inserts a record containing this information in a database.

Another server application processes the images and videos to assess their quality. This application analyzes the videos to determine the position of the skin within the image or video and evaluates whether the lighting, color, clarity, and stability in the image or video are acceptable. This server application may also include the capability to improve the image or video in various ways. For example, this server application may crop out portions of the image or video that do not contain the targeted area of skin or are not otherwise useful. The server application may attempt to adjust image characteristics such as white balance. The server application may run a stabilization algorithm on a video to reduce shakiness and keep the position of the targeted area of the skin in the video constant. When an image or video is received that does not pass the quality assessment, and the quality cannot be improved through the mechanisms described, the server application may generate an alert or notification that is transmitted to the Subject/Patient Mobile App advising the Subject/patient that the image or video was unusable and a new image or video should be captured.

Another server application implements algorithms for generating models and measurements of the Subject/patient's skin and targeted portions thereof (i.e., Skin data). This server application may compute measurements of, for example but without limitation, the size, shape, color, temperature, and texture of, for example, a skin burn, puncture wound, mole, lesion or "growth", and/or rashes, et al.

Another server application implements algorithms for generating models and measurements of the Subject/patient's skin and targeted portions thereof (i.e., Skin data). This server application may compute measurements of the size, shape, depth, and texture of a skin burn, puncture wound, lesion or "growth", and/or rash area, et al. This server application may also characterize the color of the area of skin (e.g., redness or yellowness); the presence and position of blood vessels; or the presence of other anomalous structures. This server application may be configured to compute specific models and measurements for particular users and may be calibrated based on past images, videos, models, and measurements stored within the skin-monitoring service's databases.

Other server applications are responsible for performing diagnostic analyses. These diagnostic applications are configured to assess the risk or probability that a Subject/patient has a particular medical condition or the severity of a known medical condition has changed. One diagnostic application may be programmed to perform comparative analyses, in which images, videos, models, or measurements of a Subject/patient's targeted areas of skin are compared with past images, videos, models, or measurements of the same patient, a known healthy patient, or a known diseased patient. Such an application may, for example, determine whether the Subject/patient's targeted area of skin has changed in shape or color or whether new anomalous structures have appeared.

While this patent application as described herein describes carrying out certain diagnoses, it should be understood that this encompasses not only carrying out the diagnosis, but also providing an indication of the data from which a diagnosis could be carried out either by another computer, or by a professional. It is envisioned that certain aspects of this invention could hence be embodied without receiving FDA approval for the diagnosis.

Another diagnostic application may be programmed to use machine learning techniques to quantify the risk that a Subject/patient has a particular condition based on an image or video of the Subject/patient's targeted area of skin. The machine-learning-based diagnostic application may be constructed using supervised learning techniques, in which a machine learning algorithm is supplied with training data to classify inputs. In the skin-monitoring service, a diagnostic application that uses supervised machine learning may use the images and videos collected by the Subject/Patient Mobile App, skin models and measurements computed from those images and videos, and medical and demographic information provided by the Subject/patient or medical provider to classify Subject/patients as high risk or low risk for a particular condition. The diagnostic application may also provide a probability distribution describing the risk of a particular Subject/patient for a particular condition. The training data needed by the supervised machine learning algorithm may be provided in the form of a dataset that has been collected external to the skin-monitoring service, but in the preferred embodiment the skin-monitoring service is able to use its own collected data as training data. For example, if the skin-monitoring service collects images of a Subject/patient's targeted areas of skin and subsequently the Subject/patient is diagnosed in a medical professional's office with a particular skin condition, this finding can be fed back into the skin-monitoring service as a data point for training the supervised machine learning algorithm.

The machine-learning-based diagnostic application may also be constructed using unsupervised machine learning techniques, which are helpful for finding undiscovered patterns in data. Unsupervised learning may be used to cluster patients into similar groups based on skin images, videos, models, measurements, demographic data, and medical history. This analysis may then indicate previously unknown patterns in the data or identify outliers that, along with the subject matter expertise of medical professionals, could be used to improve diagnoses of skin conditions or other conditions that affect the skin. For example, if the cluster analysis produces a cluster of patients among which the incidence of a condition is higher than normal, it may indicate that some characteristic of that group is associated with elevated risk for the condition.

The skin-monitoring service is designed as an extensible platform such that new data processing and diagnostic applications may be "plugged-in" over time. If medical researchers develop a new diagnostic engine for a particular disease based on image processing and machine learning techniques, that engine can be plugged-in to the skin monitoring service through the use of standard interfaces and software adapters. For example, the skin-monitoring service may optionally be implemented using web services and protocols that allow for individual components and application to be inserted and removed from the system over time.

These additions may include:
(x) non-skin "health data" of the Subject which, through means and techniques known to those skilled in the art the invention can input and cross-compare and cross-reference with
(y) the skin data of the Subject (as obtained and processed by the invention), to potentially reach a more dispositive probability of the indication of a Subject's skin condition and/or trend and speed of the trend of a Subject's skin condition (thereby potentially better facilitating for the Subject both acute and long-term therapy adjustments).

For example, non-skin "health data" of the Subject may include (without limitation) those items set forth on Schedule N attached hereto.

Adding an alternate type of Subject "health data" to a Subject's skin data (as described by the invention), can potentially assist in measuring if a Subject's potential skin condition indication is either more or less valid as well as its apparent trend and the speed of that trend (thereby potentially better facilitating both acute and long-term therapy adjustments).

Over time, comparing and cross-referencing alternative types of Subject "health data" together with the Subject's skin data (as described by the invention) can potentially result in a virtuous cycle which potentially strengthens and cross-validates the potential Subject skin condition indications identified by each type of data.

While any type of Subject "health data" can potentially come first in identifying a potential Subject skin condition indication, which if potentially identified may be followed by the addition of one or more other types of "health data" for greater or lesser potential cross-validation, it is the inventor's view that the invention, given its ability in certain modes of use to work in an automatic mode or semi-automatic mode requiring little if any effort by the Subject, may for many Subject skin conditions be the first line of potential indication of potentially severe skin condition or a non-skin Subject health condition, identifying potentially severe skin conditions or non-skin Subject health conditions that might never be addressed or otherwise might be addressed at a much later, at a time in which it is more costly and difficult to address the condition, if at that point the condition can be meaningfully addressed at all.

XVI. SKIN EXAM/SKIN MONITORING OUTPUT (FOR HEALTHCARE PROFESSIONAL OR COMPUTER VISION)

Examples of alternative potential invention data outputs include, without limitation:

A. Computer Screen and Projectors.

1. Computer Screens/Monitors.

The output computer screens/monitors used by the invention for Professionals are the same as or similar to commercially available high-resolution, high refresh-rate, high response time, high color gamut, and high contrast computer and television video screens/monitors today, and those that have been developed but have not yet been released into the commercial marketplace.

For example, without limitation mini LED panels and OLED, each which produce their own light source and are more stable, are but two technologies improving video display performance.

The invention provides the user with touch screen capability, including the potential ability to touch the screen and increase-or-decrease the size of the image on the screen, or to do so through software and a mouse/trackpad/finger or similar control input device, change the resolution of the screen and/or visually increase-or-decrease the size of the image on the screen, etc.

The output computer screens/monitor ideally (but not necessarily) will be 3D capable.

The output computer screen/monitor or computer to which it is connected will have a "speaker/headphone/earphone" and microphone so the user can hear audio data from the computer (e.g., the computer's AI-powered chatbot, the Subject's voice, et al.) and speak commands to the computer and/or make comments to the Subject [similar to speaking to Amazon's Alexa]).

2. Projectors.

Output computer projectors used by the invention will have high resolution, probably (but not necessarily) show 3D images, have excellent color accuracy, have appropriate brightness, and other appropriate qualities known to those skilled in the art.

The computer to which the projector is connected will have a "speaker/headphone/earphone" and microphone so the user can hear audio data from the computer (e.g., the computer's AI-powered chatbot, the Subject's voice, et al.) and so the Professional can speak commands to the computer and/or make comments to the Subject [similar to speaking to Amazon's Alexa]).

B. AR/VR Output Glasses and/or Goggles and/or Headsets.

1. AR Output Glasses.

The AR output glasses (the "AR Output Glasses") are an output device in which information is displayed in both lenses. The AR Output Glasses will function as mobile (but wirelessly connected to a smartphone or its equivalent or a PC or larger computer), tethered (connected by wire to a PC or larger computer), or standalone (functioning and communicating totally on its own).

In addition, the AR Output Glasses will have a "speaker/headphone/earphone and microphone (which may-or-may not use the functionality of the smartphone or its equivalent [as a headphone wirelessly or by wire connected to a smartphone does today], depending on the type of AR Output Glasses being used), so the wearer can hear audio data from the computer (its AI-powered chatbot, the Subject's voice, et al.) and can speak commands to the computer and/or make comments to the Subject [similar to speaking to Amazon's Alexa]).

The output AR Output Glasses will allow authorized Professionals to, by manual control, verbal input to, online selections, or otherwise, for example but without limitation:
(i) focus in-or-out or increase-or-decrease the magnification of the image or video being displayed, as well as increase-or-decrease the speed of the video being displayed (i.e., time lapse imagery).
(ii) project a "split screen" display, to, without limitation:
(x) compare a Subject's targeted area of skin or specified skin data at an earlier date to the same Subject's skin or specified skin data at a later date, or
(y) compare a Subject's targeted area of skin or specified skin data at a certain date to a "healthy skin" or "healthy specified skin data", with appropriate adjustments made for age, et al.

2. AR Output Goggles.

The AR output goggles ("AR Output Goggles") are an output device in which information is displayed in both lenses. The AR Output Goggles will function as mobile (but wirelessly connected to a smartphone or its equivalent or a PC or larger computer), tethered (connected by wire to a PC or larger computer), or standalone (functioning and communicating totally on its own).

Note: In some mobile AR Output Goggles there is a slot into which the user places his or her smartphone or its equivalent.

In addition, the AR Output Goggles will have a "speaker/headphone/earphone" and microphone (which may-or-may not use the functionality of the smartphone or its equivalent [as a headphone wirelessly or by wire connected to a smartphone does today], depending on the type of AR Output Goggles are being used), so the wearer can hear audio data from the computer (its AI-powered chatbot, the Subject, et al.) and speak commands to the computer or the Subject (similar to speaking to Amazon's Alexa).

The AR Output Goggles will allow authorized Professionals to, by manual control, verbal input to, online selections, or otherwise, for example but without limitation:
a. focus in-or-out or increase-or-decrease the magnification of the image or video being displayed, as well as increase-or-decrease the speed of the video being displayed (i.e., time lapse imagery).
b. project a "split screen" display, to,
(i) compare a Subject's targeted area of skin or specified skin data at an earlier date to the same Subject's targeted area of skin or specified skin data at a later date, or
(ii) compare a Subject's targeted area of skin or specified skin data at a certain date to a "healthy targeted area of skin" or "healthy specified skin data", with appropriate adjustments made for age, et al.

3. VR Headsets, VR Goggles, and VR Glasses.

The terms "VR headsets", "VR goggles", and "VR glasses", are used interchangeably with no difference between them and hereafter will be collective known as "VR Output Headsets".

The VR Output Headsets are similar to virtual reality headsets known to those skilled in the art, but are a part of the overall instant invention with a specific usage as described herein.

The VR Output Headset will function as:
a. mobile (but wirelessly connected to a smartphone or its equivalent or a PC or larger computer),
b. tethered (connected by wire to a PC or larger computer), and/or
c. standalone (functioning and communicating totally on its own).

Note: In some mobile VR Output Headsets there is a slot into which the user places his or her smartphone or its equivalent.

The output VR Output Headsets will have a "speaker/headphone/earphone" and microphone (which may-or-may not use the functionality of the smartphone or its equivalent [as a headphone wirelessly or by wire connected to a smartphone does today], depending on the type of VR Output Headset is being used), so the wearer can hear audio data from the computer [its AI-powered chatbot, the Subject's voice, et al.] and speak commands to the computer or provide comments to the Subject [similar to speaking to Amazon's Alexa]).

The VR Output Headset will allow authorized Professionals to, by manual control, verbal input to, online selections, or otherwise, for example but without limitation:
a. focus in-or-out or increase-or-decrease the magnification of the image or video being displayed, as well as increase-or-decrease the speed of the video being displayed (i.e., time lapse imagery).
b. project a "split screen" display, to, without limitation:
(i) compare a Subject's targeted area of skin or specified skin data at an earlier date to the same Subject's targeted area of skin or specified skin data at a later date, or
(ii) compare a Subject's targeted area of skin or specified skin data at a certain date to a "healthy targeted area of skin" or "healthy specified skin data", with appropriate adjustments made for age, et al.

Controls to allow for focusing in or magnifying of the image or video being displayed. Controls to allow for the slowing of speed of video being displayed.

C. AR Contact Lenses.

AR contact lenses ("AR Invention Output Contact Lenses") solely for reviewing the invention output may be a type of invention output used by Professionals and/or others.

AR Invention Output Contact Lenses would be custom-made to fit the wearer, would be wireless, and can be connected to a computer/smartphone and/or similar device with a WiFi relay, with a data exchange transmission protocol embedded inside each of the contact lenses with a data exchange rate in a 4G or 5G [or future] format. They would be powered, without limitation, by a micro-battery (e.g., without limitation, a stretchable self-healing Li-ion micro-battery, or a thin-film solid-state battery) within each contact lens.

Micro-components (including for example, without limitation, an ARM-based processor, a communications chip, and an imaging sensors will provide complex computing functions) and micro-displays are integrated directly into each autonomous contact lens. The lenses will be compliant with ocular safety norms, such as EN62471-2008 and its progeny.

The lens will rely on an internet connection provided by a smartphone or its equivalent or some other device for sending and receiving data.

Information with respect to AR contact lenses such as the AR Invention Output Contact Lenses is known to those skilled in the art.

The AR Invention Output Contact Lenses can work together with a speaker/headphone/earphone/earplug" and microphone (which may-or-may not use the functionality of the smartphone or its equivalent [as a headphone wirelessly or by wire connected to a smartphone does today], so the wearer can hear audio data from the computer [its AI-powered chatbot, the Subject's voice, et al.] and speak commands to the computer or provide comments to the Subject [similar to speaking to Amazon's Alexa]).

D. AR Projectors.

AR projectors solely for reviewing invention output ("AR Invention Output Projectors") can be a type of invention output used by Professionals and/or others.

AR projectors such as the LF2 are already being sold in the commercial marketplace.

Yinscorp Ltd. has its Count Projector, which transforms a smartphone into an interactive augmented reality projector.

Information with respect to AR projectors is known to those skilled in the art.

The AR Invention Output Projector can work together with a "speaker/headphone/earphone/earplug" and microphone (which may-or-may not use the functionality of the smartphone or its equivalent [as a headphone wirelessly or by wire connected to a smartphone does today], so the wearer can hear audio data from the computer [its AI-powered chatbot, the Subject's voice, et al.] and speak commands to the computer or provide comments to the Subject [similar to speaking to Amazon's Alexa]).

E. AR Projections from, without Limitation, a Smartphone, Smart Pad, or their Equivalents.

AR projections from, without limitation, a smartphone, smart pad, or their equivalents ("Invention AR Projections on a Smartphone et al.") can be a type of invention output used by Professionals and/or others.

Yinscorp Ltd. has its Count Projector, which transforms a smartphone into an interactive augmented reality projector.

Smartphones themselves or their equivalents can generate AI projections, although commercial versions have yet to be released.

Information with respect to AR projections from, without limitation, a smartphone, smart pad, or their equivalents, is known to those skilled in the art.

F. 3D Printer Output.

A 3D printer is a computer-aided manufacturing (CAM) device that creates three-dimensional objects. Like a traditional printer, a 3D printer receives digital data from a computer as input. However, instead of printing the output on paper, a 3D printer builds a three-dimensional model out of a custom material.

3D printer output ("Invention 3D Printer Output") can be a type of invention output used by Professionals and/or others. 3D printer output may assist in the visualization in a material 3D format of a potential Subject's skin condition.

Note: The output, in whatever custom material, could be in real color, assigned colors, or black and white/grayscale.

Information with respect to this type of output is known to those skilled in the art. It should be noted that a Professional or others may view invention output through any combination or permutation of the above-mentioned invention output devices.

XVIII. SKIN EXAM/SKIN MONITORING OUTPUT (FOR SUBJECT WHOSE TARGETED AREAS OF SKIN ARE BEING EXAMINED OR MONITORED [OR IF THE SUBJECT IS AN ANIMAL ITS OWNER])

Some of the invention output intended for Professionals may be useful for a Subject to directly see or hear to better understand a potential Condition they may have, and to motivate them in certain circumstances to act to alleviate the potential Condition.

For example, it may be useful for a Subject to be able to directly see certain Professional-selected invention output for certain potential Conditions:

A. Computer Screen/Monitor.

If the Subject owns an appropriate computer screen or monitor (or can borrow or lease one), the invention output can be digitally transmitted to the Subject for review and discussion with the Subject (by AI-powered chatbot, a Professional, or otherwise).

B. Projector.

If the Subject owns an appropriate projector (or can borrow or lease one), the invention output can be digitally transmitted to the Subject for review and discussion with the Subject (by AI-powered chatbot, a Professional, or otherwise).

C. AR Output Glasses or AR Output Goggles.

If the Subject owns appropriate AR Output Glasses or AR Output Goggles (or can borrow or lease one), the invention output can be digitally transmitted to the Subject for review and discussion with the Subject (by AI-powered chatbot, a Professional, or otherwise).

D. VR Output Headset.

If the Subject owns an appropriate VR Output Headset (or can borrow or lease one), the invention output can be digitally transmitted to the Subject for review and discussion with the Subject (by AI-powered chatbot, a Professional, or otherwise).

E. AR Invention Output Contact Lenses.

If AR Invention Output Contact Lenses become commonplace and the Subject already owns a pair of such AR lenses or their equivalent (given that such lenses are custom-made), the invention output can be digitally transmitted to the Subject for review and discussion with the Subject (by AI-powered chatbot, a Professional, or otherwise).

F. AR Invention Output Projector.

If AR Invention Output Projectors become commonplace and the Subject owns one or its equivalent (or can borrow or lease one), the invention output can be digitally transmitted to the Subject for review and discussion with the Subject (by AI-powered chatbot, a Professional, or otherwise).

G. Invention AR Projections on a Smartphone et al.

The Subject will most likely own (or can borrow or lease) one of these invention output devices (i.e., a smartphone or smart pad with this AR capability), and the invention output can be digitally transmitted to the Subject for review and discussion with the Subject, by AI-powered chatbot, a Professional, or otherwise).

H. Invention 3D Printer Output (which invention output can be physically delivered to a Subject for review and discussion with the Subject, by AI-powered chatbot, a Professional, or otherwise).

XIX. SOFTWARE—BOTH "IF-THEN" AND "PREDICTIVE"

Every task has a group of decisions at its heart, and those decisions have some predictive element.

A. "If-Then" Software.

Use of software with basic "if-then" rule-based logical intelligence.

For some decisions, you can articulate the requisite judgment and express it as computer code. We often, for example, explain our thinking to other people. Codifiable judgment allows you to fill in the part after "then" in the "if-then" statements. When this happens judgments can be enshrined and programmed.

In some cases, the number of possible predictions may make it too costly for any human to judge all the possible payoffs in advance. Instead, a human needs to wait for the prediction to arrive and then assess the payoff, which is close to how most decision-making currently works, whether or not it includes machine-generated predictions.

The downside of "if-then" software is sometimes there are too many "ifs" to possibly code. Neither traditional statistical methods nor algorithms of if-then statements tend to operate well in complex environments.

For example, autonomous vehicles, which have existed in controlled environments for over two decades (generally limited to places with detailed floor plans, such as warehouses and factories), could not function outside highly predictable, controlled environments until engineers reframed navigation as a predictive problem. Instead of telling the machine what to do in each circumstance, engineers focused on a single predictive problem: What would a human do?

B. "Predictive" Software.

Artificial intelligence (AI) is predictive technology. Predictions are inputs to decision-making. AI arguably improves prediction and drops its cost. It can work together with and as part of the workings of digital cameras, machine/computer vision, video and/or audio (known as "natural language processing"), and, of course, much more.

One type of AI, known as "deep learning", relies on an approach called "back-propagation". It "learns" through example.

Machines and humans have strengths and weaknesses in the context of prediction. Prediction machines are better than humans at factoring complex situations among different indicators, especially in situations with rich data. Humans, however, have cognitive models of how the world works (causality versus correlation), and typically do better than predictive machines in settings with "thin data" and "human prediction by exception".

The unit cost per prediction falls as the frequency increases. Human prediction does not scale the same way.

Prediction machines are valuable in part because prediction is a key ingredient in decision-making under uncertainty. Prediction machines can reduce uncertainty, but will not always eliminate it. AI can increase confidence, and in the case of the invention indicate to the person whose eyes are being examined that an issue has been indicated, and that they may want to inform a medical professional of the indication and have the medical professional decide what to do or not do. The appropriate medical professional can decide what is driving the conclusion and make the ultimate diagnosis.

Note: A prediction is not a decision, but only a component of a decision. The other components are judgment, action, and outcome, compared to three types of data, those being input, training, and feedback.

For the invention, AI can provide the probabilities, but for now human experts will translate the AI output and actual diagnostic and decide treatment.

1. Supervised Learning.

Supervised learning is a technique used when you have a good idea of what you want to predict.

2. Reinforcement Learning.

Reinforcement learning, in contrast to supervised learning, is a technique used when you do not have good data, but you can tell, after the fact, how right you were.

While training the prediction machine most likely happens in the cloud, once the machine is trained it may be possible to do predictions directly in the device without sending the data back to the cloud.

In addition, while this application describes in various locations carrying out and storing certain operations in the "cloud" it should be understood that any form of distributed computing or storage could be used, including but not limited to EDGE AI and EDGE computing.

3. Convolutional Neural Networks.

Convolutional neural networks have proven very efficient at computer vision tasks, but generally need huge amounts of annotated data. Supervised pre-training has been helpful. In this approach, a convolutional neural network is initially trained on a database of images such as ImageNet. Supervised pre-training has been found to be helpful in applications such as medical imaging.

4. Self-Supervised Learning.

Self-supervised learning trains deep learning models for medical imaging. It reduces the need for annotated data. Self-supervised learning trains data without the need for labels, where label data is scarce and unlabeled data is abundant. Unlabeled data is often available in large quantities in various medical domains. Multiple views of the underlying pathology commonly present in medical image datasets are utilized to construct image pairs for contrastive self-supervised learning.

5. Pathways.

Pathways is a new AI architecture aimed at improving the current machine learning problem of being too focused on a particular goal. It can manage multiple tasks at once and learn new functions rapidly. Pathways enables AI to overcome many existing systems' flaws while also combining their strengths, including multimodal models which include vision, audio, and language understanding. It is the inventor's view that Pathways AI architecture as part of the invention software will prove extremely useful for detecting patterns in data gathered from the Subject's targeted areas of skin and greatly enhance the predictive ability of the invention for the Subject's health conditions, while also assisting with the audio input and output portions of the invention. An embodiment defines using Pathways techniques and their progeny as part of the skin monitoring and analysis and as part of the invention.

6. Geometric Deep Learning.

Geometric deep learning is an emerging subfield of AI that can learn patterns on curved surfaces. The surface of skin is curved. It can be used for, among other things, to detect potential interactions among proteins—the complex folded molecules responsible for many biological processes—40,000 times faster than conventional methods. It allows researchers to scan a protein's 2D surface for what researchers call interaction fingerprints: features learned by a neural network that indicate another protein could bind there, allowing for predicting protein interactions. It is the inventor's view that geometric deep learning as part of the invention software will prove extremely useful for detecting patterns in data gathered from the Subject's areas of skin and greatly enhance the predictive ability of the invention for Subject Conditions. An embodiment defines using Geometric deep learning techniques and their progeny as part of the skin monitoring and analysis and as part of the invention.

7. Gauge CNN Algorithms.

It is the inventor's view that Gauge CNN algorithms and their progeny will prove extremely useful for detecting patterns in data gathered from the irregularly curved surfaces of Subject's targeted areas of skin as well as the skin over the totality of the Subject's body. It is also the inventor's view that Gauge CNN and its progeny will be much more efficient in the use of training data.

Please note that Qualcomm is now working on improved computer vision applications based on Gauge CNNs.

An embodiment defines using Gauge CNN techniques and their progeny as part of the skin monitoring and analysis and as part of the invention. [https://www.quantamagazine.org/an-idea-from-physics-helps-ai-see-in-higher-dimensions-20200109/]]

C. Local Device Software Upgrades/Over-the-Air Software Upgrades.

In an effort to improve its autonomous driving software, Tesla collects driving data from each of its cars as they are driven by their owners, and uses artificial intelligence software and other means to process the data in a manner to potentially improve the company's autonomous driving software. Periodically, Tesla sends over-the-air software updates to cars it sold to their owners so the cars are able to perform better based on the data that Tesla collected and processed, to make its self-driving software (and other types of software in Tesla vehicles) perform better.

In a similar manner, in the cloud (or locally for Edge AI and edge computing), the skin data of consenting Subjects will be processed using AI software and other means to process the data in a manner to potentially:
1. Improve the invention's Rules-based programs/"if-then" and/or predictive and other software capabilities, and
2. Discover new correlations with respect to the skin of Subject/users of the invention as they relate to potential diseases and Conditions of a Subject's eyes, body and/or brain (and vice versa).

Somewhat similar to the manner in which certain deep learning programs use back-propagation to improve the efficacy of the predictiveness of the program, the invention may ask follow-up questions of the user to refine the Rules-based programs/"if-then" and/or predictive aspect of what the invention is measuring. One embodiment of the invention relies on the use of synthetic data.

Synthetic data is data that is artificially manufactured and not actually created by real-world activities and events. It is important because developing AI and ML (machine learning) projects require immense amounts of data, and real-world data can be expensive and difficult to collect.

A lot of real-world data collection is done manually, which can be very, very slow. It can also be prone to incorrect labeling or other human error since it is manually gathered.

Synthetic data eliminates many of those issues. It is easier and faster to collect, and allows developers to more quickly produce the algorithms and AI models they need.

For an AI solution to work, it requires three components:
1. Training data;
2. Neural network machine learning algorithms; and
3. An integration platform.

A. Training Data.

As mentioned, creating large enough data sets to effectively train algorithms is a resource-intensive endeavor. Computer vision models only work after they have ingested extensive data of various "objects", which data is not always available. While the sheer quantity of training data needed is a challenge, of even greater importance is ensuring sufficient variation within the training data to represent real-world conditions. Through use of computer-generated imagery that closely matches real world imagery, training datasets with robust variations are rapidly generated, providing a scalable method of generating training data without having to devote extensive resources to manually harvesting, labeling, and curating training data from real imagery.

B. The Trained Algorithm on the Platform.

Once trained with appropriate training data, the trained algorithm can then operate on the platform to automatically analyze real collected imagery and make appropriate evaluations. Synthetic data is a disruptive technology that holds the key to breaking through the training bottleneck for AI/ML solutions. It has been used by Microsoft, Google, and Amazon, the latter of which used it in Alexa. In October 2021 Facebook acquired New York-based synthetic-data generator A.I.Reverie, and the next month Nvidia said it was creating an engine for generating synthetic data for training AI networks.

Synthetic data is an alternative solution and arguably represents the future of training AI algorithms for rare "objects", for times when there are not enough varied real-world images for training. For example, a defense contractor could create synthetic imagery of a fighter jet against different backgrounds, in various weather conditions, and at distinct viewing and sun angles.

Another driving force behind synthetic data's surging growth is privacy. Although companies may be drowning in data, they cannot always use real-world datasets due to legal, ethical, or business limitations. Synthetic data avoids that issue.

For example, Deep Learning models can take over the classifications of diseases based on medical scans, and in doing so release medical staff from this duty, giving them the necessary time to focus on patients.

Synthetic datasets keep the properties of the original data. Nevertheless, a backtracking to the original data is extremely improbable because synthetic data are built up of "noise" in a probabilistic way without ever seeing the original data.

See https://christianschitton.medium.com/synthetic-image-generation-mona-lisas-sister-909008907660

In a synthetic data world, the quality of the initial, small dataset from which the synthetic data is derived is absolutely paramount, as it is a deeply contextualized understanding of the data itself: where it came from, what it can be used for, what it explains, and what it does not explain.

Raw, real-world data often contains innumerable confounding variables. Understanding the limitations of digital data, real or synthetic, in informing decision-making is important.

Figure 5:
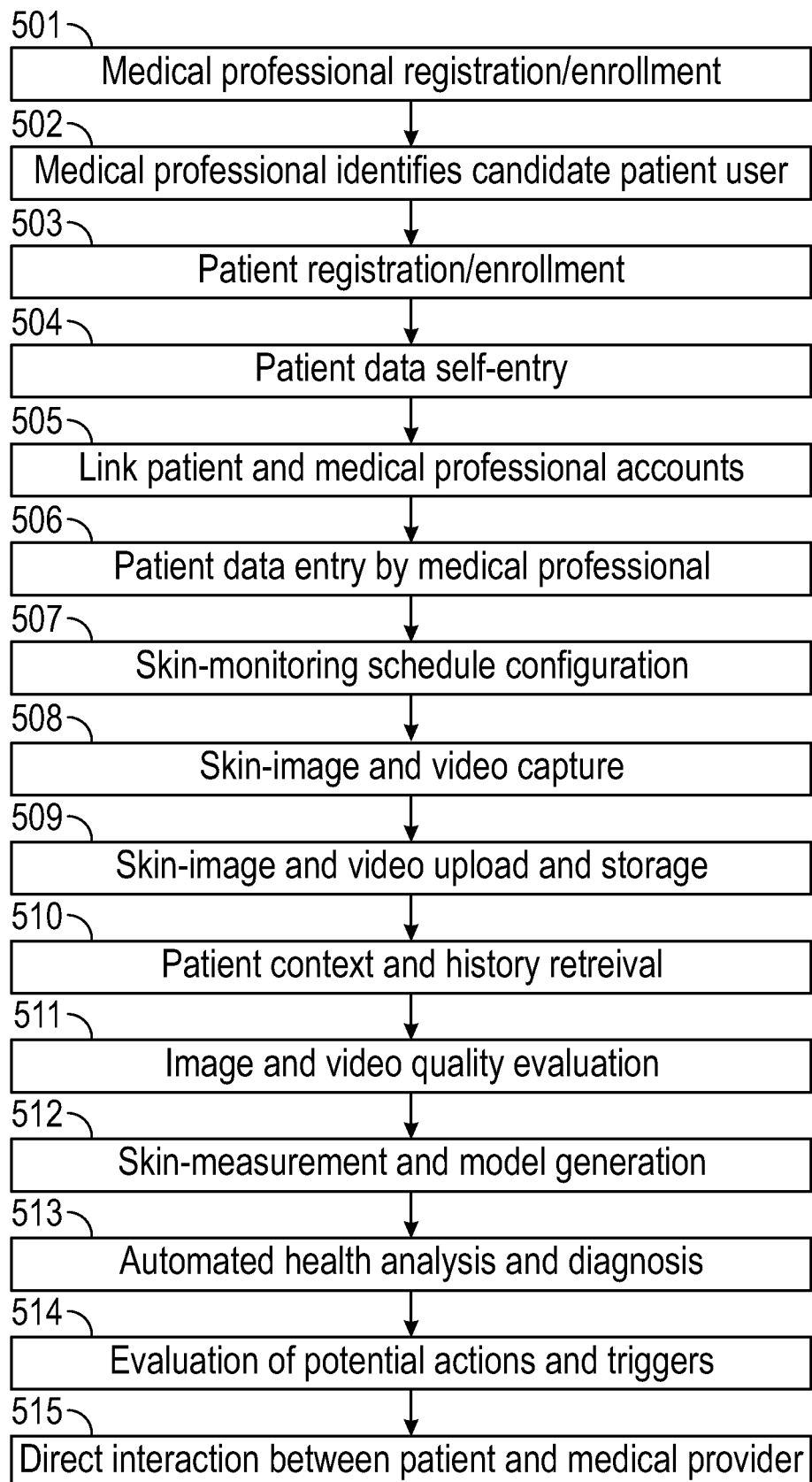
FIG. 5 shows a flowchart of operation.

The processors that are disclosed herein can execute instructions, e.g. run a flowchart, an embodiment of which is shown in FIG. 5.
  a. At 501, a Professional signs up to use the invention's app-based skin-monitoring service to monitor Subject/patients. The Professional receives training regarding the correct use of the service and is provided with user credentials to access the skin-monitoring service through a web browser or mobile app.
  b. At 502, the Professional informs a Subject/patient that the Subject/patient has an elevated risk for a disease or Condition. The disease or Condition may be at least partially diagnosed through visual inspection of the skin or may include symptoms that appear in the skin, as explained fully elsewhere in this document. [For example, the Subject/patient may be at high risk for jaundice, which may cause yellowish or greenish pigmentation of the whites of the Subject/patient's eyes.] The Professional advises the Subject/patient that the Subject/patient is eligible to enroll in an app-based skin-monitoring service which may facilitate detection of the disease or Condition.

c. At 503, the Subject/patient elects to enroll in the app-based skin-monitoring service. The Subject/patient downloads and installs the mobile app from an online app marketplace, such as the Apple App Store or Google Play. The Subject/patient is prompted to hear and/or read and accept the necessary terms and conditions to use the service. The Subject/patient may be provided the option to view a video, audio, or text tutorial explaining how the service works, what information the service gathers, and how that information will be used.

d. At 504 the Subject/patient enters various information about himself or herself and his or her medical history. For example, the Subject/patient may preferably enter information including but not limited to her name, gender, age, height, weight, and medical provider. The Subject patient may also enter, or arrange for others to enter, Additional Information and/or Other Information.

e. At 505, a notification is sent to the Subject/patient's Professional advising the Professional that the Subject/patient has enrolled in the skin-monitoring service. The notification may be provided, without limitation, by phone, text message, email, or push notification. The Professional confirms that the Subject/patient is, in fact, a current Subject/patient of the Professional and is a candidate for the skin-monitoring service. The Subject/patient's user account and the Professional's user account become "linked" such that the Professional will receive further notifications regarding the Subject/patient's health, when appropriate, and view and edit the Subject/patient's medical data stored within the service.

f. At 506, the Professional inputs information regarding the Subject/patient's medical history and the disease or condition for which the patient may have an elevated risk. For example, the Professional may indicate that the Subject/patient has an elevated risk for jaundice.

g. In step 507, the skin-monitoring service is configured with a skin-monitoring schedule. The skin-monitoring schedule may be determined by the service itself (automatically in a "customized" manner by the service software or by a standard default) based on the information provided by the Subject/patient and the Professional, including but not limited to the nature of the Condition being monitored and the preferences of the patient and Professional.

Alternatively, the monitoring schedule may be set by the Subject/patient or Professional. Alternatively, the eye-monitoring service may be configured to opportunistically monitor the Subject/patient's skin when, for example but without limitation, the Subject/patient is using his or her smartphone for other purposes.

h. In step 508, the skin-monitoring service captures images and video of the Subject/patient's skin, or targeted areas thereof. If a skin-monitoring schedule has been set, the skin-monitoring service preferably notifies the Subject/patient when it is time to perform a skin image or video capture. The notification may be provided, without limitation, by smartphone, text message, email, or push notification. The Subject/patient then activates the mobile app of the skin-monitoring service and is prompted to capture images and videos of his or her skin, or targeted areas thereof. Alternatively, if the skin-monitoring service has been configured to opportunistically monitor the Subject/patient's skin, or targeted areas thereof, images and video of the Subject/patient's skin, or targeted areas thereof are captured while the Subject/patient is, for example but without limitation, using his or her smartphone for other purposes.

i. In step 509, the captured images and video are uploaded to a server computer running the server-side application (or "back-end") of the skin-monitoring service. The images and video are tagged with the user's identity, the date and time the images and/or video were captured, and other metadata as appropriate. The images and video are encrypted during transmission and storage to ensure the privacy of the Subject/patient's data. The images or video are stored in a database within the server that is designed for efficiently storing, querying, and retrieving high-resolution images and video.

j. In step 510, the server application of the skin-monitoring service retrieves previously stored data concerning the Subject/patient, including but not limited to the Subject/patient's medical history, previously captured skin images and videos, and the purpose for which the Subject/patient is being monitored. This data provides the "context" in which the server application will analyze the Subject/patient's newly captured images and videos.

k. In step 511, the server application evaluates the quality of the captured images and videos to ensure that the images and videos are suitable for analysis. For example, the server application processes the images and videos to detect whether they are too light or too dark and whether position and distance of the targeted area of skin relative to the camera (or other relevant sensors) is appropriate. The threshold for acceptable quality may be determined at least in part by various parameters, such as the disease or condition for which the Subject/patient is at risk. For example, some conditions may require higher resolution images. If the images and videos were captured according to a schedule, the Subject/patient may be immediately notified whether the images and videos are acceptable or not acceptable. If the images and/or videos are not acceptable, the Subject/patient is prompted to perform the image and video capture again. If the images and videos were captured opportunistically, the images and videos that are not amenable to analysis may simply be discarded.

l. In step 512, the server application derives information from the images and videos. Without limitation, the server application may derive measurements and information relating to the physical dimensions of the targeted area of the skin (and targeted features thereon), the color of the targeted area of the skin (and targeted features thereon), the thermal map of the targeted area of the skin (and targeted features thereon). The server application may also compare the images and videos and/or derived measurements and information to previously captured images and videos of the skin of the same Subject/patient, a known healthy person, or a person known to be affected by a particular Condition or disease. For example, the server application may compute the change in the color of the Subject/patient's targeted area of skin since the last image or video was captured or compute the difference in color between the Subject/patient's targeted area of skin and a similar targeted area of skin known to be healthy.

m. In step 513, the server application applies machine learning and data analysis techniques known in the art to estimate the likelihood that a health condition or disease is present and the severity of the disease or Condition. The health analysis is configurable in multiple ways by the Subject/patient, Professional, and/or a system administrator. For example, the server application may be configured to analyze the Subject/patient's health with respect to only a specified Condition for which the Subject/patient has a known elevated risk, or the server application may be configured to analyze the Subject/patient's health with regard to a broader set of diseases and conditions.

Similarly, the server application may be configured to estimate whether the severity of an existing Condition has increased or decreased or the server application may be configured to only note the presence of a Condition without regard to severity.

n. In step 514, the server application determines whether the health analysis should result in any further action by the skin-monitoring service. The most common action to be taken by the skin-monitoring service is to notify the Subject/patient and/or service provider. The conditions under which a notification is delivered to the Subject/patient and/or service provider is also configurable. For example, the server application may be configured to provide a notification when a new Condition is detected, when an existing Condition is no longer detected, or when the severity of a Condition has changed. Since the health analysis generally produces probabilistic estimates, the server application is also configurable with respect to the confidence thresholds required for a notification to be sent. For example, the Professional may elect to only receive notifications when the health analysis is virtually certain that a Condition has arisen, when there is even a small chance that a Condition has arisen, or anything in between.

o. In step 515, if a notification to the Subject/patient and/or Professional is generated due to a potential health change in the Subject/patient, the Subject/patient and/or Professional may elect to request a video conference with each other using the web-based or app-based interface of the skin-monitoring service. If both parties agree to participate in a video conference, which may be scheduled for some future time, the skin-monitoring service establishes an audio and video link between the two. The audio and video link enables the Professional to gather more information about the Subject/patient's symptoms, including non-skin related symptoms, if any, and conduct further visual inspection of the Subject/patient. Alternatively, the skin monitoring service may facilitate some other form of communication between the Subject/patient and Professional, such as an audio or text-based chat. The Professional may then determine whether the Subject/patient requires further medical attention. For example, the Professional may elect to schedule an in-person appointment for the Subject/patient or obtain laboratory testing for the Subject/patient.

Skin Autofluorescence.

Skin autofluorescence is a non-invasive measure of the level of tissue accumulation of advanced glycation end products, representing cumulative glycemic and oxidative stress (OS).[53]

[53] https://diabetesjournals.org/care/article/31/3/517/26055/Skin-AutofluorescenceA-tool-to-identify-type-2.

Skin autofluorescence is the abnormal fluorescence of the skin of patients with either diabetes mellitus or excessive oxidative stress when exposed to ultraviolet light. It results from the accumulation of advanced glycosylation end products (AGES) in tissues. AGES accumulation has been linked to cardiovascular diseases, impairments in glucose tolerance, and renal failure.

In an embodiment, the autofluorescence of human skin can be used to measure the level of AGES, which are present in higher quantities during several human diseases.[54]

[54] See https://en.wikipedia.org/wiki/Autofluorescence.

Studies have shown a relationship between skin autofluorescence and diabetes complications, as well as the predictive value of skin autofluorescence for total and cardiovascular mortality in type 2 diabetes. Indeed, there is empirical evidence that skin autofluorescence is an independent predictor of development of microvascular complications in a population of patients with well-controlled type 2 diabetes. Skin autofluorescence has also shown independent predictive value for cardiovascular mortality and morbidity in patients with type 2 diabetes and in patients with end-stage renal disease undergoing hemodialysis.[55]

[55] https://diabetesjournals.org/care/article/31/3/517/26055/Skin-AutofluorescenceA-tool-to-identify-type-2.

Skin autofluorescence is used in an embodiment as a helpful clinical method to identify type 2 diabetic patients at risk for developing any microvascular complication, neuropathy, and (micro) albuminuria.[56] The noninvasive and time-saving application of skin autofluorescence makes the autofluorescence reader an easy clinical tool that is useful in the outpatient clinic in risk assessment and for monitoring changes in accumulation of tissue AGES reflecting long-term glycemic stress.[57]

[56] Albumin is a type of protein that is normally found in the blood. Your body needs protein. It is an important nutrient that helps build muscle, repair tissue, and fight infection. But it should be in your blood, not your urine. When you have albumin (protein) in your urine, it is called "albuminuria" or "proteinuria." One of the main jobs of your kidneys is to filter your blood. Your kidneys keep important things your body needs inside your blood, like protein. They also remove things your body doesn't need, like waste products and extra water. If you have albuminuria, It may be an early sign of kidney disease, but your doctor will check you again to make sure albuminuria is not caused by something else, like not drinking enough water. If your doctor suspects that you have kidney disease, the test for albumin will be repeated. Three positive results over three months or more is a sign of kidney disease. https://www.kidney.org/atoz/content/albuminuria.

If kidneys are healthy, you should have very little protein in your urine—or even none. But if your kidneys are damaged, protein can "leak" out of the kidneys into your urine.https://www.kidney.org/atoz/content/albuminuria. Albuminuria is defined as an "abnormal loss of albumin in the urine". Albumin is a type of plasma protein normally found in urine in very small quantities. https://www.bing.com/search?q=albumnuria+meaning&cvid=030603dbab00431987832566d9a21dS&aqs=edge, 0.014j69164.25342j0j4&FORM=ANAB01&PC=DCTS. 0.014164.2534&FORM=ANAB01&PC=OCTS.

[57] https://diabetesjournals.org/care/article/31/3/517/26055/Skin-AutofluorescenceA-tool-to-identify-type-2.

Multivariate analyses showed skin autofluorescence as a predictor for development of any microvascular complication along with A1C, for development of neuropathy along with smoking, and for development of (micro) albuminuria together with sex, A1C, and diabetes duration.[58]

[58] https://diabetesjournals.org/care/article/31/3/517/26055/Skin-AutofluorescenceA-tool-to-identify-type-2.

Studies have provided evidence that skin autofluorescence is an independent predictor of development of microvascular complications in a population of patients with well-controlled type 2 diabetes. Separately, this also holds for the development of neuropathy and (micro) albuminuria (and in univariate analysis for retinopathy). This noninvasive marker of tissue AGE accumulation may reflect the deleterious effects of long-term glycemic and oxidative stress.[59] It has also been evidenced in studies [see Meerwaldt et al.[60]] that skin autofluorescence is a predictor of 5-year coronary heart disease and mortality in diabetes.[61]

[59] https://diabetesjournals.org/care/article/31/3/517/26055/Skin-Autofluorescence A-tool-to-identify-type-2.

[60] Meerwaldt R, Lutgers H L, Links T P, Graaff R, Baynes J W, Gans R O B, Smit A J: Skin autofluorescence is a strong predictor of cardiac mortality in diabetes. Diabetes Care 30:107-112, 2007.

[61] https://diabetesjournals.org/care/article/31/3/517/26055/Skin-Autofluorescence A-tool-to-identify-type-2.

An embodiment uses a portable autofluorescence imaging devices for skin.[62] The AGE readers are non-invasive monitoring devices that uses ultra-violet light to excite autofluorescence in human skin tissue.

[62] See https://www.speieddigityallibrary.org/jorunals/Journal-of-Biomedical-Optics/volume-19/issue-08/085002/Autofluorenscence-imaging-device-for-real-time-detection-and-tracking. mal-of-Biomedical- Optics/volume-19/issue of/10.1117/1.1BO.19.8.085002.full?SSO=1; see https://www.diagnoptics.com/age-reader/.

One Embodiment of the Invention System Uses a Portable Autofluorescence Imaging Device for Skin to Detect and Analyze Data on a Subject Related to AGES in the Subject's Tissues and Other Subject "Conditions" Through Use of the Invention System as Described in the patent application In addition, there are portable handheld fluorescence imaging devices for use in a clinical setting in the detection of wounds containing bacteria in the marketplace known to those skilled in the art.[63]

[63] See https://lermagazine.com/market-mechanics/handheld-flurorence-imaging-device-for-wound. management-receives-fda-510k-clearance. See also https://www.bing.com/videos/search?q=MolecuLight+i%3aX&docid=608005423599276848&mid=D81026E0B08D6F37391AD81026E0B08D6F37391A&view=detail&FORM=VIRE.

Some additional information about the embodiments follow:

1. A way to record and transmit "usable" two-dimensional and optionally three dimensional color pictures and videos of the Subjects Skin or targeted areas thereof via a remote connection for one or more of the purposes of the invention. In all the embodiments, the "Subjects" who receive the skin evaluation and/or treatment can include:
   1. Living conscious human beings.
   2. Living unconscious human beings (e.g., in an ambulance or in surgery). Note: Changes in skin color often happen right before someone dies.
   3. Dead human beings (e.g., in a hospital, or in a police or coroner examination). Note: Changes in skin color often happen right before someone dies.
   4. Living conscious animals (e.g., animal "pets" such as dogs, cats, horses, etc., and "livestock" such as cows, steers, pigs, chickens, sheep, and fish on fish farms, etc.).
   5. Living unconscious animals (e.g., unresponsive but alive pets or livestock, animals in surgery, etc.).
   6. Dead animals (e.g., in a pet hospital, on a livestock farm, in a zoo, in a fish farm, etc.).

XX. OTHER EMBODIMENTS

A. Embodiments describe a new way to examine (or have examined) the skin (or targeted portions thereof) of Subjects by human beings and/or artificial intelligence software or any kind of machine language software, for the proposed Applications of the invention, in real-time, near real-time, or delayed time.

1. Enabling a Subject-user (or the owner of a Subject-user if the Subject is an animal) to through various potential input means (which is part of the invention and will be described herein) obtain a real-time, near real-time, and/or delayed time diagnostic and/or inquisitive examination of the skin (or targeted portions thereof) of the Subject, either using or not using the Subject's prior reference skin (or targeted portions thereof) examination (using the invention or not), from the location of Subject's home, or from another "remote" location, such as, for example, without limitation, a local pharmacy, school, college, government facility, physician's office, eye-professional's office, or hospital (for the Subject without a version of the skin video input device portion of the invention, or to use a potentially higher quality version of the skin video input device portion of the invention than the version of the device owned or leased by or in the possession of the Subject).

2. Enabling a third-party non-professional (including, without limitation, caregivers of the Subject, parents of minor children who are the Subject, nurses, and paraprofessionals such as ambulance personnel, police or police detectives, etc.) to obtain a real-time, near real-time, and/or delayed time diagnostic and/or inquisitive examination the skin (or targeted portions thereof) of the Subject from the Subject's home or from the location of the third-party non-professional, wherever that might be).

3. Enabling a third-party professional (including, without limitation, dermatologists, medical doctors, surgeons, cosmetologists, etc.) to obtain a real-time, near real-time, and/or delayed time diagnostic, and/or inquisitive examination the skin (or targeted portions thereof) of the Subject.
   a. Enabling the skin (or targeted portions thereof) of a Subject to be examined, or enabling the Subject to have his, her or its skin (or targeted portions thereof) examined, whereby a number of combinations and permutations of indications of:
      (i) Potential health issues (both skin health issues per se as well as other health issues for which the skin (or targeted portions thereof) may be indicators. Please note that the skin (or targeted portions thereof) can harbor signs of various chronic diseases and other health conditions (in addition to skin diseases per se) which a trained human skin doctor can spot, and based on this invention expert machine learning software and deep learning software can and will spot, enabling the Subject to seek a potential further examination and treatment;
      (ii) New biometric identifiers and measurements for identification of the Subject for miscellaneous purposes.

The data can be reviewed and analyzed concurrently, in either real-time, near real time (real time other than processing and/or network delays), or delayed-time, thereby saving the Subject time, effort, and potentially "thought" (i.e., the effort by the Subject to think about and/or remember to have his or her skin (or targeted portions thereof) examined or measured for any of the purposes of the invention) and allowing for an efficient comprehensive examination of the Subject's skin (or targeted portions thereof), and the potential creation, with the appropriate permission of the Subject (or for a Subject who is an animal, the Subject's owner) of an skin (or targeted portions thereof) database for:

(a) Use as a future reference with respect to the Subject; and/or
(b) Use for skin (or targeted portions thereof) research for humanity and animals in general, including without limitation:
   (x) Building and growing new and existing "deep learning" AI systems for better evaluation and/or diagnosis of skin health and potential related body health issues;
   (y) Building expert software to diagnosis and better understand individual issues related to skin (or targeted portions thereof) as they exist in standalone portions of the skin and in various combinations and permutations with other areas of the skin (or targeted portions thereof) and body using "Big Data" and machine learning software and deep learning software, in ways presently known to those skilled in the art, to tease out new correlations that can in the future be used for better health prognosis.

Traditional skin examinations for humans means the human whose skin (or targeted portions thereof) is to be examined must arrange for an appointment and travel to the location of a Professional who conducts a frequently expensive and time-consuming face-to-face/in-person skin tests. Traditional skin examinations of the skin (or targeted portions thereof) of the skin (or targeted portions thereof) of and for animals means bringing the animal a distance to a veterinarian, or having the veterinarian travel a distance to the location of the animal, to examine the skin (or targeted portions thereof) of the animal face-to face/in-person. The invention allows for many if not most of the traditional skin (or targeted portions thereof) examination tests for humans and/or animals to be conducted remotely, at-a-distance, in real-time, near real-time or delayed time.

The purpose of the real-time, near real-time, and/or delayed time, and or Once-or-More-Removed Skin (or targeted portions thereof), skin Examination (in real-time or delayed) (together, the "Skin Exam") is in part as follows:
1. To attempt to widely broaden access to skin care by Subjects having the ability to measure or attempt to measure, through a review of the fixed static state and/or dynamic state of the Eye(s) of the Subjects over a fixed period of time, for:
   a. research purposes (including building a database of comparative data of skin);
   b. health diagnostic purposes (the identification of potential or actual health problems), including without limitation follow-up examinations of Subjects following treatment of the skin of the Subject;
   c. prescriptive purposes (the fixing of certain problems, such as prescribing eyeglasses or contact lenses);
   d. general prudent periodic health check-up purposes; and
   e. the health of and changes over time in the skin (or targeted portions thereof) and other related aspects of the health (insofar as the skin (or targeted portions thereof) reveals another potential disorder with the non-skin portion of the physical body, or an allergy (new or existing), or with a behavior that affects health (such as the usage of certain prescription or illegal drugs) of the Subjects whose skin (or targeted portions thereof) is being examined through such an examination of the skin (or targeted portions thereof).

XXI. ANIMALS

Skin can also be checked in animals, for example, but without limitation, as in the following embodiments:

A. Cats.

Cat skin problems are fairly common. Parasites such as fleas or mites, fungal or bacterial infections, allergies, stress, injury, or more rarely, hormonal imbalances cause cat skin problems. Listed below, without limitation, are a few common cat skin problems.

(i) Abscesses.

An abscess is a painful collection of pus at the site of a bite or puncture wound. Abscesses form a firm swelling that becomes soft with time and can rupture and spill out purulent discharge.

(ii) Ear Mites.

This condition causes tremendous itching and irritation, and if left untreated, can lead to bacterial infection.

(iii) Feline Acne.

In feline acne, comedones (also known as blackheads) form on the underside of the chin and edges of the lips.

(iv) Contact Dermatitis.

Cat skin problems sometimes show up as red, itchy bumps. With contact dermatitis, you will see those red, itchy bumps and inflamed skin at the site of contact with a chemical or other irritant.

(v) Flea Allergy Dermatitis.

Some cat skin problems, like flea allergy dermatitis, manifest as itchy, pimple-like bumps that form over the base of the tail, back of the rear legs and inner thighs. Although many cats can get fleas and not have any reaction, in sensitive cats it can take just one flea bite to cause hours or days of symptoms.

(vi) Food Allergy Dermatitis.

Some cats are very sensitive to certain ingredients or preservatives in their food. This sensitivity can result in severe itching over the head, neck and back, and swelling of the eyelids. It is often complicated by hair loss and oozing sores from constant scratching and biting.

(vii) Psychogenic Alopecia.

This is the thinning of the fur in a stripe down the back or on the abdomen caused by compulsive self-grooming. Stress often causes compulsive grooming.

(viii) Ringworm.

Ringworm is a fungal infection that is highly contagious to other animals and to humans. Symptoms of this skin condition include round patches that show central hair loss with a red ring at the periphery. In some cats, it only shows as broken hairs around the face and ears.

(ix) Sunburn.

Cats with light-colored fur and hairless breeds such as the Sphynx are very prone to sunburn and should be kept out of direct sunlight between 10 a.m. and 2 p.m. to reduce the risk of sunburn and minimize the long-term risk of developing skin cancers such as melanoma.

(x) Scabs.

Scabs occur after something, usually trauma, opens the skin enough to cause bleeding. When the blood clots and closes the injury, a scab is formed.

B. Dogs.

There is a long list of canine skin diseases and conditions that need to be considered before diagnosing any problem. Listed below, without limitation, are a few common dog skin problems.

(i) Dog Flea Allergy. Dog flea allergy is the leading cause of skin problems.

(ii) Atopy.

Atopy is an environmental dog allergy.

(iii) Dog Food Allergy.

Signs of food allergy can include skin rash. Allergies are increasing in dogs, and food allergies are the third most common culprit.

(iv) Mange.

Mange is a parasitic condition that causes patches of baldness, is the next leading cause, and is primarily seen in puppies.

(v) Alopecia.

Alopecia is hair loss, and it occurs in four patterns: (i) Focal-small single patch, (ii) Multi-focal-several small circular patches. Looks moth-eaten, (iii) Regional-alopecia that occurs in one region of the body such as a single leg, and (iv) Symmetrical—hair loss on opposite sides of the body. Most conditions that involve canine hair loss that occurs spontaneously (spontaneous alopecia) are caused by a hormonal problem (endocrine system) such as hypothyroidism. Other causes are folliculitis which is causes by inflammation of the hair follicle due to canine ringworm or a bacterial infection. Often a cause cannot be found. Patchy hair loss on the head and face is a symptom of mange. Patches of dog hair loss can also indicate ringworm or allergy.

(vi) Hyperpigmentation.

Hyperpigmentation occurs when the skin has too much pigmentation, resulting in black dog skin spots. Causes of dog black skin spots include allergy, Malassezia dermatitis (yeast infection), and Endocrine disorders. If the black skin spots become black scabs on dog or crusts, it is a symptom of a condition call Alopecia X or Cushing's Disease.

(vii) Seborrhea.

Seborrhea refers to scaling skin which occurs when skin particles accumulate on the outer layer of the skin. Dog seborrhea sicca refers to dog dandruff, while greasy or oily skin is referred to as seborrhea oleosa. Canine seborrhea is caused by allergy, hormonal problems, bacterial infections, fungus, and tumors. Seborrhea can also cause scars, bumps and pimples on the skin.

(viii) Foot and Nail Problems.

If mostly on the footpads, it could be Pemphigus, an autoimmune disease that causes lesions or pustules. Issues between the toes is frequently caused by a fungal infection called foliculitis or a bacterial infection called furunculosis. In many cases the condition starts as a fluid-filled nodule between the dog toes. The nodule ruptures, forming a furuncle in the toe area. Nail bed problems are often caused by bacterial paronychia resulting in malformed or broken nails. Foot itch (Pedal puritus, Malassezia dermatitis) is typically caused by the yeast Malassezia. The condition is usually seen on all 4 feet. The condition can cause the dog to injure itself when reacting to the condition.

(ix) Hot Spots (Acute Moist Dermatitis).

Hot spots are caused by the removal of a superficial layer of skin due to scratching or biting.

(x) Rash (Erythema).

When a dog's skin has a rash or is red in color and is comprised of pustules, papules (small, red circular dog skin pimples less than 1 cm in diameter) and macules, it implies that the problem is: allergy, parasites, infection, or immune-mediated skin diseases.

(xi) Acne and Dog Pimples.

Dog pimples or acne can have multiple causes including skin tumors, allergy, infection (fungal, bacterial), fleas and mites. Some dogs can get acne with pimples around the mouth and chin.

(xii) Warts (Canine Papillomatosis).

Warts (papillomavirus) are non-cancerous-benign contagious dog skin pumps. They are transmitted via indirect and direct contact. Warts start as small papules and become larger to become small, cauliflower warts. They are found on the conjnctivae (eyes), buccal mucosa (lining of the cheeks and mouth), gums, tongue and lips.

C. Horses.

Equine skin diseases have a way of holding your attention, while still remaining mysterious. Listed below, without limitation, are a few common horse skin problems.

(i) Rainrot (Rain Scald).

Rainrot is a bacterial infection that appears as scabby crusts that form raised bumps with upright tufts of matted hair. The crusts form on parts of the body that are chronically damp—often along the topline and where rain runs off down the barrel, shoulders or hindquarters, but also on the lower legs or faces of horses who regularly stand in mud or graze tall, wet grass. Over time, the crusts peel off, leaving small, round bare spots; pus may also be seen under newly sloughed scabs.

(ii) Ringworm (Fungal Dermatitis).

Ringworm is a fungal infection that appears as rounded hairless patches with crusty, scabby skin. The lesions are most common on the face, neck, shoulders, chest or under the saddle or girth, but they can appear anywhere on the body. The affected areas may be sore or itchy, but they often cause no discomfort, and the horse may appear otherwise healthy. Left untreated, the lesions will continue to grow and spread. Although infections might heal eventually on their own, the horses would be highly contagious until they do.

(iii) Warts (Papillomas).

Warts appear as raised gray or pink cauliflower-like growths that are usually fairly small, not much bigger than peas. They may appear singly or in clusters, most commonly on the muzzle or around the eyes but also occasionally on the ears, genitals and lower legs.

(iv) Aural Plaques (Papillary Acanthoma, Ear Papillomas).

This appears as flat, crusty, raised white lesions inside the ears; underneath, the skin may be pink and sensitive. Both ears are likely to be affected. They are not likely to shrink or go away on their own.

(v) Eosinophilic Granuloma with Collagen Degeneration (Nodular Collagenolytic Granuloma, Nodular Necrobiosis, or Simply Nodules).

This appears as distinct, firm nodules about the size of a dime or smaller, found usually in the neck, back and withers. Several small nodules may cluster together to form what appears to be a larger lump. The skin above is normal, with no hair loss, and the nodules do not contain pus. The bumps can occur in horses of any age, breed or gender.

(vi) Mange.

Mange is a parasitic infection caused by several species of tiny mites that can barely be seen by the naked eye. It appears as small, round bumps at first, soon followed by bald spots, with scaly, thickened skin, usually on the lower legs of draft horses with heavy feathering, although any horse can be affected. In more serious cases the skin may be rubbed raw and show signs of secondary infections. Mange causes itching, and horses will rub, stamp and bite at their legs. In rare cases, mange may appear on other parts of the body. It can cause permanent thickening and scarring of the skin that can impede the movement of the pastern joints.

(viii) Lice (Pediculosis).

It appears as hair loss from rubbing, usually appearing first on the shoulders and neck, as well as on the head and the base of the mane and tail. Affected areas are intensely itchy and may also have abrasions and scabs from rubbing and possibly secondary infections. Flattened insects up to two to four millimeters long may be visible if the hair is parted and the skin examined in good light. Pale, translucent eggs may be attached to nearby hairs. Severe cases can cause anemia.

XII. CONCLUSION

Who among us can track all the potential diseases and conditions of the skin (or targeted portions thereof), body, and/or mind mentioned in the Schedules hereto and referenced herein? Who among us seeks skin care as often as we should, and does not wait until something truly negative happens before we act? Who among us can detect what is often an asymptomatic disease or condition that could be uncovered early by a skin examination? Who among us has the time, much less the financial resources (even with health care insurance), to have his or her skin examined and monitored as frequently, periodically, accurately, and as hassle-free as the invention is able to do?

Just as some cars can notify the driver of potential issues with respect to the car without the driver needing to think, in a similar way and in certain modes the invention—once set—can notify the Subject/user of potential concerns with respect to the Subject/user's the skin (or targeted portions thereof), and/or body health issues without the Subject/user needing to think.

Functionality/Utility of the Invention/How It Works.

An embodiment uses a portable and/or mobile wireless, and comparatively inexpensive system with a novel method of conducting various types of skin (or targeted portions thereof) examinations of Subjects remotely from-a-distance in either real-time, near real-time, or delayed time. The skin examinations can be conducted at a distance by (i) eye professions, or (i) computers in the cloud using both proprietary and/or open source software, mated with AI deep learning software (with a view to over time replacing a number of the functions of current eye professionals, by making the skin (or targeted portions thereof) examination process better, faster, cheaper, and more accurate by removing some of its current subjectivity).

The embodiments use the following hardware and/or software to operate as described herein:
1. The "Input-Output Device".
    a. A portable or mobile wireless, portable audio and video transmitting and audio and video receiving "device" (the "Input-Output Device") with a (A) wireless transceiver, (B) a display (the "Display"), (C) camera or webcam with the ability to take color digital photos and digital streaming video (collectively, the "Camera"), (D) an optional augmented reality scanner to allow for quasi-3 dimensional photos and videos to be taken, recorded and transmitted, and (E) an optional 3-dimensional camera or multiple cameras to operate to obtain 3 dimensional photos and videos of skin (or targeted portions thereof) to be taken, recorded and transmitted. Such an Input-Output Device, includes, without limitation:
        i. Any device with the functionality described above.
        ii. A smartphone, with the functionality described above.
        iii. A pad computer, such as an iPad or an Android-based pad computer, with the functionality described above.
        iv. A laptop computer, with the functionality described above.
        v. A desktop computer, with the functionality described above.
        vi. A thin client, with the functionality described above.
        vii. A zero client, with the functionality described above.
2. The Chamber.
    A device (hereinafter the "Chamber"), similar to a periscope, in which the Subject looks though one end of the Chamber (for the human, with or without glasses or contacts, depending on the nature of the Eye(s) exam), with the Input-Output Device Display and its Camera and display screen being "affixed" and facing inward to the other end of the Chamber. When the Subject looks through the Chamber, magnifying mirrors or non-distorting magnifying lens(es) in the Chamber magnify the Subject's skin (or target areas thereof) and the Subject sees the lit color display screen of the Input-Output Device and its Camera.
    a. The Chamber performs several important purposes:
        i. It generally keeps the skin (or targeted portions thereof) of the Subject at a fixed focal length from the Camera of the Input Output Device, and helps hold the Camera and color display screen steady as the Subject looks towards them.
        ii. Through the Chamber's internal mirrors and/or lens(es), the Chamber enlarges the Subject's skin (or targeted portions thereof) so the Camera is able to better capture the image of the unique biometric features of the Subject (specifically the skin pores/hair follicle patterns, the blood vein patterns, and or the thermal patterns, or any combination or permutation thereof, and the skin (or targeted portion thereof).
    In an alternative embodiment, a macro lens is added on the Camera to better capture the image of the unique biometric features of the Subject (specifically the skin pores/hair follicle patterns, the blood vein patterns, and or the thermal patterns, or any combination or permutation thereof, and the skin (or targeted portion thereof).
        iii. The Chamber keeps control over the level of light for the skin exam, so each exam session is an "apples-to-apples" comparison, and so various tests on the Subject's skin (or targeted portions thereof) can be performed using light in various ways.
            (a) The level of light entering the Chamber can be controlled by a "dimmer knob or slide" to increase, decrease, strobe, or turn off, etc., the external light on the outside of the Chamber. Alternatively, and perhaps preferably, the light on the outside of the Chamber can be controlled at a distance by the person or software on the host end of the system.
            (b) The brightness of the Input Output Device video display can be altered by the Subject-user or someone near the Subject-user or from the host side.
            (c) The Chamber can potentially be lengthened or shortened in different embodiments.
            (d) The Chamber contains mirrors to enlarge the skin (or targeted portions thereof) of the human or animal looking into the Chamber so the Camera of the Input-Out Device sees the skin (or targeted portions thereof) much larger than would otherwise be the case.
            (e) An Augmented Reality Scanner. An AR scanner activates the camera, the software calculates the perspective and puts a digital layer over it. This makes it possible to add computer generated information to that digital layer in the world the camera sees. AR scanner apps exist that enable any kind of digital information to be placed into the real world very easily.

(f) An extra camera or 3D camera to take 3D video (g) The Chamber has a light inside of it that can be turned on and off and can increase or decrease the brightness of the light (the "Scope Light"), which can be directly controlled by the User or indirectly controlled by professional at a distance. In an Alternative embodiment: Control over the Input-Output Device can be provided to the Professional at a distance through the means of software known to experts skilled in the art (e.g., such as LOG-MEIN), and the professional can take control of the session.

1. User launches the app in the Input-Output Device (the App) and affixes the Chamber to the Input-Output Device.
2. The App allows User by voice or the professional to operate the Input-Output Device.

Another embodiment uses a head-up display or heads-up display, also known as a HUD as the display part in any of the embodiments described herein.

A HUD is conventionally formed of a transparent display that presents data without requiring users to look away from their usual viewpoints. Although HUDs were initially developed for military aviation, HUDs are now used in commercial aircraft, automobiles, and other (mostly professional) applications.

Primary Components of a Typical HUD. A typical HUD contains three primary components: a projector unit, a combiner, and a video generation computer.

The projection unit in a typical HUD is an optical collimator setup: a convex lens or concave mirror with a cathode ray tube, light emitting diode display, or liquid crystal display at its focus. This setup produces an image where the light is collimated, i.e. the focal point is perceived to be at infinity.

The combiner is typically an angled flat piece of glass (a beam splitter) located directly in front of the viewer, that redirects the projected image from projector in such a way as to see the field of view and the projected infinity image at the same time. Combiners may have special coatings that reflect the monochromatic light projected onto it from the projector unit while allowing all other wavelengths of light to pass through. In some optical layouts combiners may also have a curved surface to refocus the image from the projector.

The computer provides the interface between the HUD (i.e. the projection unit) and the systems/data to be displayed and generates the imagery and symbology to be displayed by the projection unit.

Types. Other than fixed mounted HUD, there are also head-mounted displays (HMDs). Including helmet-mounted displays (both abbreviated HMD), forms of HUD that features a display element that moves with the orientation of the user's head.

Generations. HUDs are split into four generations reflecting the technology used to generate the images.

a. First Generation.

Use a CRT to generate an image on a phosphor screen, having the disadvantage of the phosphor screen coating degrading over time. The majority of HUDs in operation today are of this type.

b. Second Generation.

Use a solid state light source, for example LED, which is modulated by an LCD screen to display an image. These systems do not fade or require the high voltages of first generation systems. These systems are on commercial aircraft.

c. Third Generation.

Use optical waveguides to produce images directly in the combiner rather than use a projection system.

d. Fourth Generation.

Use a scanning laser to display images and even video imagery on a clear transparent medium.

Newer micro-display imaging technologies have been introduced, including liquid crystal display (LCD), liquid crystal on silicon (LCoS), digital micro-mirrors (DMD), and organic light-emitting diode (OLED).

In 2012 Pioneer Corporation introduced a HUD navigation system that replaces the driver side sun visor and visually overlays animations of conditions ahead; a form of augmented reality (AR). Developed by Pioneer Corporation, AR-HUD became the first aftermarket automotive Head-Up Display to use a direct-to-eye laser beam scanning method, also known as virtual retinal display (VRD). AR-HUD's core technology involves a miniature laser beam scanning display developed by Micro Vision, Inc.

In recent years, it has been argued that conventional HUDs will be replaced by holographic AR technologies, such as the ones developed by WayRay that use holographic optical elements (HOE). The HOE allows for a wider field of view while reducing the size of the device and making the solution customizable for any car model. Mercedes Benz introduced an Augmented Reality based Head Up Display while Faurecia invested in an eye gaze and finger controlled head up display.

A prototype HUD has also been developed that displays information on the inside of a swimmer's goggles or a scuba divers' mask. HUD systems that project information directly onto the wearer's retina with a low-powered laser (virtual retinal display) have also been developed. [Quoting from https://en.wikipedia.org/wiki/Head-up_display#cite_note-3 8]

Optical Spectrometry and New Portable Spectrometers on a Chip.[64]

See https://www.nxtlifescience.com/medtech/light-analying-lab-on-a-chip-opens-door-to-widespread-use-of-protable-spectrometers/#:~:text=Light-analyzing%20%E2%98ab%20%on%20a%20chip%E2%80%99%20opens%20door%20to.2002%20This%20article%20was%20originally%20published%20by%20BioEngineering.

Scientists have developed powerful, ultra-tiny spectrometers that fit on a chip and are operated using artificial intelligence. Previously, the smallest spectrometers were about the size of a grape, but the newly developed ones, which can achieve high resolution, could fit on the end of a human hair.

Spectrometers measure the strength of light at different wavelengths, and are useful in identifying "objects" by measuring the spectrum of light they absorb. In medicine, for example, spectrometers are already being tested for their ability to identify subtle changes in human tissue such as the difference between tumors and healthy tissue.

Integrating the new portable ultra-tiny spectrometers on smartphone cameras or their equivalent could make them hyperspectral cameras. Those hyperspectral cameras could capture and analyze information not just from visible wavelengths but also allow for infrared imaging and analysis.

In one embodiment of the invention, one or more portable ultra-tiny spectrometers are used on and as part of a smartphone-type device or on or as part of other "input devices" are described in the patent application, to collect relevant Subject skin data, using visible wavelengths and infrared and other wavelengths of light for imaging and analysis.

Holographic Optical Element. A holographic optical element (HOE) is an optical element (such as a lens, filter, beam splitter, or diffraction grating) that is produced using holographic imaging processes or principles. Dichromated gelatin and photoresists are among the holographic recording materials used in forming holographic optical elements.

One use of a holographic optical element is in thin-profile combiner lenses for optical head-mounted displays. A reflective volume hologram is used to extract progressively a collimated image that was directed via total internal reflection in an optical waveguide. The spectral and angular Bragg selectivity of the reflective volume hologram makes it particularly well-suited for a combiner using such light sources as RGB LEDs, providing both good see-through quality and good quality of the projected image. This usage has been implemented in smart glasses by Konica Minolta and Sony. [https://en.wikipedia.org/wiki/Holographic_optical_element]

The invention, in a manner known to those skilled in the art, proposes to use HUDs, HMDs, and/or HOEs, alone or in any combination or permutation together, as a form of output for use by Professionals and potentially by Subjects or their guardians or, in the case of animals, owners as part of the display.

AI and Vector Databases.

AI can sort and process data meaningfully.

A relatively new category of database management which has created a paradigm shift for making use of unstructured data—such as images, video, and audio—is "vector databases". Vector databases offer a mind-numbing new level of capacity to search unstructured data in particular, but can tackle semi-structured and even structured data as well.

Unstructured data generally does not fit the relational database model. In other words, it cannot be easily sorted into row and column relationships. Managing unstructured data often comes down to manually tagging the data (for instance labels and keywords on video platforms), which is extremely time-consuming and often hit or miss.

"Embedding vectors", also called "vector embeddings", "feature sets", or simply "embeddings", are numerical values—coordinates of sorts—representing unstructured data objects or features, such as a component of a photograph, select frames in a video, or any item that does not fit neatly into a relational database table. These embeddings make split-second, scalable "similarity search" possible. That means finding similar items based on the nearest matches.

Embeddings arise essentially as a computational byproduct of an AI model, or more specifically a machine or deep learning model that is trained on large sets of quality input data. A "model" is the computational output of a machine learning algorithm (method or procedure) run on data. Some current widely used algorithms include STEGO for computer vision, CNN for image processing and Google's BERT for natural language processing. The resulting models turn each single piece of unstructured data into a list of floating point values—our search—enabling embedding.

Hence, a well-trained neural network model will output embeddings that align with specific content and can be used to conduct a semantic similarity search. The tool to store, index, and search through these embeddings is a vector database—purpose-built to manage embeddings and their distinct structure.

Vector databases, with their production-ready capabilities and extremely fast search of unstructured data, can now be added to AI applications to achieve desired objectives.

One embodiment of the invention is to use a purpose-built vector database to manage embeddings of unstructured, semi-structured, and/or structured "skin data" in the form of images or video or other type of data (including, without limitation, audio data as it may relate directly or indirectly thereto). Such management includes, without limitation, storing, indexing, and searching in the vector database for, for example but without limitation, similar items based on the nearest matches.

Automated Analyzer. An automated analyzer is a medical laboratory instrument designed to measure different chemicals and other characteristics in a number of biological samples quickly, with minimal human assistance. These measured properties of blood and other fluids may be useful in the diagnosis of disease. There are many types of automated analyzers, and of note, like the instant invention, they require "minimal human assistance".

Embodiments of the Invention Describe Herein a Special Type of "Automated Analyzer"

The AutoAnalyzer is an early example of an automated chemistry analyzer using a special flow technique named "continuous flow analysis (CFA)", invented in 1957 by Leonard Skeggs, PhD and first made by the Technicon Corporation. The first applications were for clinical (medical) analysis. The AutoAnalyzer profoundly changed the character of the chemical testing laboratory by allowing significant increases in the numbers of samples that could be processed. Samples used in the analyzers include, but are not limited to, blood, serum, plasma, urine, cerebrospinal fluid, and other fluids from within the body. The design based on separating a continuously flowing stream with air bubbles largely reduced slow, clumsy, and error-prone manual methods of analysis. The types of tests include enzyme levels (such as many of the liver function tests), ion levels (e.g. sodium and potassium, and other tell-tale chemicals (such as glucose, serum albumin, or creatinine).

The automation of laboratory testing does not remove the need for human expertise (results must still be evaluated by medical technologists and other qualified clinical laboratory professionals), but it does ease concerns about error reduction, staffing concerns, and safety, and also, as earlier noted, "allowing significant increases in the numbers of samples that could be processed". The concept of better, faster, cheaper, and more objective comes to mind with respect to both an automated analyzer and the invention, each extending and improving health care and health care outcomes.

As with the automation of laboratory testing, the invention seeks to "ease concerns about error reduction" through the invention's software objectivity, while also, as noted for the AutoAnalyzer, "allowing significant increases in the numbers of samples that could be processed" (which with the invention translates to better, faster and cheaper treatment of Subjects). [https://en.wikipedia.org/wiki/Automated_analyser]

In an embodiment, an automated analyzer data for a subject is added, combined with and correlated with skin data for a Subject (as obtained and processed by the invention) in a number of ways known to those skilled in the art (including the use of relevant "if-then" and/or AI software), to obtain a relative quick and speedy analysis of if there exist meaningful and useful statistical correlations.

Body Temperature Data. Obtaining human or animal body temperature data requires first choosing the body part from which to measure it (for example, without limitation, a rectal measurement, oral measurement, auxiliary [armpit] measurement, eardrum measurement, or forehead measurement). There are various types of thermometers used to take body temperature, with the type of thermometer used a function of the body part from which temperature is being measured. The body temperature measured is always dependent on where the measurement is taken. [See generally https://www.microlife.com/magazine/fever/how-to-measure-body-temperature-correctly].

1. Human Body Temperature.

Body temperature is one of one's vital signs, and it is an important indicator of one's health. Taking a person's temperature is typically an initial part of a full clinical examination. Normal human body-temperature (normothermia, euthermia) is the typical temperature range found in humans. The normal human body temperature range is typically stated as 36.5-37.5° C. (97.7-99.5° F.). Human body temperature varies. It depends on sex, age, time of day, exertion level, health status (such as illness and menstruation), what part of the body the measurement is taken at, state of consciousness (waking, sleeping, sedated), and emotions. No person always has exactly the same temperature at every moment of the day. Body temperature is kept in normal range by thermoregulation, in which adjustment of temperature is triggered by the central nervous system. A temperature setpoint is the level at which the body attempts to maintain its temperature. When the setpoint is raised, the result is a fever. Fever, or pyrexia, happens when the body temperature rises above normal. For humans, generally speaking any body temperature above 98.6° F. represents a fever episode. Still, there can be four types: (i) a low fever happens when the body temperature does not exceed 100.4° F., (ii) a moderate fever happens when the temperature ranges between 100.4° F. and 102.2° F., (iii) the body temperature of high fever is above 102.2° F., and (iv) there is hyperpyrexia when the temperature is equal to or greater than 104° F. Most fevers are caused by infectious disease. Persistent low-grade or high-grade fevers could signal that something else is going on in your body. A number of medical conditions, including hyperthyroidism and other endocrine disorders, can heighten the body's core temperature. Hypothyroidism, or an underactive thyroid, can also slow down metabolism, which can lead to a drop in body temperature. The body temperature also changes when a person is hungry, sleepy, sick, or cold. [See generally https://en.wikipedia.org/wiki/Human_body_temperature]. [See generally https://health.clevelandclinic.org/body-temperature-what-is-and-isnt-normal/#:~: text=Temperature%20is%20one%20of%20your%20 vital%20signs%2C%20and,temperature %20at%20a%20comfortable%20level%2C%20Dr.%20 Ford%20says.]. [See generally https://steptohealth.com/the-relationship-between-body-temperature-and-fever/].

2. Non-Human/Animal Body Temperatures.

This normal body temperature is different in different types of animals.

a. Warm-Blooded Animals.

Warm-blooded animals, which are mostly mammals and birds, need to maintain a relatively constant body temperature, within a small range (just as the human body, which is a mammalian body), in order for the systems to work properly. [See generally https://vikaspedia.in/agriculture/livestock/general-management-practices-of-livestock/body-temperature]. The body temperatures of mammals range from around 97° to over 103° Fahrenheit. For example, normal body temperature for dogs and cats is 101 to 102.5 degrees Fahrenheit (38.3 to 39.2 degrees Celsius). [See generally https://vcahospitals.com/know-your-pet/taking-your-pets-temperature]. Normal body temperature for horses can range between 98 and 100 degrees. Some horses naturally run hotter than others, but individual horses tend to be fairly consistent day-to-day (which is why it is helpful to get a baseline for one's horse's temperature when he or she is healthy). "An elevated body temperature, commonly called a "fever," can be an early indication of viral or bacterial infection." [See generally https://equusmagazine.com/horse-care/horse-fever-worry#:~: text=Normal%20body%20temperature%20for%20horses% 20can%20range%20between, for%20your%20horse%E2%80%99s%20temperature% 20when %2Ohe%20is%20healthy.]. [See generally https://www.karinabrez.com/blog/2017/12/26/what-is-the-normal-body-temperature-of-a-horse]. Birds have average temperatures of around 105° Fahrenheit. [See generally https://www.goldennumber.net/body-temperatures/].

b. Cold-Blooded Animals.

Cold-blooded animals, which include most reptiles, amphibians, fish, and insects, do not maintain a constant body temperature. They get their heat from the outside environment, so their body temperature fluctuates, based on external temperatures. [See https://www. acs.org/content/acs/en/education/resources/highschool/chemmatters/past-issues/archive-2013-2014/animal-survival-in-extreme-temperatures.html]. [See also https://www.worldatlas.com/articles/warm-blooded-and-cold-blooded-animals-what-is-the-difference.html]. Fish are ectotherms or poikilotherms, both terms that describe animals that have a body temperature that is dependent on the environmental temperature. Such animals are commonly, but incorrectly, called "cold-blooded". Each species of fish has its own minimum and maximum temperature range, and the animal's health is likely to be affected at temperatures outside that range. [See generally https://fishdoc.co.uk/water-temperatures-and-fish-health/].

Determining body temperature of healthy a calf, cow and buffalo, bull, goat, and/or sheep, for example, helps to understand if the animal is affected by diseases or is healthy. If the animal gets affected by any diseases then its body temperature changes frequently. Although there are some other reasons for which temperature can change frequently, the main reason of changing temperature of the animal is: (i) the body temperature of the healthy animal become high in the morning and get reduced at evening, (ii) during mating time temperature increases highly, (iii) the body temperature gets increased at the end of gestation, (iv) the animal working hard for long time, (v) the body temperature get increased after consuming food, and (vi) the body temperature of the animal get reduced suddenly after drinking water. [See generally https://www.roysfarm.com/body-temperature-of-healthy-animal/].

In an embodiment, adding, time synchronizing, and comparing and cross-referencing (in a manner and with techniques known to those skilled in the art, and as described in the invention) a Subject's body temperature data together with a Subject's skin data (as captured by and processed as described in the invention), can potentially lead to new discoveries as well as improved health benefits for both humans and animals alike as described in the invention.

An embodiment defines using a Subject's body temperature data, as captured and processed as described above, and time synchronizing and comparing and cross-referencing that body temperature data with the skin data monitoring and analysis, as described in this document, as part of this invention ("skin data-plus").

3D Cubicle

Figure 6:
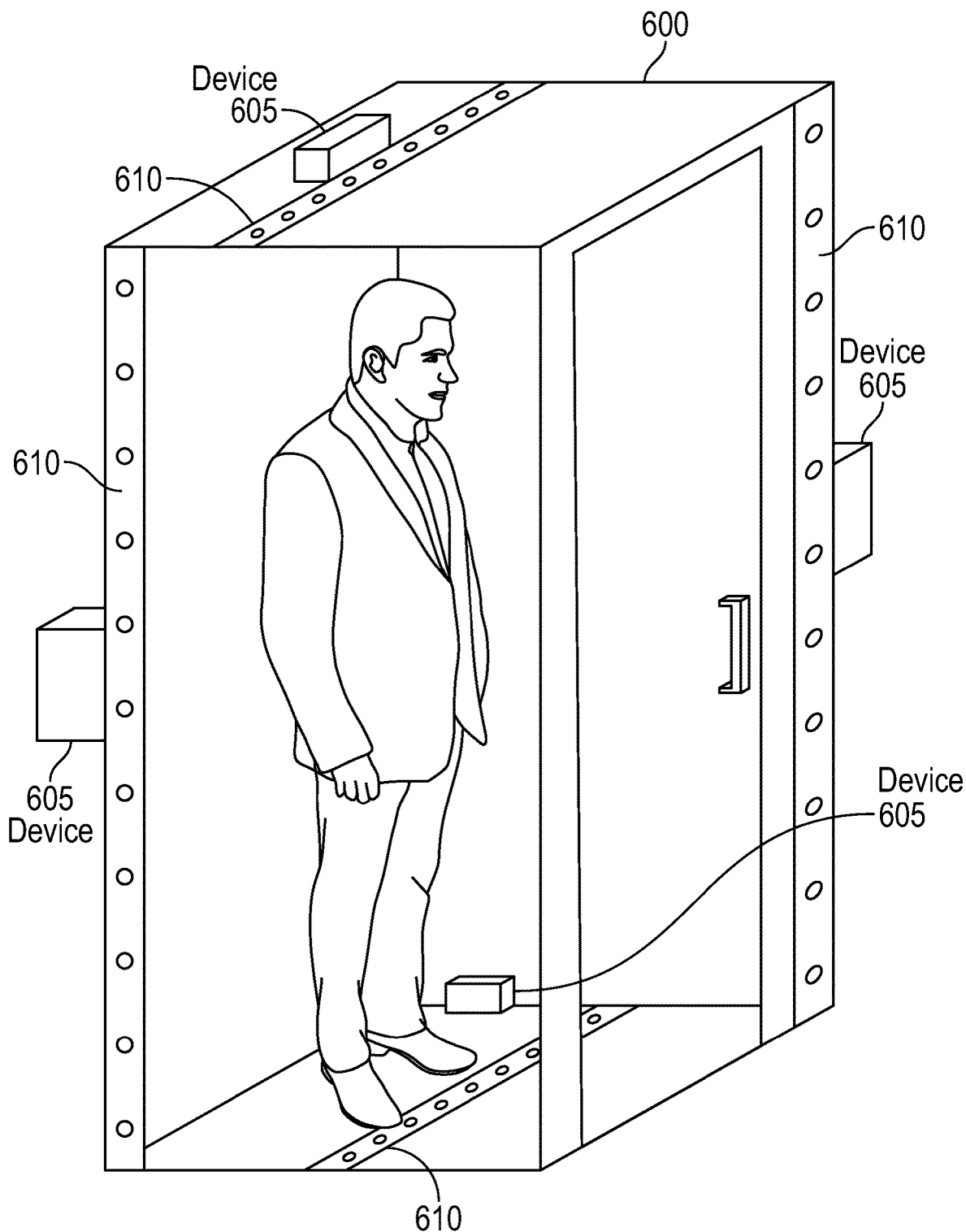
FIG. 6 shows a 3D cubicle embodiment.

A "3D Cubicle" 600, shown in FIG. 6, is a "shower-stall" type hollow structure, with a door, walls and a ceiling, for a Subject to enter and stand in to enable a 360 degree full-body scan of the skin of the Subject (a total body skin examination/TBSE). In an alternative embodiment, where a full 360 degree view is unnecessary, a lesser partial portion of the Subject's skin can be scanned.

The 3D Cubicle may be made of different substances as known in the art. Inside of the 3D Cubicle, on each of its four walls and optionally on its ceiling and floor, is the Device 605. Each device 605 is associated with, and controls and/or monitors, a strip 610 connected to the device. The strip 610 runs along the length of the wall (and/or floor and/or ceiling, if applicable) facing inward (or upward or downward in the case of the placement on the floor or ceiling). Each strip has a number of cameras and/or other imaging sensors 611 arranged in a line along the axis of the strip. This enables viewing and recording image data indicative of the skin of the Subject who is on the inside of the 3D Cubicle.

FIG. 6 shows how the 3D Cubicle device 600 can obtain images of the user's skin when the user is standing in the #D Cubicle. This enables obtaining automatic images or videos, in a similar way to the first embodiment. By its nature, the Subject cannot see the Device 605, since it is on the other side (i.e., the outside) of the 3D Cubicle, but the strips are inside. This enables the potential to obtain automatic images or videos, in a similar way to the first embodiment.

In an embodiment, one Device 605 is connected to each of the number of cameras and/or other imaging sensors 610 in a strip connected to it are inside the 3D Cubicle running along the length of the wall (and/or floor and/or ceiling, if applicable) facing inward (or upward or downward in the case of the placement on the floor or ceiling), which means cameras and/or other imaging sensors 611 in a strip are accessed or otherwise used by Device 605 sequentially.

The 3D Cubicle can have a built-in microphone (e.g., built-in) voice input for the Subject and built-in speaker (e.g., built-in) audio output. In an alternative embodiment, the microphone and speaker can be external and attachable. In any event, the 3D Cubicle preferably has an optional AI-powered chatbot (audio input and output) capability. If selected, the invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programmable and optional. Human Professionals could substitute for the invention chatbot.

Different size 3D Cubicles are contemplated for animals of various sizes.

The 3D Cubicle could be a place from which holoportation occurs.

The 3D Cubicle is a place in which AR tags can be placed on the Subject.

The 3D cubicle has multiple body-length strips 610 that run along the walls, and/or floor and ceiling, of the 3D cubicle. Each of the strips 610 has a number of individual devices 611, which in one embodiment can be cameras or sensors. The large number of devices 611 can enable a relatively quick capture of 3D full total body scan of skin data of the Subject (i.e., a 360 degree view). By surrounding the users with sensors 611, the entire body can be imaged.

In another embodiment, there can be devices 605 at front, rear, bottom and top, to immerse the surround the user. The devices can include lighting, microphones, speakers and processing elements.

Like the Magic Mirror, the 3D Cubicle can have a built-in microphone (e.g., built-in) voice input for the Subject and built-in speaker (e.g., built-in) audio output. In any event, the 3D Cubicle may have optional AI-powered chatbot (audio input and output) capability. If selected, the invention's AI-powered chatbots can assist in providing audio input and audio data output for the benefit of the Subject. For the Subject, for example but without limitation, the invention chatbot can ask questions, make commands, or attempt to inform the Subject of specified information. All of these audio outputs are programmable and optional. Human Professionals could substitute for the invention chatbot.

This 3D Cubicle is in some ways similar to the "Mirror Strip Attachment" described herein, however, there is no need for a mirror (although there could be one). In this embodiment, the Subject is consciously aware in real time of having a full total body scan exam in which Subject skin data is being captured, recorded and sent somewhere else for review in real-time, delayed time or a later time. The separate Subject skin data collected can be stitched together by software as appropriate. The AR Tagger for tagging selected areas of the Subject's skin could be automatic or triggered by a human Professional.

Also, as an alternative embodiment, the 3D Cubicle could be used to send a 3D holograph of the Subject, and on the receiving end of the holograph of the Subject, commands could be sent (by human Professional or by robot/software) to have the 3D Cubicle add AR tags to areas of interest on the Subject's skin.

Note: These 3D Cubicles could be used for animal Subjects as well as human Subjects.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.Appendices:

SCHEDULE A

The Main Layers of Skin and Their Sublayers

1. The Epidermis Layer.

The epidermis layer varies in thickness, depending on location. While it may be up to 4 millimeters thick on your feet and hands, it is often only 0.3 millimeters thick on places such as your skin, elbows, and the back of your knees.[65]

[65] https://sciencing.com/life-span-skin-cells-5114345.html.

It is made up in part of dead skin cells that are firmly packed together and constantly shedding. The epidermis contains other types of cells that perform special functions. Melanocytes make and store melanin, which protects against the sun's UV rays. When skin is exposed to the sun, they produce more of this pigment, making your skin darker. Lymphocytes and Langerhans cells fight germs by "grabbing" them and taking them to the closest lymph node. Merkel cells are nerve cells that help sense pressure.

The epidermis layer is made up of several sublayers:
  (a) The "stratum corneum" layer, the outermost sublayer. As the topmost layer it consists of dead cells that shed periodically and is progressively replaced by cells formed from the basal layer (which is made of epidermal stem cells).
  (b) The "stratum lucidum" layer (when present), which is the next sublayer down (and is found only in thick skin covering the palms, soles of feet, and digits).
  (c) The "stratum granulosum" layer, which is the next sublayer down.
  (d) The "stratum spinosum" layer, which is the next sublayer down. It is a layer of the epidermis superficial to the stratum basale beneath it, and is characterized by the presence of desmosomes (which together are a structure that forms an impermeable junction between cells).

(e) The "stratum basale" (germinatum), which is the next sublayer down, which is the innermost sublayer and the deepest one. It is made of epidermal stem cells. The stratum basale layer contains melanocytes, which are cells that which produce the melanin, the pigment primarily responsible for giving skin its color. Melanin is transferred to keratinocytes in the stratum spinosum to protect cells from UV rays.

As the stratum basale continues to produce new cells, the keratinocytes of the stratum spinosum are pushed into the stratum granulosum. The cells become flatter, their cell membranes thicken, and they generate large amounts of the proteins keratin and keratohyalin. The nuclei and other cell organelles disintegrate as the cells die, leaving behind the keratin, keratohyalin, and cell membranes that form the stratum lucidum and the stratum corneum. The keratinocytes in these layers are mostly dead and flattened. Cells in the stratum corneum are periodically shed.

Typically the lifespan of skin cells is about four weeks.[66]

[66] https://sciencing.com/life-span-skin-cells-5114345.html.

2. The Dermis Layer.

The dermis layer, or the middle layer, is composed mainly of connective tissue that connects the epidermis layer to the hypodermis layer, and presents strength and elasticity due to the presence of collagen and elastin fibers. It also contains blood vessels, hair follicles, sweat glands and other structures.

It is home to a network of nerves and capillaries that help your body cool down. Of the three layers, the dermis has the most sensory cells and sweat glands.

The dermis layer is made up of two sublayers:

(a) The papillary layer with papillae that extend into the epidermis.

(b) The reticular layer, composed of loose connective tissue, which is the next layer down.

3. The Hypodermis Layer.

The hypodermis layer, or the deepest layer, under the dermis layer of skin, contains connective tissue that connects the dermis to (x) underlying structures, (y) the integument system (which is the skin and its accessory structures), and (z) the underlying bone and muscle, and also harbors adipose tissue for fat storage and protection.

Cavities in this layer are filled with storage tissue (fat and water) that acts as a shock absorber to bones and joints and also serves as insulation. This is where vitamin D is produced when skin is exposed to sunlight. Blood and lymph vessels, nerves, sweat, oil and scent glands and hair roots are also found at this level.

Since skin is regularly exposed, it requires frequent cell regeneration. When you get a cut or scrape, skin cells divide and multiply, replacing the skin you have lost. Even without injury, skin cells routinely die and fall off. You lose 30,000 to 40,000 dead skin cells each minute, which is about 50 million cells every day.[67]

[67] https://sciencing.com/life-span-skin-cells-5114345.html.

While we sometimes notice the shedding of old skin, most of the time these cells are too tiny to notice, and we are unaware we are leaving these traces of our DNA behind.

These departing cells are constantly being created in the lower layers of the epidermis before moving to the surface where they harden and fall off. This process of growing, moving, and shedding takes about four weeks.

SCHEDULE B

Skin Regeneration

Since skin is regularly exposed, it requires frequent cell regeneration. When you get a cut or scrape, skin cells divide and multiply, replacing the skin you have lost. Even without injury, skin cells routinely die and fall off. You lose 30,000 to 40,000 dead skin cells each minute, which is about 50 million cells every day.[68]

[68] https://sciencing.com/life-span-skin-cells-5114345.html.

Skin Regeneration After Wounds.

The process is more obvious when skin is lost due to a cut or other injury. While regrowth is similar to routine human cell regeneration, it has some extra steps.

First, collagen spreads to the wound area to create a framework that will support the new skin. Then, a network of blood vessels migrates to the area, followed by skin and nerve cells. Finally, the hair pigment, oil and sweat glands may regenerate.

If the wound is too deep, it may be missing some of these components and may not grow back properly; infection can slow the process. Even under the best circumstances, the new tissue produced often varies slightly from the original and results in a scar.

Your skin's regenerative capacity is critical given its role in serving as a protective barrier between your internal organs and an often hostile outside world.[69]

[69] https://sciencing.com/life-span-skin-cells-5114345.html.

The Initial Response when Something Happens to Disrupt the Integrity of Your Skin.

When something happens to disrupt the integrity of your skin to the extent that it has to regenerate, your body's immediate response is inflammation. White-blood cells leak out of local blood vessels into the wound, which could be a scrape, cut or burn. Next, various immune cells—including T-cells, Langerhans cells and mast cells—release chemicals called chemokines and cytokines. These substances draw other cells, such as macrophages, to the area. The result of this cascade is the release of nitric oxide and other substances that drive the initial stages of angiogenesis, which is the creation of new blood vessels to replace any that were damaged in the precipitating incident.[70]

[70] https://sciencing.com/life-span-skin-cells-5114345.html.

1. Regeneration of the Epidermis.

Repair of damage to the epidermis starts with the deepest part of the epidermis—the stratum basale. The first stage of regeneration involves proliferation of the cells of the stratum basale itself. Once this is finished, all that's required is for the cells of this layer to continue to divide and migrate upward to fill whatever space remains above. In the case or more superficial cuts, bleeding is absent and the process merely begins with the proliferation of cells of the intact stratum basale.[71]

[71] https://sciencing.com/life-span-skin-cells-5114345.html.

2. Regeneration of the Dermis.

Injuries that penetrate through the epidermis all the way to the dermis set in motion a process distinct from epidermal regeneration. The most important cells in this process are called fibroblasts. These are highly mobile cells, so they can move from the healthy portion of the dermis at the edges of the wound into its interior. Here, they secrete matrix fibers—chiefly collagen and elastin—that form the substance of the regenerating dermis. Meanwhile, macrophages act as scavengers, crawling about and engulfing scab material and anything else that constitutes waste.[72]

[72] https://sciencing.com/life-span-skin-cells-5114345.html.

SCHEDULE C

Fingernails and Toenails

Nails are made up of a translucent protein known as keratin. Our hair and skin are also made up of this protein. Squamous cells at the base of the nailbed multiply, forming layers which harden. This growth process is known as keratinization.

The hardened keratin layers are primarily useful for protecting the sensitive tissues at the tips of our fingers and toes. This helps to prevent injuries like scrapes and cuts which may occur while using our fingers and toes. The tissues at the tips (or pads) of our fingers and toes also contains sensitive nerve endings. These enable the fingers and toes to process sensations like 'touch'. The nail acts as the vehicle for sensory input when contact is made between these portions of the body and other sources. Nails also provide support to these tissues. Without fingernails, we would struggle to be able to grasp or pick up objects or even have a good scratch.

The structure of nails consists of 6 key components, each with a function of their own. Any disruption or problem with these components can influence both healthy function and the appearance of our nails.

1. Germinal Matrix (Nail Root)

This is where growth of the nail takes place—up to 90% of the nail is formed in the germinal matrix. This portion is effectively the root of the nail which is located just below the skin beneath the nail.

2. Sterile Matrix (Nail Bed)

Beneath the nail plate is the nail bed which consists of a dorsal roof, (topside of the formed nail) ventral floor (just beneath the formed nail) and capillaries (blood vessels) that provide blood flow. This is what gives the nail plate a slightly pink appearance.

The nail bed also consists of nerves and melanocytes which contribute to the production of melanin (the pigment that gives human skin, hair and skin their color). The dorsal roof houses the cells that contribute to healthy shine of the nail. The nail bed extends from the edge of the root to the hyponychium (near the tip of fingers and toes).

This region is susceptible to environmental contamination, and thus a 'plug' of keratin (containing polymorphonuclear leukocytes and lymphocytes, types of white blood cells that play a role in our immunity) serve as a barrier for protection.

3. Nail Plate (Body of the Nail)

This is the most visible portion of the nail—it's the bit that gets shaped and decorated. The point at which the nail plate seals with the nail bed near the tip of the finger or toe unit (also known as the distal or free edge—i.e. the skin portion at the tip) is referred to as the hyponychium. This also creates a waterproof barrier. Grooves along the length of the underside of the nail plate help to anchor it to the nail bed.

4. Lunula

At the base of each nail plate is a white/pale crescent (arc) shape known as a lunula. The paler color is attributed to nail cell nuclei in the germinal matrix. There are no cell nuclei in the surrounding portions—hence the remainder of the nail has a more translucent appearance.

5. Nail Folds—Lateral and Proximal (Known as the Paronychium)

On either side of the nail plate and at the base, folds, or skin grooves (or overlaps of skin) help to hold the nail plate in place.

6. Eponychium (Cuticle)

A flap of thin tissue at the base of and overlapping the nail plate is more commonly referred to as the cuticle. This helps to fuse together the finger/toe structure and the nail plate, also providing a waterproof barrier.

Fingernails can grow up to 3 times quicker than toenails. On average fingernails grow approximately 3 mm per month compared to toenails which grow 1 mm every 4 weeks. From the root of the nail to the edge of each finger, it can take around 6 months for growth to take place. For toenails, this growth process can take between 12 and 18 months. Growth of our nails is constant too, even if it tends to slow down as we age.

SCHEDULE D

Selected Skin Conditions and Diseases

The 10 most prevalent skin conditions and diseases are:

1. Acne (Acne Vulgaris).

Over 80 percent of people all over the world developing acne at some point in their lives. It is the most common skin disorder in the United States, and by far the most common skin disorder. Acne is caused by blocked hair follicles and oil (sebaceous) glands of the skin, often triggered by hormonal changes. The term acne refers to not only pimples on the face, but blackheads, cysts, and nodules as well. Some people get acne on other parts of their body too, such as the back and chest.

2. Rosacea.

Rosacea is a chronic swelling of the face, with skin redness or flushing, particularly on the cheeks or T-Zone. It is very common and is often mistaken for acne when it is in fact rosacea. In America, it affects just under 15% of the population, and is most common in women over 30, but men can be affected too. The percentage is thought to be much higher though, as it is often misdiagnosed. Left untreated it can cause skin hardness in the affected areas such as the nose and cheeks. Problems with the immune system, vein problems and/or environmental issues can cause the condition.

3. Eczema (Atopic Dermatitis).

Atopic dermatitis or eczema often starts in childhood and disappears, but is sometimes retained in adulthood. Symptoms include patches of dry, itchy skin that are often rough or raised, different in color or thicker. Typically, these patches occur on the face, near the scalp, inside the elbows, behind the knees and on the hands and feet. One of the factors causing this skin irritation is genetics. It is not allergy-related. There are a few types of eczema, each with their own very specific symptoms. There is no cure, but a factor often causing flare-ups is stress.

4. Shingles (Herpes Zoster).

Shingles virus (herpes zoster) results in a red, blistered rash that may wrap around your torso or appear anywhere on your body. A fever, fatigue and headache may occur, too. Shingles is caused by the same virus that causes chickenpox—the varicella-zoster virus. If you have had chickenpox, you are at risk for shingles as the chickenpox virus lies dormant (not active) in your nervous system for years.

5. Hives (Urticaria).

Hives are the familiar welts (raised, red, itchy areas) that can occur on the skin. Common causes of hives include medication, food, and bug bites or stings.

6. Sunburn.

Sunburns occur when there is too much exposure to ultraviolet (UV) light from the sun or sunlamps. The skin turns red, painful, hot to the touch, and may even peel away. It is hard to know how much time is safe in the sun, though, even with sunscreen protection. Repeated sunburns, especially as a child, can boost the risk for skin cancer later in life. Usually sunscreen needs to be reapplied every 2 hours, but you may just need to stay out of the sun, too.

7. Contact Dermatitis.

Most of us have had contact dermatitis-when we touch something that evolves into a skin reaction. Contact dermatitis is a type of eczema, and may come from plants (poison ivy, sumac, oak), jewelry, latex gloves, and irritants like bleach or soaps.

8. Diaper Rash.

A wet or soiled diaper left on too long can lead to red bumps and rash in the diaper area, the buttocks, genitals, and skin folds. Urine and stool can break down skin, and chemicals in a disposable diaper can dissolve out and irritate the skin. Candida (yeast) or bacteria can also take advantage of the inflamed, broken, skin and complicate the rash.

9. Athlete's Foot (Tinea Pedis).

It is an unfortunate fact, but human feet are prone to fungal infections. Athlete's foot can lead to extreme itching, redness, and cracked skin on the feet and in between the toes. A type of fungi called dermatophytes are commonly found in warm, moist areas like pool decks, shower stalls, and locker rooms.

10. Basal Cell Carcinoma.

Basal cell carcinoma (BCC) is the most common type of skin cancer in the United States. BCC grows in the upper basal cells of your skin but rarely spreads and is curable. You may be prone to BCCs if you spend lots of time in the sun or use a tanning bed frequently. Growths commonly occur on the head, ears, nose, and neck. They can look shiny, red, and scaly, or like an open sore.

Other selected skin conditions and diseases include:

1. Acral Lentiginous Melanoma.

Acral lentiginous melanoma is a type of melanoma arising on the palms or soles. It is a form of melanoma characterized by its site of origin: palm, sole, or beneath the nail (subungual melanoma). It is more common on feet than on hands. It can arise de novo in normal-appearing skin, or it can develop within an existing melanocytic naevus (mole).

What It Looks Like. It starts as a slowly-enlarging flat patch of discolored skin on palm, soles or fingers and toes. At first, the malignant cells remain within the tissue of origin, the epidermis—the in situ phase of melanoma, which can persist for months or years.

Acral lentiginous melanoma becomes invasive when the melanoma cells cross the basement membrane of the epidermis, and malignant cells enter the dermis. A rapidly-growing nodular melanoma can also arise within acral lentiginous melanoma and proliferate more deeply within the skin.

Acral lentiginous melanoma is relatively rare compared to other types of melanoma. There is no connection with the color of skin (skin phototype), and it occurs at equal rates in white, brown or black skin. Acral lentiginous melanoma accounts for 29-72% of melanoma in dark-skinned individuals but less than 1% of melanoma in fair-skinned people, as they are prone to more common sun-induced types of melanoma such as superficial spreading melanoma and lentigo maligna melanoma.

Acral lentiginous melanoma is equally common in males and females. The majority arise in people over the age of 40.

The cause or causes of acral lentiginous melanoma are unknown. It is not related to sun exposure.

2. Capillaritis.

Capillaritis is a harmless skin condition in which there are reddish-brown patches caused by leaky capillaries. It is also known as pigmented purpura.

Capillaritis can affect anyone, but is uncommon in children.

It usually affects otherwise healthy people.

Occasionally capillaritis arises as a reaction to a medication; many different drugs have been occasionally associated with capillaritis including meprobamate, carbamazepine and carbromal.

In others a food additive or a viral infection may be responsible.

Capillaritis may also develop after exercise.

The clinical features of capillaritis. Capillaritis is classified according to its appearance. It is characterized by tiny red and brown dots, described as cayenne pepper spots. These may be scattered over a body region or group together to form a flat red patch, which becomes brown and then slowly fades away over weeks to months. The clinical descriptions are named after the dermatologist who first described them.

3. Chilblains.

Chilblains are tender and/or itchy bumps on acral sites following exposure to damp, cold, non-freezing conditions causing a localized form of vasculitis. Chilblains are also called pernio or perniosis.

Chilblains can affect all age groups, but is most common in young to middle-aged adults, with a female predominance. Childhood chilblains are well-described but appear to be uncommon. Primary chilblains are unusual in the elderly and an underlying cause should be looked for.

Chilblains are seen in temperate climates rather than in countries with extreme cold where the air is often dry, and appropriate clothing and living conditions minimize the risk. Late winter and early spring, when it is wet and temperatures are above freezing, are the peak seasons for chilblains.

During the COVID-19 pandemic, many cases of chilblain-like changes on the toes ('COVID-toes') have been reported as a late manifestation in children and young adults after a mild illness suspected of being due to the novel coronavirus SARS-CoV-2; PCR swabs and antibodies for the virus have been mostly (but not always) negative. Many reported patients had no recent exposure to cold, and a robust antiviral interferon response has been postulated to induce changes in the small blood vessels. Histology has been performed on a small number of cases and the changes described have been typical of chilblains, chilblain lupus, or a thrombotic vasculopathy pattern. The association between COVID-19 and chilblains is still being defined. However, the development of chilblain-like lesions in the absence of exposure to damp cold or secondary causes, should be suspected as being related to SARS-COV-2 infection.

Clinical features of chilblains. Chilblains commonly occur on the fingers, toes, and ears (acral sites). However, chilblains can develop on any areas exposed to chronic cold, such as the thighs/hips of horse riders ('equestrian panniculitis'). Chilblains develop several hours after exposure to damp cold and last for more than 24 hours.

Chilblains typically present as:
Itch and/or burning pain.
Localized swelling
Blanchable red/purple discoloration.
Severe chilblains may blister, or become eroded and ulcerated.

4. Chilblain Lupus Erythematosus.

Chilblain lupus erythematosus (LE) is a rare variant of chronic cutaneous LE originally described by Jonathan Hutchinson in 1888.

The term 'chilblain' is derived from Anglo-Saxon terms 'chill' referring to 'cold' and 'blegen', which is a synonym for 'sore'.

Chilblain LE is an under-reported entity that mainly occurs in adults but can occur at any age.

Associations between chilblain LE and anorexia nervosa, intestinal lymphoma, and pregnancy have been described in the literature.

Clinical features of chilblain lupus erythematosus.

Chilblain LE begins as red or dusky purple patches, papules, and plaques that are initiated or exacerbated by exposure to cold and moisture in a cool climate. The lesions are often pruritic and painful.

The common sites involved are the fingers, toes, heels, and soles of the feet. Less frequently, the lesions may be present on the nose, ears, palms, knuckles, elbows, knees, and lower legs.

Other features may include:
Ulceration
Hyperkeratotic fissuring
Depigmentation similar to vitiligo
Raynaud phenomenon.

People living in regions with warmer and drier climates may not develop typical chilblains.

In some circumstances, chilblains may represent lupus pernio with pre-existing LE rather than as chilblain LE. Although the two entities are clinically similar and both are associated with systemic disease (sarcoidosis and systemic lupus erythematosus, respectively), the prognosis and treatment regimens are distinct.

5. Cracked Heel.

A cracked heel is a common foot problem. In most cases the problem is merely a nuisance and unattractive to look at, however, when the cracks or fissures become deep, standing, walking or any pressure placed on the heel can be painful.

Anyone can get a cracked heel. Dry thickened skin (corn and callus) around the rim of the heel is the very first step towards cracking. Increased pressure on the fat pad under the heel causes it to expand sideways, leading to splitting or cracking of the callus.

In severe cases, cracked heels can become infected, and lead to cellulitis. This must be treated with the elevation of the area, debridement of dead tissue, and antibiotics.

Cracked heels are of particular concern for diabetic patients, who may suffer neuropathic damage (loss of feeling, particularly of the feet), as the fissures may lead to diabetic foot ulcers.

Feet should be inspected daily and on the first sign of any cracking, a moisturizing routine 2-3 times a day may be all that is needed to heal the heel. A pumice stone can be rubbed gently against the callus to take away some of the thick hard skin before applying moisturizer.

The fissures may be treated with a liquid, gel, or spray bandage to reduce pain, protect, and allow more rapid healing.

6. Diabetic Foot Ulcer.

Diabetic foot ulcer is a skin sore with full thickness skin loss on the foot due to neuropathic and/or vascular complications in patients with type 1 or type 2 diabetes mellitus.

Diabetic foot ulcer has an annual incidence of 2-6% and affects up to 34% of diabetic patients during their lifetime. Risk factors for developing a diabetic foot ulcer include:
Type 2 diabetes being more common than type 1.
A duration of diabetes of at least 10 years.
Poor diabetic control and high hemoglobin A1c.
Being male.
A past history of diabetic foot ulcer.

Clinical features of diabetic foot ulcer. A diabetic foot ulcer is a skin sore with full thickness skin loss often preceded by a hemorrhagic subepidermal blister. The ulcer typically develops within a callosity on a pressure site, with a circular punched out appearance. It is often painless, leading to a delay in presentation to a health professional. Tissue around the ulcer may become black, and gangrene may develop. Pedal pulses may be absent and reduced sensation can be demonstrated.

The severity of a diabetic foot ulcer can be graded and staged. There are many different classification systems.

Diabetic foot ulcer is particularly prone to secondary infection resulting in:
Wound infection.
Cellulitis.
Osteomyelitis.

The five-year mortality rate has been estimated to be 42%.

7. Vesicular Hand Dermatitis.

Vesicular hand dermatitis is a form of hand eczema characterized by vesicles or bullae (blisters). A similar condition can affect the feet (vesicular foot dermatitis).

The most common variant of vesicular hand dermatitis is also called vesicular endogenous eczema, dyshidrotic eczema, and pompholyx; cheiropompholyx affects the hands and pedopompholyx affects the feet.

Vesicular hand/foot dermatitis most often affects young adults.

It is more common in females than in males.
It is often associated with palmoplantar hyperhidrosis.
There is a personal or family history of atopic eczema in 50%.

Clinical features of vesicular hand/foot dermatitis.
Vesicular hand/foot dermatitis presents as recurrent crops of deep-seated blisters on the palms and soles. They cause intense itch or a burning sensation. The blisters peel off and the skin then appears red, dry and has painful fissures (cracks).

Vesicular hand/foot dermatitis generally gradually subsides and resolves spontaneously. It may recur in hot weather or after a period of stress, and in some patients is recalcitrant.

8. Erythema Multiforme.

Erythema multiforme is a hypersensitivity reaction usually triggered by infections, most commonly herpes simplex virus (HSV). It presents with a skin eruption characterized by a typical target lesion. There may be mucous membrane involvement. It is acute and self-limiting, usually resolving without complications.

Erythema multiforme is divided into major and minor forms and is now regarded as distinct from Stevens-Johnson syndrome (SJS) and toxic epidermal necrolysis.

Erythema multiforme most commonly affects young adults (20-40 years of age), however, all age groups and races can be affected. There is a male predominance.

There is a genetic tendency to erythema multiforme. Certain tissue types are more often found in people with herpes-associated erythema multiforme (HLA-DQw3) and recurrent erythema multiforme (HLA-B15, -B35, -A33, -DR53, -DQB1*0301).

Infections are probably associated with at least 90% of cases of erythema multiforme.

The single most common trigger for developing erythema multiforme is herpes simplex virus (HSV) infection, usually herpes labialis (cold sore on the lip) and less often genital herpes. HSV type 1 is more commonly associated than type 2. The herpes infection usually precedes the skin eruption by 3-14 days.

*Mycoplasma pneumoniae* (a lung infection caused by the bacteria *Mycoplasma pneumoniae*) is the next most common trigger.

Many different virus infections have been reported to trigger erythema multiforme including:
Parapoxvirus (orf and milkers' nodules)
Herpes varicella-zoster (chickenpox, shingles)
Adenovirus
Hepatitis viruses
Human immunodeficiency virus (HIV)
Cytomegalovirus
Viral vaccines Dermatophyte fungal infections (tinea) have also been reported in association with erythema multiforme.

Clinical features of erythema multiforme. Skin lesions-Typically in erythema multiforme, few to hundreds of skin lesions erupt within a 24-hour period. The lesions are first seen on the backs of hands and/or tops of feet and then spread down the limbs towards the trunk. The upper limbs are more commonly affected than the lower. Palms and soles may be involved. The face, neck and trunk are common sites. Skin lesions are often grouped on elbows and knees. There may be an associated mild itch or burning sensation.

The initial lesions are sharply demarcated, round, red/pink and flat (macules), which become raised (papules/palpable) and gradually enlarge to form plaques (flat raised patches) up to several centimeters in diameter. The center of the papule/plaque darkens in color and develops surface (epidermal) changes such as blistering or crusting. Lesions usually evolve over 72 hours.

The typical target lesion (also called iris lesion) of erythema multiforme has a sharp margin, regular round shape and three concentric color zones:
The center is dusky or dark red with a blister or crust.
Next ring is a paler pink and is raised due to oedema (fluid swelling).
The outermost ring is bright red.
Atypical target lesions show just two zones and/or an indistinct border.

The eruption is polymorphous (many forms), hence the 'multiforme' in the name. Lesions may be at various stages of development with both typical and atypical targets present at the same time. A full skin examination may be required to find typical targets, as these may be few in number.

Lesions show the Köbner (isomorphic) phenomenon, meaning they can develop at sites of preceding (but not concurrent or subsequent) skin trauma.

There is no associated swelling of face, hands, or feet, despite these being common sites of rash distribution. However, the lips are often swollen, especially in erythema multiforme major.

Mucous membrane involvement-Mucosal lesions, if present, typically develop a few days after the skin rash begins. In erythema multiforme minor, mucous membrane involvement is absent or mild. Mucosal changes, if present, consist initially of redness of the lips and inside the cheek. Sometimes blisters develop and quickly break to form erosions and ulcers.

Mucosal lesions consist of swelling and redness with blister formation. The blisters break quickly to leave large, shallow, irregular shaped, painful ulcers that are covered by a whitish pseudo membrane. Typically the lips are swollen with hemorrhagic crusts.

9. Keratolysis Exfoliative.

Keratolysis exfoliativa is a common skin condition in which there is focal peeling of the palms and less often the soles. It is also known as exfoliative keratolysis, dyshidrosis lamellosa sicca, and focal palmar peeling.

Keratolysis exfoliativa generally presents in young active adults. Some individuals have a family history of the disorder.

Microscopy reveals cleavage within the outside horny layer of skin, the stratum corneum.

Clinical features of keratolysis exfoliativa. Keratolysis exfoliativa is more common during the summer months in about 50% of affected individuals. It may be more common in those with sweaty palms due to localized hyperhidrosis.

The first sign of keratolysis exfoliativa is one or more superficial air-filled blisters on the fingers or palms. The blisters burst to leave expanding collarettes of scale and circular or oval, tender, erythematous peeled areas. These peeled areas lack a normal barrier function and may become dry and cracked. However, they are not generally itchy.

Sometimes on the ends of the fingers, the split in the skin is deeper, in which case the skin feels hard and numb and takes longer to peel off. There can be multiple layers of peeling skin (lamellae).

Eventually normal skin forms, but frequently exfoliative keratolysis recurs within a few weeks.

10. Fungal Skin Infections.

There are numerous types of fungal skin infections.

Fungal infections of the skin are also known as 'mycoses'. They are common and generally mild. However, in very sick or otherwise immune suppressed people, fungi can sometimes cause severe disease.

Fungi are parasites or saprophytes and live off living or dead organic matter.

Mycologists identify and classify fungi according to their appearance by microscopy and in culture, and by the method of reproduction, which may be sexual or asexual.

Growing fungi have branched filaments called hyphae, which make up the mycelium (like branches are part of a tree). Some fungi are compartmented by cross-walls (called septae).

Arthrospores are made up of fragments of the hyphae, breaking off at the septae. Asexual spores (conidia) form on conidiophores. The sexual reproductive phase of many fungi is unknown; these are 'fungi imperfecta' and include those which infect humans.

Yeasts form a subtype of fungus characterized by clusters of round or oval cells. These bud out similar cells from their surface to divide and propagate. In some circumstances, they form a chain of cells called a pseudomycelium.

Superficial fungal infections. These affect the outer layers of the skin, the nails and hair. The main groups of fungi causing superficial fungal infections are:
Dermatophytes (tinea)
Yeasts: Candida, including non-albicans candida species, *Malassezia, Piedra*
Molds.

Subcutaneous fungal infections. These involve the deeper layers of the skin (the dermis, subcutaneous tissue and even bone). The causative organisms live in the soil on rotting vegetation. They can get pricked into the skin as a result of an injury but usually stay localized at the site of implantation. Deeper skin infections include:

Mycetoma

Chromoblastomycosis.

Systemic fungal infections. Systemic mycoses may result from breathing in the spores of fungi, which live in the soil or rotting vegetation, or present as an opportunistic disease in immunocompromised individuals.

There are many other types of fungal infections not listed here.

Fungal infections can range from mild to life-threatening. Some fungal infections are mild skin rashes, but others can be deadly, like fungal pneumonia. Because of this, it is important to obtain treatment as soon as possible to try to avoid serious infection.

Fungal infections can look like bacterial or viral infections.

11. Gout.

Gout is a common disorder, which affects around 1% of the population. It is caused by excess uric acid, which exists as ionized urate in the blood. Saturated plasma urate (blood levels above 0.42 mmol/L) may slowly form monosodium urate (MSU) crystals that are deposited in the joints, kidneys, and soft tissues, eventually resulting in arthritis, kidney damage, and lumps under the skin respectively.

In healthy individuals, uric acid/urate is formed after eating certain high-protein foods. Usually most of the uric acid is then excreted by the kidneys in the urine. Excess urate in the blood can result from:

A diet that is high in animal-based protein, especially meat and seafood.

Moderate to high alcohol intake, especially of beer.

High intake of fructose, a sugar found in sugar-sweetened soft drinks and fruit juices (apples and oranges).

Being overweight—gout is associated with the metabolic syndrome.

Some medications, including diuretics, low-dose aspirin and ciclosporin.

Kidney disease can reduce urinary excretion of uric acid.

Overproduction of uric acid can occur in disorders that cause high cell turnover, such as some myeloproliferative disorders (excessive numbers of cells produced by the bone marrow) and some types of anemia (hemolytic anemia and pernicious anemia).

Clinical features of gout. In most cases, the first attack of gout presents with extreme pain and swelling in a single joint, often the big toe (podagra). The pain begins abruptly and the joint is red, hot, and extremely tender. Occasionally the first attack of gout affects multiple joints simultaneously. Patients may have a fever, particularly if many joints are involved. Untreated attacks of gout usually last 7-10 days, following which the patient may be symptom-free until the next attack.

12. Granuloma Annulare.

Granuloma annulare (GA) is a common inflammatory skin condition typified clinically by annular, smooth, discolored papules and plaques, and necrobiotic granulomas on histology. Granuloma annulare is more correctly known as necrobiotic papulosis.

Granuloma annulare is seen most commonly on the skin of children, teenagers, or young adults. The generalized form is more likely to be found in older adults (mean age 50 years). There is a female predominance of 2:1 over males.

Clinical features of granuloma annulare. Granuloma annulare can occur on any site of the body and is occasionally widespread. It only affects the skin. Granuloma annulare may cause no symptoms, but affected areas are often tender when knocked. The plaques tend to slowly change shape, size, and position.

Localized granuloma annulare. The localized form is the most common type of granuloma annulare in general, and specifically in children. One or more skin colored or red bumps form rings in the skin over joints, particularly the knuckles. The surface is smooth and the center of each ring is often a little depressed. Localized granuloma annulare usually affects the fingers or the backs of both hands, but is also common on top of the foot or ankle, and over one or both elbows. Annular rings may be solitary or multiple, and grow outwards maintaining the ring shape before eventually clearing.

Generalized disseminated granuloma annulare. Generalized granuloma annulare usually presents in adults, as widespread skin-colored, pinkish, or slightly mauve-colored patches. The disseminated type is composed of small papules, usually arranged symmetrically in poorly-defined rings 10 cm or more in diameter. They are often found around the skin folds of the trunk (armpits, groin). Itch is common. This is the commonest form associated with HIV.

Subcutaneous granuloma annulare. Subcutaneous granuloma annulare is an uncommon form seen mainly in children. It presents as rubbery lumps (nodules) on scalp margins, fingertips, and shins. Subcutaneous granuloma annulare is also called pseudo-rheumatoid nodules because the subcutaneous lesions look rather like rheumatoid nodules; however, they do not arise in association with rheumatoid arthritis.

Perforating granuloma annulare. Perforating granuloma annulare presents as yellowish plaques or papules on which a crust forms due to the elimination of damaged collagen through the epidermis. Perforating granuloma annulare is usually localized to the hands, but plaques may occasionally arise on any body site, especially within scars. Dermoscopy helps to confirm the presence of perforations in small papules within otherwise typical plaques of granuloma annulare. Perforating lesions are frequently itchy or tender. Perforating granuloma annulare is uncommon except in ethnic Hawaiians and in association with HIV. All age groups can be affected.

13. Hand Foot and Mouth Disease.

Hand foot and mouth disease (HFM), also called enteroviral vesicular stomatitis, is a common mild and short-lasting viral infection most often affecting young children. It is characterized by blisters on the hands, feet and in the mouth. The infection may rarely affect adults.

HFM most often infects children under the age of 10, and most are under 5 years of age (95%). It can uncommonly affect adults and tends to be more severe in the elderly, immunocompromised, and pregnant women.

Hand foot and mouth disease is very infectious, so several members of the family or a school class may be affected. Epidemics are most common during the late summer or autumn months.

Clinical Features of Hand, Foot, and Mouth Disease.

Lesions on the dorsal and palmar surfaces of the hands and feet. The progression is from flat pink patches to small, elongated greyish blisters, and, within a week, these peel off leaving no scars.

Small vesicles and ulcers in and around the mouth, palate, and pharynx. These are sometimes painful, so the child eats little and frets.

Red macules and papules on the buttocks and sometimes on the arms. Lesions can also occur on the genitalia.

Atypical hand foot and mouth disease results in a more widespread rash. Features may include:
Red, crusted papules.
No blisters or very large ones*
Targetoid lesions
Involvement of unusual sites such as the ear*
In children with atopic dermatitis, lesions may select skin affected by eczema (eczema coxsackium).

Flat pink patches on the dorsal and palmar surfaces of the hands and feet are soon followed by small elongated greyish blisters. These resolve by peeling off within a week, without leaving scars.

Usually, there are also a few small oral vesicles and ulcers. These are sometimes painful, so the child eats little and frets. There may be a few on the skin around the mouth. In young children, a red rash may develop on the buttocks and sometimes on the arms.

As in the vast majority of cases, hand foot and mouth disease is a mild illness, there is no need to keep children from school once they are well enough to attend.

The blisters remain infective until they have dried up, which is usually within a few days.

14. Idiopathic Plantar Hidradenitis.

Idiopathic plantar hidradenitis is an uncommon condition in which there are tender, red lumps on the soles of the feet, and less often, on the palms. It has also been called palmoplantar eccrine hidradenitis and painful plantar erythema.

Idiopathic plantar hidradenitis mainly affects children and young adults, but it may affect anyone.
There is a tendency for the condition to appear in the spring and autumn.
It is associated with hot, humid conditions.
Many affected individuals complain of excessively sweaty feet.

Clinical features of idiopathic plantar hidradenitis. Idiopathic plantar hidradenitis is characterized painful red nodules and plaques on the soles and insteps of the feet, and less often, on the palms of the hands. The surface of the skin is unaffected. Walking may be uncomfortable. It is sometimes associated with fever.

The inflammatory reaction clears up spontaneously within 4 weeks. It may recur.

15. Juvenile Plantar Dermatosis.

Juvenile plantar dermatosis is a common and chronic, dry-skin condition of the feet that mainly affects pre-adolescent children.

Juvenile plantar dermatosis is also known as atopic winter feet and forefoot dermatitis.

It commonly affects children between the age of 3 and 14 years, with an average age of 8. It occurs slightly more frequent in boys than girls. Juvenile plantar dermatosis is rarely seen in adults.

Clinical features of juvenile plantar dermatosis. Juvenile plantar dermatosis involves the weight-bearing areas of the soles of the feet presenting as itchy or sore, shiny, red skin with a glazed appearance and loss of the epidermal ridge pattern.
It usually affects both feet symmetrically.
Painful fissures, cracking, and scaling occur.
The plantar aspect of the great toes (ball of the big toes) is the commonest site of involvement and is the usual initial site.
Common involvement of the ball of the foot (forefoot) and in some cases the heel; toe-webs and instep are usually spared, helping to distinguish this from tinea pedis.
It can rarely affect the palms and fingertips.

The most common complication of juvenile plantar dermatosis is painful cracks and fissures. These may take many weeks or months to heal. Juvenile plantar dermatosis usually clears spontaneously in adolescence, but can persist into adult life.

16. Keratolytic Winter Erythema.

Keratolytic winter erythema is a rare inherited skin disorder characterized by recurrent palmoplantar erythema and peeling that is often worse in winter months. It is also known as Oudtshoorn disease and erythrokeratolysis hiemalis.

Keratolytic winter erythema was first described in 1977 by dermatologists in South Africa who observed a skin condition prevalent in families in the Oudtshoorn area of Western Cape.

The prevalence of keratolytic winter erythema is estimated at 1 in 7,200 white Afrikaans speakers. It is inherited in a monogenic autosomal dominant pattern with high penetrance but variable expressivity. It is usually diagnosed in childhood or early adult life.

Clinical features of keratolytic winter erythema. Keratolytic winter erythema usually presents between infancy and early adulthood, and it continues with an intermittent and recurrent pattern. It ranges in severity with cyclical skin peeling and underlying erythema affecting the palms of the hands and the soles of the feet.
A flare begins with the erythema. This may be annular and involve the webbed spaces of the fingers and toes or the entire palm or sole. The erythema can be transgradient, spreading to the top of the hands and feet.
Erythema is followed by painless superficial dry blisters or opaque-appearing skin that peels centrifugally.
Each patch expands over 4-6 weeks before healing.
The erythema retains the papillary ridge pattern of the fingerprints.
Palmoplantar sweating may lead to a pungent odor and increased peeling.

Some patients with keratolytic winter erythema also develop annular erythema on the limbs, buttocks, or trunk; there has been one reported case of facial involvement.

17. Melanoma of Nail Unit.

Melanoma of the nail unit is usually a variant of acral lentiginous melanoma (melanoma arising on the palms of the hands and soles of the feet). Other types of melanoma rarely arising under the nails are nodular melanoma and desmoplastic melanoma.

Melanoma of the nail unit usually affects either a thumbnail or great toenail, but any finger or toenail may be involved. The term includes:
Subungual melanoma (melanoma originating from the nail matrix)
Ungual melanoma (melanoma originating from under the nail plate).
Periungual melanoma (melanoma originating from the skin beside the nail plate)

Melanoma of the nail unit is rare, accounting for only about 1% melanoma in white-skinned individuals. It arises in people of all races, whatever their skin color. Although no more common in dark skin than fair skin, it is the most common type of melanoma diagnosed in deeply pigmented individuals. It is most diagnosed between the age of 40 and 70.

Subungual melanoma often starts as a pigmented band visible the length of the nail plate (melanonychia). Over weeks to months, the pigment band:
Becomes wider, especially at its proximal end (cuticle)
Becomes more irregular in pigmentation including light brown, dark brown Extends to involve the skin of the adjacent proximal or lateral nail fold (Hutchinson sign).

May develop a nodule, ulcerate or bleed

May cause thinning, cracking or distortion of the nail plate (nail dystrophy).

However, in up to half of all cases, subungual melanoma is amelanotic (not pigmented). Ungual melanoma can form a nodule under the nail plate, lifting it (onycholysis). It may sometimes look like a wart (verrucous). It is usually painless, but an advanced tumor invading underlying bone may cause severe pain.

A melanocytic naevus of the nail matrix results in a pigmented band (melanonychia). This tends to be narrower than 3 mm (but can be wider) and a uniform brown or dark brown color. Benign pigmentation observed in the cuticle, or proximal nail fold is referred to as pseudo-Hutchinson sign.

Subungual melanoma may be suspected clinically because of a wide (>3 mm) new or changing pigment band in a single nail. The dermatoscopic examination may reveal more details showing pigmented lines of varying color, width and spacing. These lines tend to lose their usual tendency to run parallel to each other along the length of the nail. Ungual melanoma forms a non-pigmented lump under the nail plate, eventually resulting in its destruction.

Algorithms for diagnosis of melanoma of the nail unit.

ABCD criteria for subungual melanoma in situ.

Lee et al. have suggested ABCD nail criteria to diagnose subungual melanoma in situ when a patient presents with longitudinal melanonychia. The diagnosis was confirmed in their 26 patients with subungual melanoma in situ and 28 patients with nail matrix naevi.

A—adult age (age >18 years)

B—brown bands in a brown background

C—color in periungual skin

D—one digit.

ABCDEF guidelines for pigmented nail lesions.

Levit et al. described ABCDEF guidelines to assess pigmented nail lesions.

Dermoscopic clues to differentiate pigmented nail bands.

In the International Dermoscopy Society survey evaluating dermoscopic clues in pigmented nail bands, melanoma cases were significantly associated with [4]:

The width of the pigmented band occupying more than two-thirds of the nail plate Grey and black colors Irregularly pigmented lines Hutchinson sign and micro-Hutchinson sign (skin pigmentation noted on dermoscopy but not on clinical examination)

Nail dystrophy.

Granular pigmentation, a newly defined dermoscopic criterion, was found in 40% of melanomas and only in 3.51% of benign lesions. The dermoscopic feature of any pigmentation in the hyponychia (the distal pulp of the finger under the nail plate) is parallel pigmented lines on the ridges (in contrast to naevi in which the pigmentation affects furrows or may be diffuse).

The 5-year survival rate ranges widely from 16% to 87%, depending on the series, with two larger series in the 51% to 55% range.

A: Age 40-70 years of age; African, Japanese, Chinese, and Native American heritage B: Brown-black band >3 mm with variegated borders C: Change or lack of change in the nail band or nail morphology D: Digit most commonly involved (thumb, big toe, or index finger)

E: Extension of discoloration into the skin surrounding the nail (Hutchinson sign)

F: Family or personal history of melanoma

18. Discoid Eczema.

Discoid eczema is a common type of eczema/dermatitis defined by scattered, well-defined, coin-shaped, and coin-sized plaques of eczema. Discoid eczema is also called nummular dermatitis.

Discoid eczema can affect all age groups. It is slightly more common in older adult males and younger adult females. In males there is an association with chronic alcoholism. Drug-induced discoid eczema can be due to medications that cause skin dryness.

Discoid eczema can occur in association with atopic eczema, eczema craquelé, and secondary eczematization.

Clinical features of discoid eczema. Discoid eczema usually affects the limbs, particularly the legs, but the rash may be widespread. Although often bilateral, the distribution can be asymmetrical especially if related to varicose veins.

There are two clinical forms of discoid eczema:

Exudative acute discoid eczema: oozy papules, blisters, and plaques.

Dry discoid eczema: subacute or chronic erythematous, dry plaques

Individual plaques are well circumscribed, mostly 1-3 cm in diameter, and inflamed. The majority of patches are round or oval. The plaques are usually very itchy. The skin between the patches is usually dry and irritable.

Severe discoid eczema may generalize, with numerous small to large itchy plaques appearing all over the body due to an autoeczematization reaction.

Patches may clear up without leaving a sign. In dark skin, marks may persist for months as dark brown post inflammatory hyperpigmentation or pale post inflammatory hypopigmentation.

In most cases, the appearance of discoid eczema is quite characteristic.

Discoid eczema tends to be a chronic condition that often relapses especially in cold winter months. Many cases do eventually resolve.

19. Palmoplantar Keratoderma.

'Keratoderma' is a term that means marked thickening of the epidermis of the skin.

'Palmoplantar' refers to the skin on the soles of the feet and palms of the hands; these are the areas keratoderma affects most often. Palmoplantar keratoderma is also sometimes known as 'keratosis palmaris et plantaris'.

Classification of keratodermas depends on whether it is inherited or acquired, and the clinical features.

Diffuse keratodermas affect most of the palms and soles.

Focal keratodermas mainly affect pressure areas.

Punctate-type keratoderma results in tiny bumps on the palms and soles.

Most often the abnormal skin involves only the palms and soles (non-transgradient palmoplantar keratoderma) but sometimes it extends on to the top of the hands and feet as well (transgradient).

In some rare syndromic forms of keratoderma other organs in the body may be affected in addition to the skin, and the keratoderma can be a marker of this internal abnormality.

20. Palmoplantar Pustulosis.

Palmoplantar pustulosis is an uncommon chronic pustular condition affecting the palms and soles. It is also called pustulosis palmaris et plantaris. It is related to a common skin condition, psoriasis.

A variant of palmoplantar pustulosis affecting the tips of the digits is called acrodermatitis continua of Hallopeau or acropustulosis.

Clinical features of palmoplantar pustulosis. Palmoplantar pustulosis presents as crops of sterile pustules occurring on one or both hands and feet. They are associated with thickened, scaly, red skin that easily develops painful cracks (fissures).

Palmoplantar pustulosis varies in severity and may persist for many years. The discomfort can be considerable, interfering with work and leisure activities.

Certain manual occupations or occupations involving much walking are inadvisable for affected individuals.

Certain conditions have been reported to occur in patients with palmopustular pustulosis more often than in unaffected patients.
- Chronic plaque psoriasis (10-25% of patients).
- Autoimmune diseases particularly gluten sensitive enteropathy (coeliac disease), thyroid disease and type 1 diabetes.
- Streptococcal tonsillitis.
- Rarely, synovitis-acne-pustulosis-hyperostosis-osteomyelitis (SAPHO) syndrome.

Palmoplantar pustulosis may rarely be provoked by the tumor necrosis factor (TNF)-alpha inhibitors (infliximab, adalimumab, etanercept).

The majority of patients with palmoplantar pustulosis are current smokers and in those that have smoked in the past (65-90%). It is thought that activated nicotine receptors in the sweat glands cause an inflammatory process.

21. Photosensitivity.

Photosensitivity refers to various symptoms, diseases and conditions caused or aggravated by exposure to sunlight.
- A rash due to photosensitivity is a photodermatosis (plural photodermatoses).
- If the rash is eczematous, it is a photodermatitis.
- A chemical or drug that causes photosensitivity is a photosensitizer.
- A phototoxic reaction to a photosensitizer results in an exaggerated sunburn reaction and no immune reaction is involved.
- A photoallergic reaction to a photosensitizer results in photodermatitis and is due to delayed hypersensitivity reaction.
- A photoexacerbated condition describes a flare of an underlying skin disease on exposure to sunlight.

Photosensitivity occurs in males and females of all races and at all ages. Different types of photosensitivity may be prevalent at different times of life. Genetic and environmental factors are involved.

People with very white skin who do not tan on exposure to the sun (Fitzpatrick skin type 1), especially if they also have red hair and blue eyes, are often considered photosensitive, relative to people with darker skin phototypes that tan more easily. These fair skinned individuals do not have a photodermatosis.

Clinical features of photosensitivity. The clinical features depend on the specific photodermatosis.
- Photodermatoses affect areas exposed to sunlight (face, neck, hands) and do not affect areas not exposed to the light (covered at least by underwear), or are less severe in covered areas.
- Sometimes they spare areas that are habitually exposed to the light, eg the face in polymorphic light eruption.
- Sometimes they only affect certain parts of the body, eg juvenile spring eruption is confined to the tops of the ears.
- Photodermatoses may also occur following indoor exposure to artificial sources of UVR (e.g. fluorescent lamps) or visible radiation. Rashes on exposed sites may be due to another cause. For example:
- Facial acne due to follicular occlusion by sebum and keratin
- Contact dermatitis due to makeup applied to the face.
- Airborne contact dermatitis due to plant pollens, such as sesquiterpene lactone
- Clues to photosensitivity include:
- Summer exacerbation; note that many photodermatoses are present year-round
- The sharp cut-off between affected area and skin covered by clothing or jewelry (e.g., watch strap, ring).
- Sparing of folds of upper eyelids
- Sparing of deep furrows on face and neck
- Sparing of skin covered by hair.
- Sparing of skin shadowed by the ears, under the nose and under the chin
- Sparing of the web spaces between the fingers Severe photosensitivity can lead to a person being unable to go outdoors during the day unless completely covered (including face). This leads to social isolation and depression.

Some photodermatoses cause permanent scarring.

22. Pitted Keratolysis.

Pitted keratolysis is a superficial bacterial skin infection typically of the soles of the feet characterized by whitish skin with clusters of punched-out pits, and resulting in smelly feet.

Pitted keratolysis is much more common in males than in females. Occupations at risk include:
- Farmers
- Athletes
- Sailors or fishermen
- Industrial workers
- Military personnel Females offering pedicure and foot care in a spa salon may also be affected by pitted keratolysis.

Signs and symptoms of pitted keratolysis.
- Typically presents as smelly feet (bromhidrosis)
- Usually affects the sole of the foot-forefoot, heel, or both. Palms are rarely infected.
- Results in a whitish skin surface with clusters of multiple, fine punched-out pits.
- Pits often join together (coalesce) to form a larger, crater-like lesion.
- The appearance is more dramatic when the feet are wet.
- A variant of pitted keratolysis presents with diffuse red areas on the soles.
- The pits themselves are usually asymptomatic but may cause soreness or itching when walking.

23. Psoriasis.

Psoriasis is a chronic inflammatory skin condition characterized by clearly defined, red and scaly plaques. It is classified into a number of types.

Psoriasis affects 2-4% of males and females. It can start at any age including childhood, with peaks of onset at 15-25 years and 50-60 years. It tends to persist lifelong, fluctuating in extent and severity. It is particularly common in Caucasians but may affect people of any race. About one-third of patients with psoriasis have family members with psoriasis.

Psoriasis is multifactorial. It is classified as an immune-mediated inflammatory disease (IMID).

Genetic factors are important. An individual's genetic profile influences their type of psoriasis and its response to treatment.

Clinical features of psoriasis. Psoriasis usually presents with symmetrically distributed, red, scaly plaques with well-defined edges. The scale is typically silvery white, except in skin folds where the plaques often appear shiny with a moist peeling surface. The most common sites are scalp, elbows, and knees, but any part of the skin can be involved. The plaques are usually very persistent without treatment.

Itch is mostly mild but may be severe in some patients, leading to scratching and lichenification characterized by thickened leathery skin and increased skin markings. Painful skin cracks or fissures may occur.

When psoriatic plaques clear up, they may leave brown or pale marks that can be expected to fade over several months.

Certain features of psoriasis can be categorized to help determine appropriate investigations and treatment pathways. Overlap may occur.
- Early age of onset <35 years (75%) vs late age of onset >50 years
- Acute e.g. guttate psoriasis vs chronic plaque psoriasis
- Localized e.g., scalp, palmoplantar psoriasis vs generalized psoriasis.
- Small plaques <3 cm vs large plaques >3 cm
- Thin plaques vs thick plaques
- Nail involvement vs no nail involvement
- Clinical features vary in differing types of skin.

Plaque psoriasis is the most common form of psoriasis in all racial groups. Non-Caucasians tend to have more extensive skin involvement than Caucasians. Asian populations are reported to have the highest percentage of body surface area involvement. In skin of color the plaques are typically thicker with more pronounced silver scale and itch. The pinkness of early patches may be more difficult to appreciate resulting in a low PASI assessment. The thick plaques may appear violet or dark in color. Plaque psoriasis commonly resolves to leave hyperpigmentation or hypopigmentation in skin of color, which further impacts quality of life even after disease clearance.

Other types of psoriasis show variable rates in different skin types. Palmoplantar psoriasis is reported to be most common in the Indian population. Non-Caucasians are more likely to present with pustular and erythrodermic psoriasis than Caucasians, whereas flexural psoriasis is said to occur at a lower rate in skin of color.

Patients with psoriasis are more likely than others to have associated health conditions such as are listed here.
- Inflammatory arthritis "psoriatic arthritis" and spondyloarthropathy (in up to 40% of patients with early-onset chronic plaque psoriasis)
- Inflammatory bowel disease (Crohn disease and ulcerative colitis)
- Uveitis (a form of inflammation of the eye)
- Coeliac disease
- Metabolic syndrome: obesity, hypertension, hyperlipidaemia, gout, cardiovascular disease, type 2 diabetes
- Localized palmoplantar pustulosis, generalized pustulosis, and acute generalized exanthematous pustulosis
- Non-alcoholic fatty liver disease The severity of psoriasis is classified as mild in 60% of patients, moderate in 30% and severe in 10%.

24. Tinea Pedis.

Tinea pedis is a foot infection due to a dermatophyte fungus. It is the most common dermatophyte infection and is particularly prevalent in hot, tropical, urban environments.

Interdigital involvement is most commonly seen (this presentation is also known as athlete's foot, although some people use the term for any kind of tinea pedis).

Tinea pedis may be accompanied by tinea cruris, tinea manuum or tinea unguium.

Tinea pedis usually occurs in males and adolescents/young adults, but can also affect females, children, and older people. Infection is usually acquired by direct contact with the causative organism, for example using a shared towel, or by walking barefoot in a public change room.

Clinical features of tinea pedis. Tinea pedis tends to be asymmetrical, and may be unilateral. It usually presents in one of three ways:
- Itchy erosions and/or scales between the toes, especially between 4th and 5th toes
- Scale covering the sole and sides of the feet (hyperkeratotic/moccasin type, usually caused by *T. rubrum*)
- Small to medium-sized blisters, usually affecting the inner aspect of the foot (vesiculobullous type).

It can also uncommonly cause oozing and ulceration between the toes (ulcerative type), or pustules (these are more common in tinea pedis due to *T. interdigitale* than that due to *T. rubrum*).

The diagnosis of tinea pedis can be made clinically in most cases, based on the characteristic clinical features. Other typical sites, such as toenails, groin, and palms of the hands, should be examined for fungal infection, which may support a diagnosis of tinea pedis.

25. Viral Wart.

A viral wart is a very common benign lesion caused by infection with human papillomavirus (HPV). Viral warts can be classified by site as being cutaneous or mucosal as the HPV types are quite distinct. A cutaneous wart is also called a verruca or papilloma, and warty-looking lesions of any cause may be described as verrucous or papillomatous.

Warts are particularly common in:
- School-aged children, however they may occur at any age.
- Dermatitis, due to a defective skin barrier.
- People with drug-induced immunosuppression such as with long-term azathioprine or ciclosporin use, or have human immunodeficiency virus (HIV) infection.

Clinical features of viral warts. Cutaneous viral warts have a hard, keratinous surface. Tiny red or black dots visible in the wart are papillary capillaries.

Common wart. Common warts (verruca vulgaris) present as cauliflower-like papules with a rough, papillomatous and hyperkeratotic surface ranging in size from 1 mm to 1 cm or more. They may be solitary or multiple. Common warts are found most often on the knees, backs of fingers or toes, and around the nails (periungual).

Plantar wart. Plantar warts (verruca plantaris) include tender inwardly growing myrmecia on the sole caused by HPV 1, and clusters of superficial less painful mosaic warts due to HPV 2. Myrmecial warts are typically tender with lateral and direct pressure, are surrounded by yellow hyperkeratotic callus-like skin showing accentuated skin markings, but with discontinuation of the skin lines through the actual wart.

Plantar epidermoid cysts. Plantar epidermoid cysts are associated with HPV 60 infection of the eccrine ducts.

Plane wart. Plane warts are typically multiple small flat-topped skin-colored papules located most commonly on the face, hands, and shins. On the shins and beard-area of the face the virus is often spread by shaving resulting in numerous warts. Plane warts are mostly caused by HPV types 3 and 10.

Plane warts are typically multiple small flat-topped skin-colored papules located most commonly on the face, hands, and shins. On the shins and beard-area of the face the virus is often spread by shaving resulting in numerous warts. Plane warts are mostly caused by HPV types 3 and 10.

Filiform wart. A filiform wart is a cluster of fine fronds emerging from a narrow pedicle base usually found on the face. They are also described as digitate (finger-like).

Butcher's wart. Butcher's warts are specifically caused by HPV 7 infecting the hands of butchers and others whose occupation involves chronic exposure to a cold moist environment. They clinically resemble common warts and tend to be numerous.

Complications of cutaneous viral warts.

Viral warts are infectious to the patient and others.

Cutaneous warts can have significant psychosocial effects such as teasing at school, embarrassment, permission refused for swimming lessons.

Periungual warts can cause nail dystrophy and destruction.

Pain due to plantar warts (myrmecia type) interferes with walking and sporting activities, causing knee or hip pain.

In epidermodysplasia verruciformis the specific HPV types involved can cause cutaneous squamous cell carcinomas.

Dermoscopy assists visualization of the papillary capillaries of a viral wart, and can distinguish other verrucous lesions such as a seborrhoeic keratosis.

Treatment may not be required in all cases as most warts resolve spontaneously especially in children. Indications for active treatment include:

Immunosuppression

Presence of complications.

Patient preference.

Treatments do not kill the virus, but work by removing virus-containing skin. Persistence with the treatment and patience is essential. Remember HPV infects the basal cell layer of the epidermis so warts recur rapidly if the virus has not been eradicated.

No treatment is universally effective at eradicating viral warts.

In children, even without treatment, 50% of warts disappear within six months, and 90% are gone in 2 years.

Viral warts are more persistent in adults, but they clear up eventually. They are likely to recur in patients that are immunosuppressed, for example, organ transplant recipients. Recurrence is more frequent in tobacco smokers.

Immunity to HPV is likely to be type-specific.

26. Vitiligo.

Vitiligo is an acquired depigmenting disorder of the skin, in which pigment cells (melanocytes) are lost. It presents with well-defined milky-white patches of skin (leukoderma). Vitiligo can be cosmetically very disabling, particularly in people with dark skin.

Vitiligo affects 0.5-1% of the population, and occurs in all races. It may be more common in India than elsewhere, with reports of up to 8.8% of the population affected. In 50% of sufferers, pigment loss begins before the age of 20, and in about 80% it starts before the age of 30 years. In 20%, other family members also have vitiligo. Males and females are equally affected.

Even though most people with vitiligo are in good general health, they face a higher risk of having autoimmune diseases such as diabetes, thyroid disease (in 20% of patients over 20 years with vitiligo), pernicious anemia (B12 deficiency), Addison disease (adrenal gland disease), systemic lupus erythematosus, rheumatoid arthritis, psoriasis, and alopecia areata (round patches of hair loss).

A vitiligo-like leukoderma may occur in patients with metastatic melanoma. It can also be induced by certain drugs, such as immune checkpoint inhibitors (pembrolizumab, nivolumab) and BRAF inhibitors (vemurafenib, dabrafenib) used to treat metastatic melanoma. Vitiligo is also three times more common in hematology patients that have had allogeneic bone marrow and stem-cell transplants, than in the healthy population.

Clinical features of vitiligo. Vitiligo can affect any part of the body. Complete loss of pigment can affect a single patch of skin, or it may affect multiple patches. Small patches or macules are sometimes described as confetti-like.

Common sites are exposed areas (face, neck, eyelids, nostrils, fingertips and toes), body folds (armpits, groin), nipples, navel, lips and genitalia.

Vitiligo also favors sites of injury (cuts, scrapes, acne, thermal burns and sunburn). This is called the Koebner phenomenon.

New-onset vitiligo also sometimes follows emotional stress.

Vitiligo may occasionally start as multiple halo naevi.

Loss of color may also affect the hair on the scalp, eyebrows, eyelashes, and body. White hair is called 'leukotrichia' or 'poliosis'.

The retina at the back of the eye may also be affected. However, the color of the iris does not change.

The color of the edge of the white patch can vary.

It is usually the color of unaffected skin, but sometimes it is hyperpigmented or hypopigmented.

The term trichrome vitiligo is used to describe three shades of skin color. Very rarely, there are four shades of pigment (white, pale brown, dark brown and normal skin).

Occasionally, each patch of vitiligo has an inflamed, red border.

The severity of vitiligo differs with each person. There is no way to predict how much pigment an individual will lose or how fast it will be lost.

Vitiligo appears more evident in patients with naturally dark skin.

Extension of vitiligo can occur over a few months, then it stabilizes.

Some spontaneous repigmentation may occur. Brown spots arise from the hair follicles, and the overall size of the white patch may reduce.

At some time in the future, the vitiligo begins to extend again.

Cycles of pigment loss followed by periods of stability may continue indefinitely.

Light skinned people usually notice the pigment loss during the summer as the contrast between the affected skin and suntanned skin becomes more distinct.

The pigment has occasionally been reported to be lost from the entire skin surface.

It should be noted that the risk of thyroid cancer is higher in patients with vitiligo compared to patients without vitiligo.

In most cases, the severity of vitiligo is not formally assessed. However, clinical photographs may be taken to monitor the condition.

Vitiligo is usually a clinical diagnosis, and no tests are necessary to make the diagnosis. The white patches may be seen more easily under Wood lamp examination (blacklight). Dermoscopy characteristically shows a white glow. Clinical photographs are useful to document the extent of vitiligo for monitoring. Serial digital images may be arranged on follow-up. The extent of vitiligo may be scored according to the body surface area affected by depigmentation.

SCHEDULE E

Skin Abnormalities that are Often Important Factors in the Diagnosis of a Variety of Internal Diseases Your skin can be a window to your health, given that many underlying health conditions-some very serious-first appear as skin problems. For example:

a. Butterfly Rash.

A butterfly rash across the face is a skin condition that often (but not always) is the first sign of lupus, a chronic disease that involves your immune system and can damage any part of your body. Nine out of ten adults with lupus are women. That said, it could be rosacea or contact dermatitis.

b. Velvet Plaques.

This skin condition, formally known as acanthosis nigricans, is a skin pigmentation problem characterized by having dark, velvety, and thick patches of skin usually in the neck and/or armpit. It suggests diabetes, although it could be benign or be caused by obesity. In rare cases acanthosis nigricans occurring in other places, such as the hands or lips, may indicate an internal cancer. It is more common in women and is somewhat rare, with fewer than 200,000 cases per year in the United States.

c. Leg Plaque: Red on Edge, Gold in Center.

This skin condition, formally known as necrobiosis lipoidica diabeticorum, is a chronic skin disease and a distinctive sign of diabetes. It can first appear as a dull, reddish colored patch, but then become shinier with a distinct border. Sometimes the affected skin may crack. Usually there are several spots. It is three times more common in women than men, and usually develops in young and middle-aged adults.

d. Itchy, Violet Bumps on the Wrist.

This skin condition, formally known as lichen planus, is a rash made up of reddish-purple, flat-topped bumps that may itch a lot. The rash usually appears on wrists and ankles, but may be in the mouth or on the lower back, neck, legs, and genitals. There are more than 200,000 cases per year in the United States of this chronic inflammatory condition, and it most commonly affects those of ages 35 to 50. It is more common in women. If the condition is present, one may need to get liver tests, since it could be linked to having hepatitis C.

e. Flesh Colored, Orange-Peel Patches on Back.

Shagreen patches (connective tissue nevus) are flesh-colored lesions on the lower back or nape of the neck. The shagreen patch is an area of thickened, elevated pebbly skin that has the texture of an orange peel. They are oval-shaped and nevoid, skin-colored, or occasionally pigmented, smooth, or crinkled. They often occur with other skin signs: red or brown acne-like bumps spreading across the cheeks and nose; and ash-leaf spots of under-pigmented skin, most often on the trunk, that are oval at one end and pointy at the other. These are signs of a rare genetic disease called tuberous sclerosis that causes benign tumors to grow in the brain and other vital organs.

f. Tripe Palms.

Tripe palms describes a skin condition in which the skin of the palm becomes thick and velvety-white with pronounced folds in the lines of the hand. The skin resembles boiled tripe, and about 90% of cases can be linked to cancer. As such, it is a skin condition with great predictive value. If only the palms are involved it may be lung cancer. If tripe palms is accompanied by acanthosis nigricans, it is more likely stomach cancer.

g. "Wooden" Hands and Feet.

Formally known as nephrogenic systemic fibrosis, this skin condition was first described in 1997 and starts as a brown discoloration and indentation of the lower arms and legs. Very soon, the hands and feet become brown and like wood. Sometimes there is also a small yellow spot in the skin. This skin condition usually occurs in persons with reduced kidney functions. Researchers have found that the dye used during MRI triggers this condition in some people with kidney disease. This skin condition is fairly rare, with fewer than 1,000 cases per year in the United States.

h. Scaly Rash on Buttocks, Red Tongue.

This skin condition, formally known as necrolytic migratory erythema, is a characteristic skin rash that is fairly rare. It appears as a red, scaly rash, sometimes with small erosions of the skin, more often seen in elderly people. It tends to start in the fold of the buttocks or palms but can be elsewhere on the body. A bright red, painful tongue is common. The skin condition usually signals a pancreatic tumor, usually a glucogonoma.

Heart Disease. Heart disease is a group of conditions related to your heart. Some are problems with the muscle itself, the valves, or how it beats, including cardiomyopathy, atrial fibrillation, and heart failure. Others affect your blood vessels, like hardened arteries and strokes.

Your skin can display conditions that may indicate potential heart disease.

a. Yellow-Orange Bumpy Skin Rash Around the Knuckles of Your Fingers and Toes and on your Bottom.

This skin condition may indicate extremely high triglyceride levels, which may play a role in hardening your arteries. High triglyceride numbers are often related to other conditions that put you at risk for heart disease and strokes too.

b. Dark Spot Under Fingernails or Toenails.

If you have not banged or hurt your finger or toe recently, little dots of blood trapped under your nail could point to an infection in the lining of your heart or valves, called endocarditis. You can also get these blood specks when you have diabetes, and people with that condition are two to four times more likely to have heart disease and strokes.

c. Blue or Gray Fingers and Toes.

Blue or gray fingers and toes could be from poor circulation of oxygen-rich blood, often due to a heart defect you were born with or narrowed or blocked blood vessels. A lacy, mottled, purple pattern shows up when bits of built-up cholesterol plaques break off, then get stuck in small blood vessels. You might get bloody splotches just under the skin on the inside of your hands and the soles of your feet when you have endocarditis.

d. Dark, Velvety Skin Patches in Skin Folds and Creases such as Your Neck, Armpits, and Groin.

You may find these thick spots, called acanthosis nigricans, in skin folds and creases such as your neck, armpits, and groin when your body has trouble using the hormone insulin. The patches could have skin tags, too. If you are not being treated for insulin resistance, metabolic syndrome, or type 2 diabetes, you should see a doctor for help controlling your blood sugar and protecting your heart.

Not all skin conditions are a need for potential worry. Most skin conditions do not indicate that anything is seriously wrong. An example of such a skin condition is granuloma annula colored bumps that can be found on the hands and feet. These colored bumps usually go away, and are typically not indicative that anything is wrong with you.

SCHEDULE F

Skin Burns

1. First-Degree Burn.

A first-degree burn is the most common type of burn. Symptoms include dry skin with mild swelling, changes in skin color, pain, itchiness, and sensitivity to the touch. Sometimes blisters and peeling may occur. If touched, the skin may blanch (lighten in color). The epidermis typically remains intact. While first-degree burns may be painful, long-term damage is rare. Also known as 'superficial' burns, common causes include mild sunburn, tipped over hot liquids, hot bathwater, cooking fluids, hot appliances such as a cooker or iron, and friction between skin and hard surfaces such as turf on a sports field, floors, roads, or carpets.

First-degree burns often heal on their own within a week, usually without scarring of the skin. A person may require medical treatment if the burn is over a large area of skin. First degree burns are common, with over 200,000 cases per year in the United States.

2. Second-Degree Burn.

Second-degree burns affect deeper layers in the skin than first-degree burns and can involve intense pain. They affect the epidermis and dermis, with the burn site often appearing swollen and blistered. The area may also look wet, and the blisters can break open, forming a scab-like tissue. Doctors also call them partial-thickness burns.

A second-degree burn is more likely to require medical treatment, depending on its location and depth. Causes of second-degree burns include boiling water, flames from a fire, hot stoves, burning candle wax, steam from an iron, hot iron, sunburn in extreme cases over a large area, and chemical burns.

Many second-degree burns heal within a couple of weeks, although scar tissue can occur.

3. Third-Degree Burn.

This type of burn is the most severe, and requires medical treatment. Nerve and blood vessel damage often leave the burn site looking pale in color or blackened and charred. Despite the severity, third-degree burns are often painless because of damage to the nerve endings. Doctors may call them full-thickness burns.

Causes of third-degree burns include a scalding liquid, flames, an electrical source, contact with a hot object for an extended period, and a chemical source.

Third-degree burns destroy the epidermis and the skin follicles, which means new skin will not grow back. Anyone who has a third-degree burn needs immediate medical attention.

A large proportion of burn injuries, both minor and serious, occur in the home, where eighty percent (80%) of the victims are children in the 1 to 16 age group. Other categories of concern in the home are the elderly and disabled, while in industry, electricians and workers in the chemical, refinery, and catering industries.

Burns over about ten percent (10%) or more of the body area are serious and may produce severe shock. For assessment purposes the area burnt is more significant than the depth of the burn. In addition, on average burned children become shocked more quickly than adults.

The treatment of burns depends on the location and severity of the skin damage. Sunburns and small scalds can usually be treated at home. Deep or widespread burns need immediate medical attention. Some people need treatment at specialized burn centers and monthslong follow-up care.

Blisters are an indication that the body is not happy with the heat it has absorbed. If the blisters rise immediately, it is almost certain the burn is not superficial, and it the blisters take one or two hours or more to appear the burns are more than likely to be superficial.

SCHEDULE G

Skin Punctures: Puncture Wounds and Cuts

Puncture wounds may be small in diameter and not seem serious. A puncture wound does not usually result in excessive bleeding. Typically, these wounds close fairly quickly without any intervention. Puncture wounds, however, may become infected easily because dirt and germs are carried deep into the tissues. Sometimes, infection may be delayed. Foot wounds that happen from punctures with objects found outside have a high risk of infection. Wounds that penetrate through a shoe can be contaminated with sock and shoe particles. Infections with bacteria or spores that can cause tetanus, which affects the nervous system, or long-term bone infections, can also happen. Treatment may be necessary to prevent infection in some wounds.

Common Causes of Puncture Wounds. Common causes of puncture wounds are wood splinters, pins, nails, and glass. Puncture wounds may also be caused by objects such as scissors and knives. Almost any sharp object can potentially cause a puncture wound.

Puncture Wound Symptoms. Puncture wounds usually cause pain and mild bleeding at the site of the puncture. It is usually fairly obvious if a person is cut. However, small pieces of glass may cause puncture wounds that a person may not notice at first.

Infection may cause redness, swelling, pus, or watery discharge from a puncture wound that is not noticed or not treated properly.

When to Seek Medical Care. If the wound will not stop bleeding after 5 minutes of direct pressure or is spurting blood, a doctor should be called or you should go to an Emergency Department.

If the wound was caused by a nail, pen, or pencil, a doctor should be called to see if the person needs immediate care or close follow-up.

If the person is not sure when they had their last tetanus shot, someone should check with the doctor's office. Individuals will need a tetanus shot if it has been more than 10 years since their last shot or if their last tetanus shot was more than 5 years ago, and the wound has been contaminated with dirt. This is done since immunity to tetanus may wane over time.

If the person knows or suspects part of the object remains in the wound, a doctor should be contacted. The individual may need urgent care to detect and remove the object.

When to go to the Hospital. You should seek emergency medical attention in any of the following situations:
- If the wound is in the head, chest, or abdomen, unless it is very small, but it is better to be sure. If there is any concern, see a doctor.
- If there is loss of feeling, numbness, or inability to move an arm or leg below the wound.
- If the wound is more than 24 hours old and the person develops signs of infection, such as redness at the area of the wound, swelling, pus drainage, fever over 100 F (37.3 C), or red streaks coming away from the wound.

If the wound does not stop bleeding after pressure is applied for 5 minutes

If the wound has part of an object remaining in it, such as a pencil tip, nail, or piece of glass or plastic.

If a lot of dirt remains in the wound.

If the wound is gaping or there is white tissue (fatty tissue) or muscle visible.

If the person has a chronic medical condition, such as diabetes, or takes steroids.

If the wound is close to or in an skin.

Puncture Wound Diagnosis. The evaluation of a puncture would is based on a thorough history of what caused the puncture wound and the circumstances surrounding the event. The doctor will ask about the time from injury to evaluation, type of object that caused the injury, an estimate of the depth of penetration, inspection of the object if available, and whether or not footwear was worn if the injury is to the foot.

Patients will be asked about the date of their last tetanus shot.

X-rays may be taken as needed, to look for any possibility of an object left behind in the puncture wound or to assess any damage to the underlying bone. Ultrasound may also be performed.

Gunshot Wounds. Gunshot wounds, particularly entry wounds, are puncture wounds. They are seldom stitched because infection is possible. Exit wounds, on the other hand, are often gaping holes and torn flesh which need to put back together with staples and stitches followed by antibiotic treatment.

Gunshot wounds create blast injury around the hole which is very different from a common laceration. With a laceration what is cut is injured, but what is 0.1 mm on each side is generally okay. With blast injury there will be tissue so disrupted that it will die and become perfect bacterial growth media. If that tissue were sealed up with sutures, it is very likely to get infected and abscess. The risk of infection is high and cosmesis will not be good because there will be gaps in the closure where tissue that looked okay turns out to have been necrotic.

Knife Wounds. Knives cause more disabling injuries than any other type of hand tool. Knives represent an important source of morbidity and mortality to people of all ages.

An estimated 8,250,914 knife-related injuries were treated in U.S. Emergency Departments from 1990 to 2008, averaging 434,259 injuries annually, or 1,190 per day. The injury rate was 1.56 injuries per 1000 U.S. resident population per year. Fingers/thumbs (66%; 5,447,467 of 8,249,410) were injured most often, and lacerations (94%; 7,793,487 of 8,249,553) were the most common type of injury. Pocket/utility knives were associated with injury most often (47%; 1,169,960 of 2,481,994), followed by cooking/kitchen knives (36%; 900,812 of 2,481,994). Children were more likely than adults to be injured while playing with a knife or during horseplay. One percent of patients were admitted to the hospital, and altercation-related stabbings to the trunk accounted for 52% of these admissions.

SCHEDULE G-1

Skin Bruising/Contusions

1. Senior/Elderly Skin Bruises.

Seniors experience physical changes as they age. Fragile skin is a common problem in older adults because skin cells divide more slowly than when they were young, and their skin begins to thin due to aging, sun exposure, and genetics. In the elderly, skin retains less moisture and loses its elasticity. The skin's ability to repair itself diminishes, and wounds are slower to heal. Also, over time, people lose subcutaneous fat, which cushions and protects blood vessels.

Some people, especially women, are more prone to bruising than others.

Easy bruising is common with age, but sometimes can be a sign of a more serious problem.

a. Senile purpura: Common and harmless bruising. Senile purpura, also called actinic purpura, is a type of elderly skin bruising that does not result from serious trauma even though it may look like an injury occurred. After years of sun exposure, small blood vessels (capillaries) near the skin's surface can burst with only minor impact, such as a handshake or light bump, leaving noticeable black-and-blue marks on fragile, elderly skin. The bruises are caused by bleeding under the skin on the arms and hands—though they can occasionally appear elsewhere—and generally take up to three weeks to fade and disappear, as the body reabsorbs the blood.

b. Bruising on legs and arms. Sometimes, elderly skin bruising on arms and legs is caused by medical procedures and everyday assistance. Older adults who require help with activities of daily living (ADLs) tend to have more bruises than those who do not, according to a study on bruising by researchers at the University of California, Irvine. This is because caregivers must touch and lift seniors who need help bathing, dressing, or moving between seated positions, which can bruise elderly skin even when done carefully.

Older adults who need intravenous (IV) procedures and shots may have bruises from minor blood vessel damage when the needle is inserted.

Immobilization is another cause of elderly skin bruising. Like bedsores, bruising often occurs when a bedridden senior's body begins to break down skin tissue after prolonged pressure and inactivity.

c. Unexplained bruising and medical conditions. Unusual amounts of bruising should not be ignored, as this may be a warning sign of an underlying condition. Unusual bruising includes swelling, extremely large contusions, chronic bruising in the same areas of the body, and irregularly shaped bruises that typically mimic the shape of knuckles or fingers. These could be signs of internal bleeding or other serious conditions which should prompt an immediate visit to one's doctor. if significant bruising occurs, in some cases it can reveal serious health issues.

Some prescriptions and over-the-counter medications can cause bruising. Ask your doctor or pharmacist if a new prescription is likely to cause old-age bruising.

Some examples of conditions and medications that can lead to bruising:

Anemia is common in the elderly when their appetites change. Anemia leads to easy bruising.

Large bruises can be a sign of clotting disorders, such as deep vein thrombosis, which can be caused by prolonged sitting or bed rest.

Anticoagulants and blood thinners lower the chances of heart attack and artery blockages that may cause strokes, but they also increase the risk of bruising. Seniors who take medicine for hypertension are more likely to develop bruises on the torso.

Common over-the-counter medications, such as ibuprofen, aspirin, asthma medications, and cortisone, may also increase the chances of bruising.

NSAIDS (nonsteroidal anti-inflammatory drugs such as Motrin and Aleve).

Antidepressants, antibiotics, vitamin E, *Ginkgo biloba*, and fish oil, may also increase the chances of bruising.

Liver disease can lead to easy bruising because the liver is responsible for producing blood-clotting platelets.

Diabetes can be linked to bruising on arms and legs, especially if the contusions take unusually long to heal.

Chemotherapy.

d. Bruising and elder abuse. In some circumstances, elderly skin bruising may be a sign of abuse. Elder abuse is a knowing, intentional, or negligent act by a caregiver or other person that causes serious risk of harm to a vulnerable older adult, according to the National Center on Elder Abuse (NCEA).

Because aging skin bruises easily, increased bruising is generally not a sign of abuse. However, it is important to be observant.

Understanding more about accidental versus intentional elderly skin bruising can help determine whether elder abuse is a concern. The following things should be kept in mind regarding accidental versus intentional bruising:

Ninety percent of accidental bruising is on the extremities, not the neck, trunk, or head.

Inflicted bruises can be large and distinct in shape. Most adults who have been abused have bruises 2 inches or larger, which may show finger marks.

Because older adults—especially those with dementia—can experience severe behavioral changes as they age, elderly skin bruising could come from a partner who never had previous violent tendencies, or bruises may even be self-inflicted.

2. Fair Skin. People who have fair skin often bruise easily.
3. Easy Bruising Which Indicates a More Serious Medical Condition. Easy bruising sometimes indicates a more serious underlying medical condition, such as a blood-clotting problem or a blood disease. Follow-up medical treatment may be indicated if one has:

Frequent, large bruises, especially if your bruises appear on your trunk, back or face, or seem to develop for no known reasons.

Easy bruising and a history of significant bleeding, such as during a surgical procedure.

Suddenly begin bruising, especially if you recently started a new medication.

Have a family history of easy bruising or bleeding.

These signs and symptoms can indicate:

Low levels of the blood components that help it clot after injury (platelets).

Abnormally functioning platelets.

Problems with proteins that help the blood clot.

Bleeding disorders such as hemophilia or Von Willebrand disease.

Vitamin C or K deficiency.

Liver or kidney disease or even cancer.

Other serious causes of bruising include domestic violence or abuse. If one has an unexplainable bruise, particularly in an unusual location such as on the face, it may indicate the possibility of abuse.

4. Six reasons to see a doctor about unexplained bruising
   a. You have systemic symptoms like fever, chills, swollen lymph nodes or unintentional weight loss along with unexplained bruising.
   b. Your bruises look like big purple spots with clear edges, and you are younger than 65. These spots, called purpura, are common in older adults but may be a sign of inflamed blood vessels in younger people.
   c. Your bruises look like tiny dots. These bruises are called petechiae and appear when tiny blood vessels called capillaries break. They are common on the neck and chest after prolonged straining from vomiting or childbirth. They also can appear on the lower legs and may be an early sign of problems with platelets, the blood cells involved in clotting. If you have not had a recent straining event, they may indicate a more serious medical condition.
   d. Your bruises are getting larger with time. The bruise may be a hematoma that could continue to bleed if you take blood thinners or have a bleeding disorder.
   e. You notice a lot more bruises than normal or bruises in unusual places. Bruises on your back, abdomen and upper thighs may be concerning because most people do not frequently bump those body parts. Bleeding into the joints that causes swelling or bruising may be a sign of a bleeding disorder.
   f. Your bruising occurs along with other bleeding. Bruising accompanied by frequent nosebleeds that are hard to stop or blood in the urine or stool should be investigated.

You should consult with a hematologist if you have continued significant bruising larger than one centimeter with no known trauma.

See https://www.aplaceformom.com/caregiver-resources/articles/elderly-bruising; see also https://www.mayoclinic.org/healthy-lifestyle/healthy-aging/in-depth/easy-bruising/art-20045762?msclkid=59d564cabb5311ecaf0a7179fd0e246c; see also https://shine365.marshfieldclinic.org/cancer-care/unexplained-bruising/#:~:text=Six%20reasons%20to%20see%20a%20doctor%20about%20unexplained, bruises%20in%20unusual%20places.%20 . . . %20More%20items . . . %20?msclkid=20d1eadebb5511ec9bbc4332c36b7169; see also https://www.buoyhealth.com/learn/unexplained-bruising?msclkid=652069bdbb5d11ec8a9c8aa4f7f5cle4.

SCHEDULE H

Plastic Surgery and Cosmetic Surgery

1. Plastic Surgery.

Types plastic surgery procedures include, without limitation:

Breast Reconstruction

Burn Repair Surgery

Congenital Defect Repair: Cleft Palate, Extremity Defect Repair

Lower Extremity Reconstruction

Hand Surgery

Scar Revision Surgery

Physicians who become board certified in plastic surgery are required to complete one of two routes of training:
   (i) An integrated residency training that combines three years of general surgery and three years of plastic surgery or;
   (ii) An independent, five-year residency program in general surgery followed by the three-year plastic surgery residency program.

Residency programs in plastic surgery may include cosmetic surgery as a portion of a surgeon's training, but typically do not include training on every cosmetic procedure.

2. Cosmetic Surgery:

Focused on Enhancing Appearance. Types of cosmetic surgery procedures include, without limitation:

Breast Enhancement: Breast Augmentation, Breast Lift, Breast Reduction

Facial Contouring: Rhinoplasty, Chin, or Cheek Enhancement

Facial Rejuvenation: Facelift, Skinlid Lift, Neck Lift, Brow Lift.

Body Contouring: Tummy Tuck, Liposuction, Gynecomastia Treatment

Skin Rejuvenation: Laser Resurfacing, Botox®, Filler Treatments

EXHIBIT I

Total Body Skin Exam

A full body skin exam, or skin cancer screening, is a visual exam that checks the skin for certain unusual marks which may be signs of skin cancer. Birthmarks, moles, and other suspicious spots that have an unusual color, size, shape, or texture are what dermatologists usually pay most attention to during these screenings.

Many skin conditions are easily identified by people who notice something "different" on their skin. Acne, psoriasis, hives, and rosacea, would be examples of conditions that a person might notice. However, moles, sunspots, and other blemishes that appear on the skin are sometimes dismissed or go completely unnoticed. These should be professionally assessed through a full body skin examination performed by a dermatologist.

A full body skin exam identifies suspicious growths or spots that may indicate symptoms of skin cancer. This process is also sometimes called "skin cancer screening" and is essential for detecting and treating skin cancer early on.

Skin cancer is the most common type of cancer in the United States, and it occurs in four forms: actinic keratoses, basal cell carcinoma, squamous cell carcinoma, and melanoma. Basal and squamous cell carcinoma are the most common skin cancers, while melanoma is the deadliest. With early detection through regular skin screenings and treatment, these cancers have a high cure rate.

Full body skin examinations are best conducted by a dermatologist, who is trained to identify these spots or growths. While some general practitioners conduct routine skin exams, a doctor may refer you to a dermatologist who can do a more detailed examination. Dermatologists are also more familiar with disorders that affect the skin, hair, nails, and mucous membranes-so they are best at diagnosing and treating skin cancer, acne, psoriasis, rosacea, eczema, and more.

When dermatologists conduct a complete check-up, they are mostly concerned with signs of skin cancer, which include:

Shiny pink, red, pearly white, or translucent bumps
Painful moles
Skin marks that ooze, bleed, or get crusty
Sores that don't heal
Sores with irregular borders
Changes in an existing spot or mole For signs of melanoma, a dermatologist will look more specifically at the growth. They are trying to find the following "ABCDE" signs:

Asymmetry: The doctor will draw a line through the middle of the growth. If the mole has an odd shape or the halves do not match, it's considered asymmetrical. This is one possible warning sign of skin cancer.

Border: One warning sign of skin cancer is a ragged or scalloped border of a mole, freckle, or spot. Cancer-free growths will usually have smooth, even borders.

Color: If the color of a growth is uneven or multi-colored, then this may indicate skin cancer. Most non-cancerous growths are a single shade of brown.

Diameter: Cancerous growths are frequently larger than the size of a pea or a pencil eraser, while benign marks are typically smaller in diameter.

Evolving: Common, benign growths tend to look the same over time. On the other hand, cancerous growths may change in size, shape, color, or elevation.

When these suspicious growths are identified in a screening, patients usually undergo a test, treatment, and finally a follow-up. The test is usually a biopsy, which is a procedure that removes a tiny sample of the skin. The sample will be examined under a microscope to check for cancer cells. A biopsy can accurately determine if the growth is cancerous as well as the type of cancer.

The appropriate treatment will be prescribed after the biopsy, once your dermatologist determines how aggressive the growth is. Finding and treating the disease early will greatly help in preventing the cancer from spreading.

What To Expect During a Full Body Exam. If you have never had a comprehensive check-up by a dermatologist you can expect the exam to last up to 20 minutes. You may be asked to remove your nail polish, make-up, and anything else covering the skin and nails. You will also be requested to wear your hair loose for the exam.

Your doctor will ask you to remove your clothing and wear an exam gown for the head-to-toe exam. They will check your scalp, ears, toes, fingers, buttocks, and genitals for any signs of skin cancer, and use a special magnifying glass with a light to see the marks clearly.

Who Should Get a Full Body Exam. While everyone should get screened by their doctors, some patients are more at risk than others. Here are some characteristics of patients who should have a dermatologist conduct a regularly recurring skin cancer exam for them:

Patients with a light skin tone.
Patients with skin that burns or freckles easily
Patients with a history of blistering sunburns
Patients with a family history of melanoma.
Patients with a family history of other skin cancers
Patients with a large number of moles.
Patients who have a history of tanning bed use
Patients who are frequently exposed to the sun through leisure or occupational activities.
Patients who are a recipient of an organ transplant Dermatologists are specially trained in detecting skin cancer, the most common form of cancer in the United States. Most skin cancers are highly treatable, especially when they are caught early, so having skin cancer screenings is an important part of your healthcare routine.

Any adult who has never had one should consider scheduling a full-body skin exam to establish a baseline and to discuss whether, or how often, regular skin checks are necessary.

Annual skin exams may be recommended for anyone who:
Has a history of melanoma, other skin cancers or precancerous skin lesions.
Has a first-degree relative who has had melanoma.
Has a large number of moles or a history of atypical moles.
Has a history of tanning bed use.
Has a history of blistering sun burns.
Has a history of significant regular sun exposure through activities such as boating or living in a sunny location, or occupations such as landscaping or construction.

EXHIBIT J

Three Main Types of Skin Biopsies

The three main types of skin biopsies are:
Shave biopsy. A doctor uses a tool similar to a razor to remove a small section of the top layers of skin (epidermis and a portion of the dermis).
Punch biopsy. A doctor uses a circular tool to remove a small core of skin, including deeper layers (epidermis, dermis, and superficial fat).
Excisional biopsy. A doctor uses a small knife (scalpel) to remove an entire lump or an area of abnormal skin, including a portion of normal skin down to or through the fatty layer of skin.

INSERT K

Breast Biopsies and the Tiny Physical Clips Used to Identify the Biopsy Site

Statistically, 25% of women recommended for biopsy will be diagnosed with breast cancer. Breast biopsies are most often performed by a radiologist using either ultrasound, x-ray technology (stereotactic), or MRI to guide the biopsy.

For breast biopsies, after removing the tissue samples, the doctor may leave a tiny clip or marker, made of surgical-grade material, to identify the biopsy site. This will be visible on a mammogram. The marker points out the exact site of the biopsy so that a doctor can find it again easily if he or she need to. This is especially important if the patient has chemotherapy or another systemic treatment that change the size and shape of the mass. The mass may also disappear after treatment.

The vast majority of markers have a metal component of either titanium and/or stainless steel (about the size of a sesame seed). Some markers have a gel tube surrounding the metal component which expands inside the breast. This gel tube allows the radiologist to better visualize the clip under ultrasound and MRI for approximately 12-15 months.

The breast clip placement, indicating the location of a percutaneous breast core biopsy, is utilized in many settings:
Correlate lesion location across different imaging modalities (i.e. ultrasound, mammogram, tomosynthesis, MRI)
Follow up progression of benign lesions over time
Indicate tumor location in patients receiving neoadjuvant chemotherapy
Assist surgeons in localizing lesions or extent of disease in nonpalpable lesions, confirming excision of the appropriate region
Guide the pathologist to identify the area of interest on gross specimen examination
Different clips help distinguish separate lesions Clip migration away from the biopsied site is a well-recognized complication and occurs for various reasons.

The purpose of the biopsy clip when breast surgery is necessary:
a. Surgery will be necessary following a breast biopsy if the pathology results reveal cancer, pre-cancer, or non-invasive cancer, or a few other select diagnoses which are not cancer but complete surgical excision is necessary to ensure that a small focus of cancer is not present.
b. When performing a biopsy, the goal is not to remove all of the abnormality. Even if the entire abnormality were removed during biopsy, surgery would still be necessary for the above diagnoses to ensure that all of the abnormal tissue is removed.
c. The biopsy clip serves as a marker documenting where the tissue was sampled in the breast. If the original abnormality is no longer visible by imaging after the biopsy, the marker is the only guide we have to know where the diseased tissue was sampled.
d. On the day of surgery, the marker is used as a target for the radiologist to place a wire through the breast up to the marker, referred to as wire localization. The wire may be placed using ultrasound, stereotactic, or MRI imaging for guidance.
e. The patient is then transferred to surgery where the surgeon will use the wire as a guide to remove more tissue surrounding the biopsy clip.
f. The portion of the breast removed by the surgeon, referred to as a tissue specimen, is then radiographed (x-rayed) to show that the biopsy clip and the wire were removed from the breast.

The purpose of the biopsy clip when the breast biopsy results are not cancer, and surgery is not necessary:
a. Again, the goal in image-guided breast biopsy is not to remove all of the abnormality. In most cases at least part of the abnormality will still be visible on imaging after the biopsy.
b. If the pathology results from a breast biopsy do not prompt breast surgery, patients will either undergo imaging at 6 months or 12 months following the biopsy depending on the facility.
c. The original mass or some of the targeted calcifications will often remain on follow-up imaging. Seeing a biopsy clip within the abnormality been biopsied, and that surgery was is reassuring that the finding has not necessary.

SCHEDULE L

Teledermatology Modes of Communication

Teledermatology services can be delivered synchronously between the participants (i.e. a real-time conversation between patient and dermatologist (live-interactive teledermatology or videoconferencing)), or asynchronously at different points in time.
(i) Real-Time Synchronous Modes.
Voice calls—The simplest and most widespread form of teledermatology in practice today is a simple voice call via the telephone. This allows the practitioner and patient to quickly exchange information. Given the lack of visual information (images/video), its use for diagnosis, assessment, and management is limited and very rarely meets the criteria for reimbursed teledermatology due to the lack of physical examination and verifiable disease. Therefore, most teledermatology employs visual data implemented into practice for accuracy and quality assurance.

Live Video Interaction—Live video interaction is a popular mode of communication in telemedicine and has been thoroughly researched for implementation in dermatology. It offers the same voice interaction between the participants as on the telephone and the live camera can be directed towards a rash or skin lesion for visual inspection in real-time. In most cases, it lacks the quality of high definition still images in particular because patients' internet speed may not be able to support a full high-definition video consultation.

(ii) Asynchronous Modes.

Store-and-Forward teledermatology—In "store-and-forward" teledermatology images or video are transmitted to allow for a consultation to happen asynchronously. It allows the participants to not only communicate at a distance but also at different points in time. A consultation typically happens with a series of high-quality images and relevant patient information being sent for remote evaluation.

Given the flexibility of the asynchronous nature of store-and-forward teledermatology, it is the most promising and convenient variant of teledermatology. It does not require scheduling for the provider and patient to be available at same time. It allows for more efficient use of a dermatologist's scarce time, since he or she is not waiting for patients to present and avoids "no shows," which can be a big issue in healthcare systems with long wait times for access.

(iii) Teledermatology: Real-time Video vs. Store-and-Forward.

Live video interaction between a medical practitioner and a patient is currently the most commonly reimbursed form of teledermatology since video is an already commonly reimbursed telehealth solution in other medical fields.

Store-and-forward telehealth services may be a better solution in dermatology and are also reimbursed. Some of the advantages of store-and-forward over real-time are that it works on any internet connection speed and does not require appointment scheduling between the patient and provider for more flexibility and convenience for both. It can, therefore, help reduce wait times.

There is evidence that store-and-forward teledermatology in the right setting can be more cost-effective, especially when used as a triage mechanism to reduce face-to-face appointments and in rural settings.

A cost-effectiveness study demonstrated that store-and-forward teledermatology achieved high patient satisfaction and afterwards no evident increased utilization or further post-consultation costs.

SCHEDULE M

Common Current Use of Physical Skin Markers in Allergy Testing, Radiation Treatment, Skin Biopsies, and General Surgery A. Allergy Testing.

There are currently three types of skin testing methods used to determine if you are allergic to a certain substance. The most common of the three is known as a "Skin Prick Test", also referred to as a skin scratch or puncture test (the "Skin Prick Test"). It is used to check for immediate allergic reactions to as many as 40 different allergens at once, including without limitation allergies to pollen, mold, pet dander, dust mites, and food allergies. The tests are done in one of two places, which are the inner forearm and the upper back. The forearm is used mostly for adults, while upper back tests are performed on children. Typically the forearm is coded with a skin pen marker corresponding to the number of allergens being tested.

A brief overview of how the Skin Prick Test is currently performed is as follows:
  (i) Clean arm with soap, water, or alcohol.
  (ii) The forearm is coded with a skin pen marker corresponding to allergens being tested. Marks should be at the number of least 2 centimeters apart. One of the common problems of skin prick testing is placing the tests too close together (<2 centimeters apart), so that spreading of allergen solutions between test sites occurs.
  (iii) A drop of allergen solution is placed beside each mark.
  (iv) A small prick through the drop is made to the skin using a sterile prick lancet. A new lancet must be used for each allergen tested.
  (v) Excess allergen solution is dabbed off with a tissue.
  (vi) Observe skin reactions—if a reaction occurs it should do so within 20-30 minutes. Reactions are assessed by the degree of redness and swelling and the size of the weal produced.

B. Radiation Treatment.

Preparation of site of radiation delivery is an important process in radiation treatment planning, and plays a crucial role during a course of radiotherapy to achieve reproducibility of set-up and accuracy of treatment delivery. Radiotherapy tattoos or skin markings help make sure external radiotherapy treatment is accurate. During your radiotherapy planning session, your radiographer (sometimes called a radiotherapist) might make between one to five permanent pin-point tattoo marks on your skin. Your radiographer uses the tattoos to line up the radiotherapy machine for each treatment. This makes sure they treat exactly the same area each time.

Your radiographer might also draw marks around the tattoos with permanent ink pen. This highlights the tattoos so they can be seen more easily in the room where you have treatment, which can be dark. You should not try to wash them off.

The pen marks will start to rub off in time. They can rub off on your clothes or when you wash. Tell your radiographer if that happens. They can redraw them the next time you have treatment.

C. Skin Biopsies.

In performing a skin biopsy a dermatologist or nurse cleans the area of the skin to be biopsied. The area of skin may be marked to outline the biopsy area.

A skin biopsy is a procedure to remove cells or skin samples from your body for laboratory examination. A dermatologist uses a skin biopsy to diagnose skin conditions and remove abnormal tissue.

The three main types of skin biopsies are:
  Shave biopsy. A doctor uses a tool similar to a razor to remove a small section of the top layers of skin (epidermis and a portion of the dermis).
  Punch biopsy. A doctor uses a circular tool to remove a small core of skin, including deeper layers (epidermis, dermis, and superficial fat).
  Excisional biopsy. A doctor uses a small knife (scalpel) to remove an entire lump or an area of abnormal skin, including a portion of normal skin down to or through the fatty layer of skin.

The dermatologist or nurse then cleans the area of the skin to be biopsied. Your skin may be marked to outline the biopsy area, and you then receive a medication (local anesthetic) to numb the biopsy site.

After the biopsy is complete, your dermatologist sends the skin biopsy sample to a laboratory for testing. Results may take several days or longer, sometimes up to months, depending on the type of biopsy and the lab's procedures.

Healing of your biopsy wound can take several weeks, but is usually complete within two months. Wounds on the legs and feet tend to heal slower than those on other areas of the body.

Lab results may take several days or longer, sometimes up to months, depending on the type of biopsy and the lab's procedures.

If your results were normal, it means no cancer or skin disease was found. If your results were not normal, you may be diagnosed with one of the following conditions:

A bacterial or fungal infection.

A skin disorder such as psoriasis.

Skin cancer. Your results may indicate one of three types of skin cancers: basal cell, squamous cell, or melanoma.

For certain results, follow-up surgery may be required.

D. Breast Biopsies.

For breast biopsies, no matter the type of imaging utilized to guide the breast biopsy, be they ultrasound, x-ray technology (stereotactic), or MRI, the current standard of care at the completion of the biopsy is placement of a physical biopsy marker.

The vast majority of markers have a metal component of either titanium and/or stainless steel (about the size of a sesame seed). Some markers have a gel tube surrounding the metal component which expands inside the breast. This gel tube allows the radiologist to better visualize the clip under ultrasound and MRI for approximately 12-15 months.

Clip marker migration away from the biopsite site is a well-recognized complication and occurs for various reasons.

Statistically, 25% of women recommended for a breast biopsy will be diagnosed with breast cancer. Breast biopsies are most often performed by a radiologist using either ultrasound, x-ray technology (stereotactic), or MRI to guide the biopsy.

For breast biopsies, after removing the tissue samples, the doctor may leave a tiny clip or marker, made of surgical-grade material, to identify the biopsy site. This will be visible on a mammogram. The marker points out the exact site of the biopsy so that a doctor can find it again easily if he or she need to. This is especially important if the patient has chemotherapy or another systemic treatment that change the size and shape of the mass. The mass may also disappear after treatment.

The vast majority of markers have a metal component of either titanium and/or stainless steel (about the size of a sesame seed). Some markers have a gel tube surrounding the metal component which expands inside the breast. This gel tube allows the radiologist to better visualize the clip under ultrasound and MRI for approximately 12-15 months.

The breast clip placement, indicating the location of a percutaneous breast core biopsy, is utilized in many settings to:

(i) Correlate lesion location across different imaging modalities (i.e. ultrasound, mammogram, tomosynthesis, MRI).

(ii) Follow up progression of benign lesions over time.

(iii) Indicate tumor location in patients receiving neoadjuvant chemotherapy.

(iv) Assist surgeons in localizing lesions or extent of disease in nonpalpable lesions, confirming excision of the appropriate region.

(v) Guide the pathologist to identify the area of interest on gross specimen examination.

(vi) Different clips help distinguish separate lesions.

Clip migration away from the biopsied site is a well-recognized complication and occurs for various reasons.

The purpose of the biopsy clip when breast surgery is necessary:

(i) Surgery will be necessary following a breast biopsy if the pathology results reveal cancer, pre-cancer, or non-invasive cancer, or a few other select diagnoses which are not cancer but complete surgical excision is necessary to ensure that a small focus of cancer is not present.

(ii) When performing a biopsy, the goal is not to remove all of the abnormality. Even if the entire abnormality were removed during biopsy, surgery would still be necessary for the above diagnoses to ensure that all of the abnormal tissue is removed.

(iii) The biopsy clip serves as a marker documenting where the tissue was sampled in the breast. If the original abnormality is no longer visible by imaging after the biopsy, the marker is the only guide we have to know where the diseased tissue was sampled.

(iv) On the day of surgery, the marker is used as a target for the radiologist to place a wire through the breast up to the marker, referred to as wire localization. The wire may be placed using ultrasound, stereotactic, or MRI imaging for guidance.

(v) The patient is then transferred to surgery where the surgeon will use the wire as a guide to remove more tissue surrounding the biopsy clip.

(vi) The portion of the breast removed by the surgeon, referred to as a tissue specimen, is then radiographed (x-rayed) to show that the biopsy clip and the wire were removed from the breast.

The purpose of the biopsy clip when the breast biopsy results are not cancer, and surgery is not necessary:

(i) Again, the goal in image-guided breast biopsy is not to remove all of the abnormality. In most cases at least part of the abnormality will still be visible on imaging after the biopsy.

(ii) If the pathology results from a breast biopsy do not prompt breast, patients will either undergo imaging at 6 months or 12 months following the biopsy depending on the facility.

(iii) The original mass or some of the targeted calcifications will often remain on follow-up imaging. Seeing a biopsy clip within the abnormality is reassuring that the finding has been biopsied, and that surgery was not necessary.

E. General Surgery.

A simple measure to support a patient's safety and to avoid wrong site surgery is preoperative skin marking. "Marking the surgical site appears to be a key step in the prevention of site errors; it is one of three elements of standard operating protocol."

Set forth is a copy of "Implementation Expectations for the Universal Protocol for Preventing Wrong Site, Wrong Procedure, and Wrong Person Surgery":

"Implementation Expectations for the Universal Protocol for Preventing Wrong Site, Wrong Procedure, and Wrong Person Surgery These guidelines provide detailed implementation requirements, exemptions, and adaptations for special situations.

Preoperative Verification Process

Verification of the correct person, procedure, and site should occur (as applicable):
At the time the surgery/procedure is scheduled.
At the time of admission or entry into the facility.
Anytime the responsibility for care of the patient is transferred to anothercaregiver.
With the patient involved, awake, and aware, if possible.
Before the patient leaves the preoperative area or enters the procedure/surgical room.
A preoperative verification checklist may be helpful to ensure availability and review of the following, prior to the start of the procedure:
Relevant documentation (e.g., history and physical, consent).
Relevant images, properly labeled and displayed.
Any required implants and special equipment.

Marking the Operative Site

Make the mark at or near the incision site. Do NOT mark any nonoperative site(s) unless necessary for some other aspect of care.
The mark must be unambiguous (e.g., use initials or "YES" or a line representing the proposed incision; consider that "X" may be ambiguous).
The mark must be positioned to be visible after the patient is prepped and draped.
The mark must be made using a marker that is sufficiently permanent to remain visible after completion of the skin prep. Adhesive site markers should not be used as the sole means of marking the site.
The method of marking and type of mark should be consistent throughout the organization.
At a minimum, mark all cases involving laterality, multiple structures (fingers, toes, lesions), or multiple levels (spine). Note: In addition to preoperative skin marking of the general spinal region, special intraoperative radiographic techniques are used for marking the exact vertebral level.
The person performing the procedure should do the site marking.
Marking must take place with the patient involved, awake, and aware, if possible.
Final verification of the site mark must take place during the "time out."
A defined procedure must be in place for patients who refuse site marking.

Exemptions

Single organ cases (e.g., Cesarean section, cardiac surgery).
Interventional cases for which the catheter/instrument insertion site is not predetermined (e.g., cardiac catheterization).
Teeth—but, indicate operative tooth name(s) on documentation or mark the operative tooth (teeth) on the dental radiographs or dental diagram.
Premature infants, for whom the mark may cause a permanent tattoo.

"Time Out" Immediately Before Starting the Procedure

Must be conducted in the location where the procedure will be done, just before starting the procedure. It must involve the entire operative team, use active communication, be briefly documented, such as in a checklist (the organization should determine the type and amount of documentation), and must, at the least, include:
Correct patient identity.
Correct side and site.
Agreement on the procedure to be done.
Correct patient position.
Availability of correct implants and any special equipment or special requirements.
The organization should have processes and systems in place for reconciling differences in staff responses during the "time out."

Procedures for Non-OR Settings, Including Bedside Procedures

Site marking must be done for any procedure that involves laterality, multiple structures, or levels (even if the procedure takes place outside of an OR).
Verification, site marking, and "time out" procedures should be as consistent as possible throughout the organization, including the OR and other locations where invasive procedures are done.
Exception: Cases in which the individual doing the procedure is in continuous attendance with the patient from the time of decision to do the procedure and consent from the patient through to the conduct of the procedure may be exempted from the site marking requirement. The requirement for a "time out" final verification still applies.

[Reprinted with permission from: Universal Protocol for Preventing Wrong Site, Wrong Procedure, Wrong Person Surgery. Oakbrook Terrace, IL: Joint Commission on Accreditation of Healthcare Organizations. 2003]
From: Chapter 36, Wrong-Site Surgery: A Preventable Medical Error
Patient Safety and Quality: An Evidence-Based Handbook for Nurses.
Hughes R G, editor.
Rockville (MD): Agency for Healthcare Research and Quality (US); 2008 April"

SCHEDULE N

Non-Skin Health Data

Examples of non-skin "health data" of the Subject may include (without limitation) those items set forth below:
(1) Blood Analysis
Subject blood analysis data can be obtained from a clinical laboratory, such as Quest Diagnostics. Hundreds of hematological tests and procedures have been developed, and many can be carried out simultaneously on one sample of blood with such instruments as autoanalyzers (which are discussed below). Such tests for a subject typically need to be ordered by a physician, and physicians generally place great reliance on the results of such tests. Blood tests may include, without limitation:
(a) blood Count
A complete blood count (CBC) is a blood test used to evaluate your overall health and detect a wide range of disorders, including anemia, infection, and leukemia. A complete blood count test measures several components and features of your blood, including: (i) red blood cells, which carry oxygen, (ii) white blood cells, which fight infection, (iii) hemoglobin, the oxygen-carrying protein in red blood cells, (iv) hematocrit, the proportion of red blood cells to the fluid component, or plasma, in your blood, (v) platelets, which help with blood clotting.

Abnormal increases or decreases in cell counts as revealed in a complete blood count may indicate that you have an underlying medical condition that calls for further evaluation. [See generally https://www.mayoclinic.org/tests-procedures/complete-blood-count/about/pac-20384919].

(b) Blood Typing

Blood type is comprised of two blood groups: ABO and Rh Blood types are based on antigens on the surface of your red blood cells. An antigen is a substance that triggers an immune response by your body against that substance. Blood typing is typically done by a phlebotomist. A phlebotomist (someone trained to draw blood) will use a needle to draw blood from your arm or hand at your doctor's office, a clinical laboratory, or a hospital. Alternatively, there are at-home blood typing tests.

With at-home blood typing tests, they typically ask that you prick your finger with a lancet and put drops of your blood on a special card. After putting the blood on the card, you can observe the areas where blood clumps or spreads out, and then match those reactions to an included guide. Some home testing kits have vials of fluid for your blood, as opposed to a card. [See generally https://www.healthline.com/health/how-to-find-out-your-blood-type#blood-testing].

(c) Bone Marrow Aspiration

Bone marrow aspiration is a procedure that involves taking a sample of the liquid part of the soft tissue inside your bones. Bone marrow is the spongy tissue found inside bones. It contains cells that produce white blood cells (WBCs), red blood cells (RBCs), and platelets inside larger bones. Conditions and diseases related to bone marrow problems include: (i) anemia, which is a low red blood cell count, (ii) bone marrow diseases, such as myelofibrosis or myelodysplastic syndrome, (iii) blood cell conditions, such as leukopenia or polycythemia vera, (iv) cancers of the bone marrow or blood, such as leukemia or lymphoma, (v) hemochromatosis, which is a genetic disorder in which iron increases in the blood and builds in organs and tissues, (vi) infection, especially chronic diseases like tuberculosis, and (vii) storage diseases, such as amyloidosis or Gaucher's disease. Bone marrow aspiration can be an important test if one is having cancer treatment, as it can help determine if the cancer has spread to the bones. [See generally https://www.healthline.com/health/bone-marrow-aspiration#purpose].

(d) cephalin-cholesterol flocculation

A cephalin-cholesterol flocculation test is a laboratory test for the nonspecific measurement of blood globulins, a group of proteins that appear in abnormally high concentrations (hyperglobulinemia) in association with certain diseases. The test consists of adding blood serum to a suitably prepared emulsion of cephalin-cholesterol. A flocculent precipitate will form if the serum is abnormally high in globulins.

The test is helpful in confirming the presence of liver disease, subacute bacterial endocarditis, rheumatoid arthritis, and malaria. [See generally https://www britannica.com/science/cephalin-cholesterol-flocculation].

(e) Enzyme Analysis

Enzyme analysis, in blood serum, is a measurement of the activity of specific enzymes in a sample of blood serum, usually for the purpose of identifying a disease. The enzymes normally are concentrated in cells and tissues where they perform their catalytic function; in disease, however, certain enzymes tend to leak into the circulation from the injured cells and tissues. More than 50 enzymes have been found in human serum. [See generally https://www.britannica.com/science/enzyme-analysis].

(f) Epinephrine Tolerance Test

An epinephrine tolerance test is an assessment of the metabolism of liver glycogen by measuring the blood-sugar response to a standard dose of epinephrine (adrenalin). Individuals with liver disease or with an inherited deficiency of the enzymes that degrade glycogen to glucose show subnormal response. [See https://www.britannica.com/science/epinephrine-tolerance-test].

(g) Glucose Tolerance Test

The glucose tolerance test is a medical test in which glucose is given and blood samples taken afterward to determine how quickly it is cleared from the blood. The test is usually used to test for diabetes, insulin resistance, impaired beta cell function, and sometimes reactive hypoglycemia and acromegaly, or rarer disorders of carbohydrate metabolism. [See generally https://en.wikipedia.org/wiki/Glucose_tolerance_test].

(h) Hematocrit

A hematocrit test measures how much of your blood is made up of red blood cells. Red blood cells contain a protein called hemoglobin that carries oxygen from your lungs to the rest of your body. Hematocrit levels that are too high or too low can indicate a blood disorder, dehydration, or other medical conditions. [See generally https://medlineplus.gov/lab-tests/hematocrit-test/].

(i) Immunologic Blood Test

An immunologic blood test is any of a group of diagnostic analyses of blood that employ antigens (foreign proteins) and antibodies (immunoglobulins) to detect abnormalities of the immune system. Immunity to disease depends on the body's ability to produce antibodies when challenged by antigens. Antibodies bind to and help eliminate antigens from the body. The inability of the body to produce certain classes of immunoglobulins (IgG, IgA, IgM, IgD, IgE) can lead to disease. Complexes formed by the antigen-antibody reaction can be deposited in almost any tissue and can lead to malfunction of that organ. [See generally https://www.britannica.com/science/immunologic-blood-test].

(j) Inulin Clearance

Inulin is a sugar found in plants that is poorly digested by humans. It is used to estimate the health of the kidneys by assessing their ability to filter inulin from blood, after it has been administered. The Inulin Clearance Blood Test helps determine the inulin clearance rate, which is the rate at which insulin leaves blood. It helps assess kidney function. [See https://www.dovemed.com/common-procedures/procedures-laboratory/inulin-clearance-blood-test/].

(k) Liquid Biopsies

These tests pick up genetic material shed by cancer tumors into the blood. For now, these blood-based tests are used not to screen for cancer in healthy subjects but to guide treatment in those who have already been diagnosed. [See generally A. Park, "Why doctors are turning to blood to learn more about tumors", Time, vol. 196, no. 15, 2020, at P-25.]

(l) Serological Test

Also called serology test or antibody test, a serological test is any of several laboratory procedures carried out on a sample of blood serum (the clear liquid that separates from the blood when it is allowed to clot) for the purpose of detecting antibodies or antibody-like substances that appear specifically in association with certain diseases. There are different types of serological tests—for example, flocculation tests, neutralization tests, hemagglutinin-inhibition tests, enzyme-linked immunosorbent assays (ELISAs), and chemiluminescence immunoassays. Serological testing is particularly helpful in the diagnosis of certain bacterial, parasitic, and viral diseases, including Rocky Mountain spotted fever, influenza, measles, polio, yellow fever, and infectious mononucleosis. It is also useful in the detection of autoantibodies (harmful antibodies that attack components of the body) that are involved in autoimmune diseases, such as rheumatoid arthritis. As a practical mass-screening tool, serological testing has proved valuable in the detection of diseases such as syphilis, HIV/AIDS, and epidemic and pandemic infectious diseases (e.g., influenza and coronavirus disease). [See generally https://www.britannica.com/science/serological-test].

(m) Thymol Turbidity

Thymol turbidity is a laboratory test for the nonspecific measurement of globulins, a group of blood proteins that appear in abnormally high concentration in association with a wide variety of diseased states, notably those affecting the liver. The test consists of adding 1 volume of blood serum to 60 volumes of a buffer supersaturated with thymol; the thymol-globulin interaction results in turbidity, the degree of which varies with the concentration of globulins. High turbidity is observed in approximately 80 to 90 percent of individuals with acute viral hepatitis and in 20 to 70 percent of those with cirrhosis. The test is also useful in the differential diagnosis of the two main types of jaundice. Today, thymol turbidity is rarely used. Techniques that are capable of distinguishing between the different types of globulins and other blood proteins are used instead. [See generally https://www.britannica.com/science/thymol-turbidity].

(2) Blood Pressure

Blood pressure is a measurement of the force of blood against the arterial walls when the heart pumps. The pressure is measured in millimeters of mercury (mmHg) and is expressed as two numbers. For example, the optimal BP for an adult is 120 over 80, or 120/80. The top number, called the systolic pressure, measures the highest pressure exerted when the heart contracts. The bottom number, called the diastolic pressure, shows the minimum pressure against the arteries when the heart rests between beats. Blood pressure is measured with an instrument called a sphygmomanometer. It is measured with a cuff and stethoscope while the arm is in a resting position. The cuff is placed about one inch above the bend of the elbow, and is inflated until the mercury dial reaches 30 points higher than the person's usual systolic pressure, or 210 if previous data is not available. A stethoscope is placed on an artery in the inside of the elbow, and the air is slowly allowed to escape from the cuff. The point at which the sound of the pulse is first heard is the systolic pressure number; the point at which the sound disappears is the diastolic number. Several factors can affect blood pressure, so one high reading does not necessarily mean that a person has hypertension, or high blood pressure. Immediate stimuli such as fear, pain, anger, and some medications can temporarily raise a person's BP. Blood pressure readings can also be affected by factors such as, without limitation, (i) smoking, (ii) coffee or other caffeinated drinks, (iii) a full bladder, and (iv) recent physical activity. Blood pressure is also affected by one's emotional state and the time of day.

If a high reading has occurred, and one of these factors is present, then the person needs to be monitored repeatedly over a period of time to determine if this is a persistent Condition, or if the reading was simply based on circumstances.

Hence, an alternate type of Subject data input (and processing and/Ä. output review), such as Subject skin data input, processing, and output as described by the invention, can potentially assist in measuring if a Subject's potential condition indication is more or less valid as well as its apparent trend.

(3) Pulse Oximetry

Pulse oximetry measures the oxygen level (oxygen saturation) in the blood. A pulse oximeter is a simple device that is used to measure how well oxygen is being sent from the heart to different parts of the body, including your legs, arms, among other parts. Every organ and system in your body needs a good supply of oxygen to survive and thrive. Without a proper amount of oxygen, cells will slowly start to malfunction and ultimately die. This can eventually lead to system and organ failure. [See generally https://www.besthealthncare.com/how-to-read-a-finger-pulse-oximeter/]. Conditions that may prevent one's lungs from inhaling sufficient oxygen include, without limitation, heart disease, anemia, collapsed lung, pulmonary embolism, and/or Covid 19. [Id.] Pulse oximetry may be used: (i) to monitor how well lung medicines are working, (ii) if you are suffering from conditions such as heart failure, heart attack, asthma, pneumonia, anemia, lung cancer, and chronic obstructive pulmonary disease, (iii) during or after a procedure that uses sedation, and (iv) to check whether you need a ventilator to help with breathing, and (v) to check if you have a moment when breathing stops while you are asleep. [Id.]

Today pulse oximetry data can be obtained on an Apple Watch or similar device (and arguably the Subject owns this data) or on comparatively inexpensive standalone pulse oximeters which can be purchased on the internet. Hence, a Subject's pulse oximetry data can today be obtained directly by the Subject, as well as with the assistance of a Professional.

(4) Body Mass Index

Body mass index (BMI) is a measure of body fat based on height and weight that applies to adult men and women. [See generally https://www.nhlbi.nih.gov/health/educational/lose_wt/BMI/bmicalc.htm]. Your BMI is a good indicator of your risk factors for certain conditions like cardiovascular disease and diabetes. [See generally https://www.healthcentral.com/article/home-body-weight-tests]. Today smart scales make it easier than ever to measure user weight and usually contain a BMI measurement function to test a user's body fat percentage at home. For example, the Fitbit Aria WiFi Smart Scale measures a user's weight, body fat percentage, and BMI to provide a full picture of the user's weight management trends. These scales transmit an electrical signal from your feet and scan your body, and use WiFi to automatically transmit a user's weight and BMI data wirelessly to his or her smartphone or computer, and create for him or her a customized weight and/or BMI "data chart" showing trends based on the date of the weight and BMI measurement data points over time.

(5) Weight

"Underweight", "normal", "overweight", and "obese" are all labels for ranges of weight. Obese and overweight mean that your weight is greater than it should be for your health. Underweight means that it is lower than it should be for your health. Your healthy body weight depends on your sex and height. For children, it also depends on your age. A sudden, unexpected change in weight can be a sign of a medical problem. Causes for sudden weight loss can include, without limitation: (i) thyroid problems, (ii) cancer, (iii) infectious diseases, (iv) digestive diseases, (v) certain medicines. Sudden weight gain can be due to medicines, thyroid problems, heart failure, and kidney disease. See the discussion of smart scales under "Body Mass Index" above.

(6) Urine Sample Data

Clinical urine tests (also known as urinalysis, UA) is an examination of urine for certain physical properties, solutes, cells, casts, crystals, organisms, or particulate matter, and mainly serves for medical diagnosis. Urine culture (a microbiological culture of urine) and urine electrolyte levels are part of urinalysis. [See generally https://en.wikipedia.org/wiki/Clinical_urine_tests]. Many disorders may be detected in their early stages by identifying substances that are not normally present in the urine and/or by measuring abnormal levels of certain substances.

Some examples include glucose, protein, bilirubin, red blood cells, white blood cells, crystals, and bacteria. They may be present because, without limitation: (i) there is an elevated level of the substance in the blood and the body responds by trying to eliminate the excess in the urine, (ii) kidney disease is present, or (iii) there is a urinary tract infection present, as in the case of bacteria and white blood cells. [See generally https://labtestsonline.org/tests/urinalysis#:~:text=A%20urinalysis%20is %20a %20group%20of%20physical%2C%20chemical%2C, and%20abnormal%20metabolism %2C%20cells%2C%20cellular%20fragments%2C%20and %20bacteria].

(7) Stool Sample Data

A stool test is used to detect the presence of blood or other gastrointestinal abnormalities, such as colon or gastric cancer, inflammatory bowel disease, hemorrhoids, anal fissures or infections. There are two main types of stool tests to choose from: (i) a fecal occult blood test (FOBT), which detects the presence of blood in your feces, and (ii) a stool DNA test, which detects the presence of genetic material from polyps and cancerous tumors. [See generally https://www.very wellhealth.com/stool-test-options-796641].

(8) Pregnancy Test Data

Human pregnancy tests work by checking a subject's urine (pee) for a hormone called human chorionic gonadotropin (HCG). A subject's body only makes this hormone if the subject is pregnant. Pregnancy tests are usually inexpensive-they can cost as little as a dollar. Sometimes you can get a free pregnancy test at certain health centers. You can also get a pregnancy test from your nurse or doctor, or community clinic. [See generally https://www.plannedparenthood.org/learn/pregnancy/pregnancy-tests].

(9) Saliva Test Data

A saliva test is a medical test in which a sample of saliva is analyzed, often in order to measure a person's hormone levels. Many saliva home test kits are available.

(10) Allergy Test Data

An allergy test is an exam performed by a trained allergy specialist to determine if the subject's body has an allergic reaction to a known substance. The exam can be in the form of a blood test, a skin test, or an elimination diet. Allergies occur when a subject's immune system, which is a subject's body's natural defense, overreacts to something in the subject's environment. For example, pollen, which is normally harmless, can cause a subject's body to overreact. Allergy tests involve exposing the subject to a very small amount of a particular allergen and recording the reaction. [See generally https://www.healthline.com/health/allergy-testing#allergy-types].

(11) ECG measurement and spot Atrial Fibrillation (AFib)

The irregular heartbeats of Atrial Fibrillation ("Afib") are not always medically dangerous, but they can lead to complications such as stroke, blood clots and even heart failure. Today ECG measurement and spot AFib can be obtained on an Apple Watch or similar device (and arguably the Subject owns this data) or on comparatively inexpensive standalone ECG measurement and spot AFib device.

The Apple Watch can also occasionally check your heart rate with its automatic heart rate sensor, and will send you an alert if it notices anything abnormal. Hence, today a Subject's ECG measurement and spot AFib pulse oximetry data can be obtained directly by the Subject, as well as with the assistance of a Professional.

(12) DNA/Genetic Test Data

Currently, only about a quarter of cancer patients get detailed genetic testing of their tumors. [See generally A. Park, "Why doctors are turning to blood to learn more about tumors", Time, vol. 196, no. 15, 2020, atp.25.]

(13) Brainwave Test Data

A brainwave is the rapid fluctuations of voltage between parts of the cerebral cortex that are detectable with, for example, an electroencephalograph (EEG), which allows researchers to note brain wave patterns. All humans display five different types of electrical patterns or brain waves across the cortex. Each brain wave has a purpose and helps serve us in optimal mental functioning. Data such as video or EEG measures taken over a period of time can be synchronized. This process can be used in diagnosing and monitoring epilepsy or monitoring shared behavioral and brain dynamics. [See generally https://itsusync.com/different-types-of-brain-waves-delta-theta-alpha-beta-gamma-ezp-9]. The detection of brain signals is achieved through electrodes placed on the scalp. There are several ways to develop a noninvasive brain-computer interface, such as EEG (electroencephalography), MEG (magnetoencephalography), or MRT (magnetic resonance tomography). [See generally https://search.yahoo.com/yhs/search;_ylt=AwrWmjlgRYNfYSsAQAYPxQt.;_ylu=Y29sbwNncTEEcG9zAzEEdnRpZAMEc2VjA3Bh Z21uYXRpbG24-?p=brainwave+data+definition&ei=UTF-8&type=em_appfocusl_me&fr=yhs-pty-pty_email&ff2=rs-bottom%2Cp%3As%2Cv%3Aw%2Cm%3Aats&param1=20190209&param2=0671e462-beec-4071-b2dc-f32f8950ee2a&param3=email_%7EUS %7Eappfocus 1%7E¶m4=g-cccl-lpO-bb8-sbe-ab % 7EEdgeium %7Ebrainwave+ data%7ED41D8CD98F00B204E9800998ECF8427E %7EWin10&hsimp=yhs-ptyemail&hspart=pty &b=11&pz=10&bct=0&xargs=0].

(14) Glucose Monitoring Device Data

A glucose monitoring device is a device worn by a person who is a diabetic, which provides continuous glucose monitoring for the management of diabetes. It detects trends and tracks patterns aiding in the detection of episodes of hyperglycemia and hypoglycemia, thereby facilitating both acute and long-term therapy adjustments. An example of such a device is the "Freestyle Libre 14 day Flash Glucose Monitoring System", a product of Abbott Diabetes Care, Inc. Also, a California-based company, Dexcom, in 2019 announced that its G6 glucose tracker would soon be able to send monitoring data to the Apple Watch, benefiting Apple Watch users with diabetes.

(15) "Brain Age Index" Data

Researchers recording polysomnograms—records of brain waves, blood oxygen levels, heart rates, respiration, and muscle movements during sleep—have created a "brain age index" derived from a machine learning algorithm that analyzes brain waves during different stages of sleep and models normal brain activity across the human lifespan. The brain age index is basically the brain age subtracted by the chronological age. A high brain age index is a strong indicator of accelerated aging. Patients with dementia tend to have brain activity that appears "older" than the patient's chronological age. It is the inventor's view that the brain age index—in combination with other screening tools, such as the collection, analysis, and cross-comparison of skin data, as described in, and part of, the invention—can act as an "early warning system" for dementia and other neurological conditions. In 2014, an estimated five million adults over the age of 65 suffered from dementia, and that number is projected to reach nearly 14 million by 2060. A recent study suggests 61.7 percent of dementia cases go undiagnosed. [See generally https://www.thecrimson.com/article/2020/10/9/dementia-prediction-tool/]

(16) Prescription Pharmaceuticals, Nutraceuticals, and other Over-the-Counter Drugs being Consumed by the Subject (and Data Related Thereto)

A prescription drug (also prescription medication or prescription medicine) is a pharmaceutical drug that legally requires a medical prescription to be dispensed. In contrast, over-the-counter drugs can be obtained without a prescription. The reason for this difference in substance control is the potential scope of misuse, from drug abuse to practicing medicine without a license and without sufficient education. Different jurisdictions have different definitions of what constitutes a prescription drug. [See generally https://en.wikipedia.org/wiki/Prescription_drug#:~:text=A%20prescription%20drug%20%28also%20prescription%20medication%20or%20prescription,over-the-counter%20drugs%20can%20be%20obtained%20without%20a%20prescription].

A nutraceutical or 'biocuetical is a pharmaceutical alternative which claims physiological benefits. In the United States, "nutraceuticals" are largely unregulated, as they exist in the same category as dietary supplements and food additives by the FDA, under the authority of the Federal Food, Drug, and Cosmetic Act. The terms "nutraceutical" and "biocuetical" are not defined by U.S. law. Depending on its ingredients and the claims with which it is marketed, a product is regulated as a drug, dietary supplement, food ingredient, or food. [See generally https://en.wikipedia.org/wiki/Nutraceutical].

Prescription drugs, nutraceuticals, and over-the-counter (OTC) drugs can have side effects. Side effects, also known as adverse events, are unwanted or unexpected events or reactions to a drug. Side effects can vary from minor problems like a runny nose to life-threatening events, such as an increased risk of a heart attack. Several things can affect who does and does not have a side effect when taking a drug-age, gender, allergies, how the body absorbs the drug, other drugs, vitamins, and dietary supplements that you may be taking. [See generally https://www.fda.gov/drugs/drug-information-consumers/finding-and-learning-about-side-effects-adverse-reactions].

It should be noted that the invention in measuring and processing Subject's skin data (as described in the invention) has the potential to measure some of the effects on the skin and/or body of prescription drugs, nutraceuticals, and over-the-counter drugs on the user (human or animal) who or which are using them.

This attribute of the invention—i.e., the potential to measure some of the effects on the skin and/or body of prescription drugs, nutraceuticals, and over-the-counter drugs on the user (human or animal) who or which are using them—is important on a number of levels, including the fact that until the world produces customized prescription drugs, nutraceuticals, and over-the-counter drugs in customized doses based on a user's blood type, DNA, weight, gender, et al., such "additives" to the user's body will affect different users differently, and those differences in response are important to understand (in part because it allows for potentially better identifying and facilitating both acute and long-term therapy adjustments for user).

Summary Overview re Adding Additional "Health Data". Hence, adding an alternate type of Subject "health data" to a Subject's skin data (as described by the invention), can potentially assist in measuring if a Subject's potential health condition indication is either more or less valid as well as its apparent trend and the speed of that trend (thereby potentially better facilitating both acute and long-term therapy adjustments).

Over time, comparing and cross-referencing alternative types of Subject "health data" together with the Subject's skin data (as described by the invention) can potentially result in a virtuous cycle which potentially strengthens and cross-validates the potential Subject Condition indications identified by each type of data.

While any type of Subject "health data" can potentially come first in identifying a potential Subject health condition indication, which if potentially identified may be followed by the addition of one or more other types of "health data" for greater or lesser potential cross-validation, it is the inventor's view that the invention, given its ability in certain modes of use to work in an automatic mode or semi-automatic mode requiring little if any effort by the Subject, may for many potential Subject health conditions be the first line of potential indication of a Subject health condition, identifying Subject health conditions that otherwise might never be addressed or otherwise might be addressed much later, at a time in which it is much more costly and difficult to address the health condition, if at that point the health condition can meaningfully be addressed at all.

SCHEDULE O

Cameras

Some of the cameras used in the invention may include, without limitation, those listed below.

A. Wood Lamp Skin Examination.

Wood lamp examination is a diagnostic test in which the skin or hair is examined while exposed to the black light emitted by Wood lamp. Blacklight is invisible to the naked eye because it is in the ultraviolet spectrum, with a wavelength just shorter than the color violet. The lamp glows violet in a dark environment because it also emits some light in the violet part of the electromagnetic spectrum.

A traditional Wood lamp is a low-output mercury arc covered by a Wood filter (barium silicate and 9% nickel oxide) and emits wavelength 320-450 nm (peak 365 nm). The lamp was invented in 1903 by a Baltimore physicist, Robert W. Wood.

Modern black light sources may be specially designed BLB fluorescent lamps, mercury vapor lamps, light-emitting diodes, or incandescent lamps. Fluorescent black light tubes have a dark blue filter coating on the tube, which filters out most visible light. There are several models with varying properties. The medical Wood lamp may include:

A variety phosphors with different peak emission
Magnifying lens.
White light
Black drape to exclude light
Examination using Wood lamp involves the following steps.

1. Ideally, skin to be examined should not have been recently washed or had any makeup, deodorant or moisturizing cream applied, as these can fluoresce causing a false positive result.
2. Gentle facial skin cleansing may be required.
3. The Wood lamp is turned on to warm up for about a minute.
4. Room lights are turned off, and window shades are drawn, or black drape used to darken the surroundings completely.
5. After waiting to adapt to the dark, the skin is examined with Wood lamp for a few seconds. The lamp is held about 10-30 cm away from the skin. The examination is painless and safe.

A Wood lamp is used to identify the extent of pigmented or depigmented patches and to detect fluorescence. Normal healthy skin is slightly blue but shows white spots where there is thickened skin, yellow where it is oily, and purple spots where it is dehydrated. Clothing lint often shines bright white.

A positive result is reported if a pigmentary disorder is more noticeable when examined using the Wood lamp or if fluorescence is noted.

a. Fluorescence.

Fluorescence is a colored glow seen when certain substances such as collagen and porphyrins absorb black light and emit it again at a longer wavelength in the visible spectrum. Items on the skin surface such as fabric, topical medications and soap residue can also fluoresce.

b. Skin Conditions Diagnosed Using a Wood Lamp.

A Wood lamp for skin examination may reveal:
1. Increase in pigmentation (e.g., melasma, post inflammatory pigmentation) to determine whether the pigmentation is epidermal (pigmentation enhanced by Wood lamp examination) or dermal (pigmentation unchanged by Wood lamp examination). Pigmented lesions have a clear border under Wood light because the light is absorbed by increased melanin.
2. Loss of pigmentation (e.g., vitiligo) or reduced pigmentation (e.g., ash-leaf macules in tuberous sclerosis and hypomelanosis of Ito) to identify affected areas in light-skinned people. Hypopigmented skin has sharper borders under black light and fluoresces bright blue-white (or sometimes, yellowish green) due to accumulated biopterins. In contrast, areas of reduced blood flow are unchanged
3. *Pityriasis versicolor*—a slightly scaly persistent rash on anterior chest and back caused by Malassezia yeasts. When active, the scale emits a yellowish or orange glow.
4. Malassezia folliculitis—hair follicles fluoresce bluish-white.
5. Tinea capitis—areas of scale and baldness due to fungal infection. *Microsporum* species fluoresce blue-green (*M canis, M audouinii, M ferrugineum, M distortum*); *Trichophyton schoenleinii* fluoresces dull blue. Fungal infection due to other organisms does not fluoresce.
6. Head lice and scabies.
7. Erythrasma—corynebacteria bacteria cause a pigmented rash in skin folds that fluoresces a coral-pink color.
8. *Pseudomonas* in spa pool folliculitis and wound infection fluoresces green.
9. Acne fluoresces orange-red due to cutibacteria in hair follicles.
10. Porphyria causes red-pink fluorescence of the skin (porphyria cutanea tarda), or teeth (erythropoetic porphyria).
11. Porphyrins used as the photosensitizer in photodynamic therapy.
12. Drugs on the skin surface-tetracyclines and mepacrine fluoresce after oral ingestion
13. The evenness of application of a salicylic acid-containing chemical peel (this fluoresces green).

c. Some Other Uses for Wood Lamp:
1. Biochemistry laboratory may look for signs of porphyria in red blood cells (erythropoietic protoporphyria), urine and stool (porphyria cutanea tarda).
2. Molecular biology laboratory may use a Wood lamp to detect compounds with a fluorescent tag.
3. Aestheticians check for signs of ageing skin and other imperfections.
4. Ophthalmologists look for scratches and foreign bodies in the cornea of the eye.
5. Veterinary surgeons use the Wood lamp when examining pets for bacterial, fungal, or parasitic infection.
6. Law enforcement officers examine crime scenes and clothing for semen and urine.
7. Pet or rodent urine/feces is easily detected using a Wood lamp.
8. Metal fatigue can be evaluated using a fluorescent fluid and Wood lamp examination.
9. Nightclubs use a Wood lamp to check fluorescent re-entry stamps.
10. Immigration officers check that passports are genuine.
11. Banks check for counterfeit money.

d. Does the Wood Lamp Cause any Harm.

The black light emitted by a Wood lamp is harmless. The lamp does not emit short-wavelength ultraviolet B radiation (290-320 nm), so it does not cause sunburn or otherwise damage healthy skin.

It is possible that a patient with extreme photosensitivity might develop a rash on skin exposed to black light. However, Wood lamp examination is usually very brief and unlikely to cause problems even in very photosensitive patients.

It is prudent to ask the patient to close their eyes when examining the face.

e. Digital Wood Lamp Substitutes.

1. Blue Screen of a Smartphone.

One can use the Blue Screen of a Smartphone as an alternative to a Wood's lamp for examination of vitiligo. Downloading a blue image filling up the whole screen onto a smartphone, saving it to the image gallery, and opening it at the maximum brightness, leads to the emission of blue light from the device. The accentuation of vitiliginous lesions with this device are comparable to that seen with a Wood's lamp, and in addition the smartphone allowed gray-scale editing, which increased its dynamic range.

While Wood's lamp is a useful instrument for the evaluation of vitiligo lesions, it may not be readily available in resource-poor settings. Using a blue screen of a smartphone may be a comparable and effective alternative.

B. Dermatoscope.

For hundreds of years, dermatologists have used devices, primarily magnifiers with or without a light source to complement the naked eye examination of skin lesions. Dermatopscopy, a known diagnostic technique since the late 1800s, has enjoyed an unprecedented renewed interest in the past two decades, fueled by studies of increased diagnostic accuracy of melanoma that emerged in the 1980s and the wide availability of portable pock-sized handheld dermatoscopes.

A dermatascope, in addition to magnifying and providing a light source, renders the cornified layer translucent, thereby uunveiling subsurface structures within the epidermis and superficial dermis. This "deeper" view of the skin reveals additional morphologic details that cannot be appreciated with naked-eye examination.

Dermatoscopy has been promoted to be useful in diagnosing not only pigmented skin lesions, but also a wide range of skin conditions that are infectious, harmartoatous, and inflammatory in nature.

The device is so useful that some have referred to it as the new "stethoscope" of dematologists.[73]

[73] See https://www.sciencedirect.com/science/article/pii/S0738081X10002658.

A dermatoscope is composed of a transilluminating light source and a magnifying optic (usually a 10-fold magnification). There are three main modes of dermoscopy:

Nonpolarized light, contact.
Polarized light, contact.
Polarized light, noncontact.

Polarized light allows for visualization of deeper skin structures, while non-polarized light provides information about the superficial skin. Most modern dermatoscopes allow the user to toggle between the two modes, which provide complementary information.

1. Application of Dermatoscopy.
   a. The typical application of dermatoscopy is early detection of melanoma.
   b. Digital dermatoscopy (video dermatoscopy) is used for monitoring skin lesions suspicious of melanoma. Digital dermatoscopy images are stored and compared to images obtained during the patient's next visit. Suspicious changes in such a lesion are an indication for excision. Skin lesions, which appear unchanged over time are considered benign.
   c. Aid in the diagnosis of skin tumors-such as basal cell carcinomas, squamous cell carcinomas, cylindromas, dermatofibromas, angiomas, seborrheic keratosis and many other common skin tumors have classical dermatoscopic findings.
   d. Aid in the diagnosis of scabies and pubic louse. By staining the skin with India ink, a dermatoscope can help identify the location of the mite in the burrow, facilitating scraping of the scabetic burrow. By magnifying pubic louse, it allows for rapid diagnosis of the difficult to see small insects.
   e. Aid in the diagnosis of warts. By allowing a physician to visualize the structure of a wart, to distinguish it from corn, callouses, trauma, or foreign bodies. By examining warts at late stages of treatment, to assure that therapy is not stopped prematurely due to difficult to visualize wart structures.
   f. Aid in the diagnosis of fungal infections. To differentiate "black dot" tinea, or tinea capitis (fungal scalp infection) from alopecia areata.
   g. Aid in the diagnosis of hair and scalp diseases, such as alopecia areata, female androgenic alopecia, monilethrix, Netherton syndrome, and woolly hair syndrome. Dermoscopy of hair and scalp is called trichoscopy.
   h. Differentiation of tinea nigra from malignant melanoma or junctional melanocytic nevus.

Due to the fairly standardized imaging, and limited amount of diagnoses compared to clinical dermatology, dermatoscopic images became one center of interest for automated medical image analysis. While in the past decades computer vision algorithms and hardware-based methods were used, large standardized public image collections such as HAM10000 enabled application of convolutional neural networks. The latter approach has now shown experimental evidence of human-level accuracy in larger/international, and smaller/local trials, but this application is not without dispute.

2. Teledermoscopy.

Teledermoscopy is a rapidly growing field of dermatology. C. Magnifying Lamps. Virtually every dermatologist and aesthetician commences with a magnifying light, also known as a "mag light," "mag lamp," or "loupe." This gives a good start to seeing things that are hard to view with the naked eye. Sometimes, it helps to reposition the lamp to get a good view of an area.

Magnifying lamps help prevent guesswork, and they eliminate shadows and color distortion. They also make life infinitely easier for the professional by preventing squinting, neck strain, and back problems.

Newer magnifying lamps offer many features, such as reduced weight, improved stability, adjustable arms and lamp heads, one-touch or hands-free positioning, dimmable LED lights that last 50,000 hours, and multiple magnification levels.

While there are lamps with fluorescent or halogen lighting, LED lighting has become the new standard, as it provides far superior color rendering.

If portability is important, there are models that can be mounted on a rolling stand for ease of use. Look for lamps that have a reputation for stellar customer service, should something go wrong, from an FDA-approved company.

The diopters of the lamp determine the instrument's magnification. Diopters are fixed, so if different levels of magnification are needed, select a lamp that allows for choosing from several replaceable lenses, much like changing the eyepiece on a telescope or the lens on a camera.

The diopter of a lens is the reciprocal of its focal length. The higher the number of a magnifying lamp's diopters, the thicker the lens and the more it is curved. Also, the higher the number of diopters, the greater the magnification.

It is simple to convert given diopters to the lamp's magnification: divide the diopter by four and add one. For example, a three-diopter magnifying lamp (the most common strength) gives 175% magnification:

¾=0.75
75+1=1.75

The distance from the lens center to the point where the rays of light meet is the focal length of the lamp, and it is where the subject comes into perfect focus. The focal length of the lamp is the working distance between the lamp and the client's face. The greater the magnification, the shorter the working distance, which must be considered to allow room for hands, tools, and the like.

D. Full-Face Analysis.

A new frontier of skin analysis tools involves full-face analysis. These instruments allow the client to place their face in a module for viewing the entire face at once. Some systems rotate around the client's face, much like a panoramic dental x-ray.

Images from the analysis are transmitted to a camera or video system and can be helpful for both the professional and client.

Full-face skin analysis, like traditional skin analysis with a magnifying lamp and Wood's lamp, can identify and color map issues such as: fine lines and wrinkles, spots and areas of discoloration, redness, ultraviolet damage, subsurface melanin, and vascular conditions.

Some offer a magnifying loupe element and aging simulation. Before and after imaging can be helpful in assessing the success of various treatments. Some practices use this type of imaging in helping clients decide on invasive procedures.

These systems are still in the clinical trials phase, awaiting FDA approval, and they are not considered standard skin analysis devices yet. But they present an exciting opportunity for skin analysis in the future.

Once a skin analysis has been performed, a follow-up depends on the findings and the type of facility. Treatments, referral to a specialist, and homecare are all options. With a proper skin analysis, professionals will never doubt they are following up correctly. Skin analysis is the basis on which all other beauty and dermatology actions are based, so performing a correct and thorough analysis is key.

E. Thermal Cameras.

See for example but without limitation, https://www.wired.com/gallery/best-thermal-cameras-for-phones/.

What is claimed is:

1. A medical diagnosis system, comprising:
    a skin viewing device that obtains a digital representation of a skin of a subject;
    a skin analyzing computer system which analyzes the digital representation of the skin; and identifies an area of interest on the skin from the digital representation of the skin;
    the skin analyzing computer system operates to associate an augmented reality tag to the area of interest on the skin, the augmented reality tag associated with the area of interest by analyzing biometric data in the digital representation of the skin that is at least one of a skin pore pattern, a hair follicle pattern, and a blood vein pattern, and
    the skin analyzing computer finding a unique relationship among the at least one of the skin pore pattern, a hair follicle pattern, and a blood vein pattern, and using the unique relationship to mark a location of the augmented reality tag on the area of interest on the skin of the subject.

2. The system as in claim 1, wherein the augmented reality tag is an augmented reality visual mark.

3. The system as in claim 1, wherein the augmented reality tag is an audio augmented reality tag.

4. The device as in claim 1, wherein the augmented reality tag is a QR code.

5. The device as in claim 4, wherein the QR code encodes additional information.

6. The device as in claim 5, wherein the additional information includes augmented reality audio note/message.

7. The device as in claim 6, wherein the augmented reality audio note/message includes an audio description of a condition.

8. The system as in claim 1, wherein the digital representation of the skin is an image of the skin, taken with a camera.

9. The system as in claim 8 where the skin analyzing computer analyzes the image of the skin at a first time, and at a second time provides access to the area of interest using the unique relationship that identifies the area of interest and which marks the augmented reality tag.

10. The system as in claim 1, wherein the digital representation of the skin is a holographic image of the skin, taken with a holographic camera, and where the skin analyzing computer operates to associate the augmented reality tag to the holographic image at the area of interest.

11. The system as in claim 10 where the skin analyzing computer analyzes the holographic image of the skin at a first time, and at a second time provides access to the holograph of the area of interest using the unique relationship that identifies the area of interest and which marks the augmented reality tag.

12. The system as in claim 1, wherein the skin analyzing computer operates to relocate and redisplay a pre-existing visual mark.

13. The system as in claim 1, further comprising using the skin analyzing computer to provide a special code to control who can view the augmented reality tag, where only a user who has the special code can view the augmented reality tag, and a user who does not have the special code cannot view the augmented reality tag.

14. The device as in claim 1, where the augmented reality tag is generated on the skin of the subject without physical contact with the subject.

15. The device as in claim 10, where the augmented reality tag is generated on the holographic image of the skin of the subject without physical contact with the subject and from a location that is remote from the subject.

16. The device as in claim 10, where the augmented reality tag is generated on either of the holographic image of the skin of the subject without physical contact with the subject and from a location that is remote from the subject at a first time, and on the skin of the subject itself at a second time.

17. The device as in claim 1, wherein the biometric data is gathered into numerical expressions which are mathematically anchored to unique biometric data of the skin of the subject.

18. The device as in claim 17, wherein the numerical expressions are coordinates of the skin pattern in a coordinate system and where the coordinates mark the location of the augmented reality tag on the area of interest.

19. The device as in claim 1, wherein the augmented reality tag has a first color to represent an area at a first time, and in a second color to represent an area for the area at a second time different than the first time.

20. The device as in claim 1, wherein the augmented reality tag has a first color to represent a first skin issue at a first area of interest and a different color to represent a different skin issue at a second area of interest.

21. The device as in claim 1, wherein the augmented reality tag displays a volumetric size of an item on the skin.

22. The device as in claim 17, wherein the skin analyzing computer operates for storing the numerical expressions in a numerical expressions skin recognition registry, and where the skin analyzing computer operates to anchor the augmented reality tag to a location defined by the numerical expressions stored in the numerical expressions skin recognition registry.

23. The device as in claim 1, wherein the skin viewing device and the skin analyzing computer are physically local to one another and connected to one another.

24. The device as in claim 1, wherein the skin analyzing computer system is a cloud computing system, and the skin viewing device and the skin analyzing computer system are physically remote from one another.

25. A skin viewing system, comprising:
    a device that obtains a digital representation of a skin of a subject;
    a skin analyzing computer system which operates to use a first augmented reality tag to indicate a physical location on the skin at a first time as an area of interest by identifying unique biometric features on the skin at the physical location, and associating the tag with the unique biometric features, and operates to use a second augmented reality tag to indicate the physical location on the skin at a second time subsequent to the first time using the same biometric features;

and where the skin analyzing computer compares the first augmented reality tag to the second augmented reality tag to identify a change in skin condition between the first time and the second time.

26. The system as in claim 25, wherein the skin analyzing computer mathematically compares the unique biometric features to indicate the physical locations of the tags.

27. The system as in claim 25, wherein the skin analyzing computer compares the tags at different intervals of time to determine changes in skin condition over the intervals of time.

28. The system as in claim 25, wherein the skin analyzing computer analyzes biometric data that is at least one of a skin pore pattern, a hair follicle pattern, and a blood vein pattern, and forms a unique relationship among the at least one of the skin pore pattern, a hair follicle pattern, and a blood vein pattern, and using the unique relationship to mark the location of the augmented reality tag on the area of interest.

29. The system as in claim 25, wherein the augmented reality tag is an augmented reality visual mark.

30. The system as in claim 25, wherein the augmented reality tag is an audio augmented reality tag.

31. The system as in claim 25, wherein the digital representation of the skin is an image of the skin, where the device that obtains the digital representation of the skin of a subject is a camera that obtains the digital representation of the image of the skin.

32. The device as in claim 31, where the augmented reality tag is generated on the skin of the subject without physical contact with the subject.

33. The system as in claim 25, wherein the digital representation of the skin is a holographic image of the skin, where the device that obtains the digital representation of the skin of a subject is a holographic camera, the holographic camera obtains the digital representation of the image of the skin and where the skin analyzing computer operates to associate the augmented reality tag to the holographic image at the area of interest.

34. The device as in claim 33, where the augmented reality tag is generated on the holographic image of the skin of the subject without physical contact with the subject and from a location that is remote from the subject.

35. The system as in claim 25, wherein the skin analyzing computer operates to relocate and redisplay a pre-existing visual mark by finding new biometric skin data at a new location.

36. The device as in claim 25, wherein the skin analyzing computer operates to gather the biometric features into numerical expressions which are mathematically anchored to unique biometric data of the skin of the subject.

37. The device as in claim 36, wherein the numerical expressions are coordinates of the skin condition in a coordinate system.

38. A medical diagnosis system, comprising:

a holographic camera that obtains a holographic image, of at least a part of a subject's body;

a skin analyzing computer system which analyzes the holographic image of the skin; and identifies an area of interest on the holographic image of the skin from the holographic image, the skin analyzing computer being located at a location that is distant from a user;

the skin analyzing computer operating to associate an augmented reality tag to the area of interest on the skin by finding and analyzing biometric data in the holographic image and anchoring to the holographic image at a location distant from the actual subject using the biometric data to mark a location of an augmented reality tag, and later, at a subsequent time, identifying a same location on the subject by regenerating the location on the holographic image using the biometric data to mark the location of the augmented reality tag to find the location.

39. The system as in claim 38, wherein the augmented reality tag is an augmented reality visual mark.

40. The system as in claim 38, wherein the augmented reality tag is an audio augmented reality tag.

41. The system as in claim 38 where the skin analyzing computer analyzes the holographic image of the skin at a first time, and at a second time provides access to the holographic image of the area of interest using the biometric data that marks the location of augmented reality tag.

42. The system as in claim 38, wherein the using the biometric data to mark a location of the augmented reality tag comprises using and anchoring to a unique skin pore pattern of the subject near a site of the skin condition of the subject.

43. The system as in claim 38, wherein the using the augmented reality tag comprises analyzing at least one of a skin pore pattern, a hair follicle pattern, and a blood vein pattern of the subject near a site of the relevant skin condition of the subject, and forming a unique relationship among the at least one of the skin pore pattern, a hair follicle pattern, and a blood vein pattern of the subject and using the unique relationship to anchor to the location.

* * * * *